US009688988B2

(12) United States Patent
Jaschinski et al.

(10) Patent No.: US 9,688,988 B2
(45) Date of Patent: Jun. 27, 2017

(54) MODIFIED TGF-BETA OLIGONUCLEOTIDE FOR USE IN A METHOD OF PREVENTING AND/OR TREATING AN OPHTHALMIC DISEASE

(71) Applicant: ISARNA Therapeutics GmbH, München (DE)

(72) Inventors: Frank Jaschinski, Obertraubling (DE); Michel Janicot, Brussles (BE); Eugen Uhlmann, Glashütten (DE); Eugen Leo, Freiburg (DE)

(73) Assignee: ISARNA THERAPEUTICS GMBH, München (DE)

( * ) Notice: Subject to any disclaimer, the term of this patent is extended or adjusted under 35 U.S.C. 154(b) by 0 days.

(21) Appl. No.: 14/779,930

(22) PCT Filed: Mar. 27, 2014

(86) PCT No.: PCT/EP2014/056222
§ 371 (c)(1),
(2) Date: Sep. 24, 2015

(87) PCT Pub. No.: WO2014/154836
PCT Pub. Date: Oct. 2, 2014

(65) Prior Publication Data

US 2016/0040167 A1 Feb. 11, 2016

(30) Foreign Application Priority Data

| | | |
|---|---|---|
| Mar. 27, 2013 | (EP) | 13161474 |
| Jun. 20, 2013 | (EP) | 13173078 |
| Dec. 30, 2013 | (EP) | 13199826 |
| Dec. 30, 2013 | (EP) | 13199831 |
| Dec. 30, 2013 | (EP) | 13199838 |

(51) Int. Cl.
*C12N 15/113* (2010.01)

(52) U.S. Cl.
CPC ...... *C12N 15/1136* (2013.01); *C12N 2310/11* (2013.01); *C12N 2310/321* (2013.01); *C12N 2310/3231* (2013.01); *C12N 2310/341* (2013.01); *C12N 2310/351* (2013.01)

(58) Field of Classification Search
CPC .. C12N 15/111; C12N 15/113; C12N 15/1136
See application file for complete search history.

(56) References Cited

U.S. PATENT DOCUMENTS

2011/0136893 A1 6/2011 Schlingensiepen

FOREIGN PATENT DOCUMENTS

| | | | |
|---|---|---|---|
| EP | 1008649 | A2 | 6/2000 |
| EP | 2453017 | A1 | 5/2012 |
| WO | 9425588 | A2 | 11/1994 |
| WO | 2004005552 | A1 | 1/2004 |
| WO | 2005084712 | A2 | 9/2005 |
| WO | 2011154542 | A1 | 12/2011 |

OTHER PUBLICATIONS

International Search Report, European Patent Office, dated Aug. 21, 2013.

Stanton, Robert, et al., "Chemical Modification Study of Antisense Gapmers," Nucleic Acid Therapeutics, Oct. 2012, pp. 344-359, vol. 22, No. 5.

Gordon, Kelly J., et al., "Role of transforming growth factor-beta superfamily signaling pathways in human disease," Biochimica et Biophysica Acta, Molecular Basis of Disease, Feb. 11, 2008, pp. 197-228, vol. 1782, No. 4.

Takagi-Sato, Miho, et al., "Design of ENA® gapmers as fine-tuning antisense oligonucleotides with sequence-specific inhibitory activity on mouse PADI4 mRNA expression," Nucleic Acids Symposium Series, 2006, pp. 319-320, No. 50.

Prendes, Mark A., et al., "The role of transforming growth factor beta in glaucoma and the therapeutic implications," British Journal of Ophthalmology, Jan. 15, 2013, pp. 680-686, vol. 97, No. 6.

*Primary Examiner* — Jon E Angell

(74) *Attorney, Agent, or Firm* — Gianna J. Arnold; Saul Ewing LLP

(57) ABSTRACT

The invention refers to an oligonucleotide consisting of 10 to 20 nucleotides of selected regions of the TGF-beta1, TGF-beta2 or TGF-beta3 nucleic acid sequence, which comprises modified nucleotides such as LNA, ENA, polyalkylene oxide-, 2'-fluoro, 2'-O-methoxy and/or 2'-O-methyl modified nucleotides. The invention further relates to pharmaceutical compositions comprising such oligonucleotide, wherein the composition or the oligonucleotide is used in a method for the prevention and/or treatment of glaucoma, posterior capsular opacification, dry eye, Marfan or Loeys-Dietz syndrome, riboblastoma, choroidcarcinoma, macular degeneration, such as age-related macular degeneration, diabetic macular endma, or cataract.

11 Claims, 45 Drawing Sheets

Fig. 1: Nucleic acid sequence of human TGF-beta1 (SEQ ID No. 1) mRNA (NCBI Reference Sequence NM_000660.4)

```
   1 ccccgccgcc gccgcccttc gcgccctggg ccatctccct cccacctccc tccgcggagc
  61 agccagacag cgagggcccc ggccgggggc aggggggacg ccccgtccgg ggcacccccc
 121 cggctctgag ccgcccgcgg ggccggcctc ggcccggagc ggaggaagga gtcgccgagg
 181 agcagcctga ggccccagag tctgagacga gccgccgccg cccccgccac tgcggggagg
 241 agggggagga ggagcgggag gagggacgag ctggtcggga gaagaggaaa aaaacttttg
 301 agacttttcc gttgccgctg ggagccggag gcgcggggac ctcttggcgc gacgctgccc
 361 cgcgaggagg caggacttgg ggaccccaga ccgcctccct ttgccgccgg ggacgcttgc
 421 tccctccctg cccccctacac ggcgtccctc aggcgccccc attccggacc agccctcggg
 481 agtcgccgac ccggcctccc gcaaagactt ttccccagac ctcgggcgca ccccctgcac
 541 gccgccttca tccccggcct gtctcctgag cccccgcgca tcctagaccc tttctcctcc
 601 aggagacgga tctctctccg acctgccaca gatcccctat tcaagaccac ccaccttctg
 661 gtaccagatc gcgcccatct aggttatttc cgtgggatac tgagacaccc ccggtccaag
 721 cctcccctcc accactgcgc ccttctccct gaggacctca gctttccctc gaggccctcc
 781 taccttttgc cgggagaccc ccagcccctg caggggcggg gcctccccac cacaccagcc
 841 ctgttcgcgc tctcggcagt gccgggggc gccgcctccc ccatgccgcc ctccgggctg
 901 cggctgctgc cgctgctgct accgctgctg tggctactgg tgctgacgcc tggccggccg
 961 gccgcgggac tatccacctg caagactatc gacatggagc tggtgaagcg gaagcgcatc
1021 gaggccatcc gcggccagat cctgtccaag ctgcggctcg ccagcccccc gagccagggg
1081 gaggtgccgc ccggcccgct gcccgaggcc gtgctcgccc tgtacaacag cacccgcgac
1141 cgggtggccg gggagagtgc agaaccggag cccgagcctg aggccgacta ctacgccaag
1201 gaggtcaccc gcgtgctaat ggtggaaacc cacaacgaaa tctatgacaa gttcaagcag
1261 agtacacaca gcatatatat gttcttcaac acatcagagc tccgagaagc ggtacctgaa
1321 cccgtgttgc tctcccgggc agagctgcgt ctgctgaggc tcaagttaaa agtggagcag
1381 cacgtggagc tgtaccagaa atacagcaac aattcctggc gatacctcag caaccggctg
1441 ctggcaccca gcgactcgcc agagtggtta tcttttgatg tcaccggagt tgtgcggcag
1501 tggttgagcc gtggagggga aattgagggc tttcgcctta gcgcccactg ctcctgtgac
1561 agcagggata acacactgca agtggacatc aacgggttca ctaccggccg ccgaggtgac
1621 ctggccacca ttcatggcat gaaccggcct ttcctgcttc tcatggccac cccgctggag
1681 agggcccagc atctgcaaag ctcccggcac cgccgagccc tggacaccaa ctattgcttc
1741 agctccacgg agaagaactg ctgcgtgcgg cagctgtaca ttgacttccg caaggacctc
1801 ggctggaagt ggatccacga gcccaagggc taccatgcca acttctgcct cgggccctgc
1861 ccctacattt ggagcctgga cacgcagtac agcaaggtcc tggccctgta caaccagcat
1921 aacccgggcg cctcggcggc gccgtgctgc gtgccgcagg cgctggagcc gctgcccatc
1981 gtgtactacg tgggccgcaa gcccaaggtg gagcagctgt ccaacatgat cgtgcgctcc
2041 tgcaagtgca gctgaggtcc cgccccgccc cgccccgccc cggcaggccc ggccccaccc
2101 cgccccgccc ccgctgcctt gcccatgggg gctgtattta aggacacccg tgccccaagc
2161 ccacctgggg ccccattaaa gatggagaga ggactgcgga aaaaaaaaaa aaaaaaa
```

Fig. 2A

Fig. 2A: Nucleic acid sequence of human TGF-beta2 (SEQ ID No. 2) mRNA (NCBI Reference Sequence NM_003238.3

```
   1 gtgatgttat ctgctggcag cagaaggttc gctccgagcg gagctccaga agctcctgac
  61 aagagaaaga cagattgaga tagagataga aagagaaaga gagaaagaga cagcagagcg
 121 agagcgcaag tgaaagaggc aggggagggg gatggagaat attagcctga cggtctaggg
 181 agtcatccag gaacaaactg aggggctgcc cggctgcaga caggaggaga cagagaggat
 241 ctattttagg gtggcaagtg cctacctacc ctaagcgagc aattccacgt tggggagaag
 301 ccagcagagg ttgggaaagg gtgggagtcc aagggagccc ctgcgcaacc ccctcaggaa
 361 taaaactccc cagccagggt gtcgcaaggg ctgccgttgt gatccgcagg gggtgaacgc
 421 aaccgcgacg gctgatcgtc tgtggctggg ttggcgtttg gagcaagaga aggaggagca
 481 ggagaaggag ggagctggag gctggaagcg tttgcaagcg gcggcggcag caacgtggag
 541 taaccaagcg ggtcagcgcg cgcccgccag ggtgtaggcc acggagcgca gctcccagag
 601 caggatccgc gccgcctcag cagcctctgc ggcccctgcg gcacccgacc gagtaccgag
 661 cgccctgcga agcgcaccct cctccccgcg gtgcgctggg ctcgccccca gcgcgcgcac
 721 acgcacacac acacacacac acacacacgc acgcacacac gtgtgcgctt ctctgctccg
 781 gagctgctgc tgctcctgct ctcagcgccg cagtggaagg caggaccgaa ccgctccttc
 841 tttaaatata taaatttcag cccaggtcag cctcggcggc ccccctcacc gcgctcccgg
 901 cgcccctccc gtcagttcgc cagctgccag ccccgggacc ttttcatctc ttcccttttg
 961 gccggaggag ccgagttcag atccgccact ccgcacccga gactgacaca ctgaactcca
1021 cttcctcctc ttaaatttat ttctacttaa tagccactcg tctctttttt tccccatctc
1081 attgctccaa gaattttttt cttcttactc gccaaagtca gggttccctc tgcccgtccc
1141 gtattaatat ttccactttt ggaactactg gccttttctt tttaaaggaa ttcaagcagg
1201 atacgttttt ctgttgggca ttgactagat tgtttgcaaa agtttcgcat caaaaacaac
1261 aacaacaaaa aaccaaacaa ctctccttga tctatacttt gagaattgtt gatttctttt
1321 ttttattctg acttttaaaa acaacttttt tttccacttt tttaaaaaat gcactactgt
1381 gtgctgagcg cttttctgat cctgcatctg gtcacggtcg cgctcagcct gtctacctgc
1441 agcacactcg atatggacca gttcatgcgc aagaggatcg aggcgatccg cgggcagatc
1501 ctgagcaagc tgaagctcac cagtccccca gaagactatc ctgagcccga ggaagtcccc
1561 ccggaggtga tttccatcta caacagcacc agggacttgc tccaggagaa ggcgagccgg
1621 agggcggccg cctgcgagcg cgagaggagc gacgaagagt actacgccaa ggaggtttac
1681 aaaatagaca tgccgccctt cttcccctcc gaaaatgcca tcccgcccac tttctacaga
1741 ccctacttca gaattgttcg atttgacgtc tcagcaatgg agaagaatgc ttccaatttg
1801 gtgaaagcag agttcagagt ctttcgtttg cagaacccaa aagccagagt gcctgaacaa
1861 cggattgagc tatatcagat tctcaagtcc aaagatttaa catctccaac ccagcgctac
1921 atcgacagca aagttgtgaa aacaagagca gaaggcgaat ggctctcctt cgatgtaact
1981 gatgctgttc atgaatggct tcaccataaa gacaggaacc tgggatttaa aataagctta
2041 cactgtccct gctgcacttt tgtaccatct aataattaca tcatcccaaa taaaagtgaa
2101 gaactagaag caagatttgc aggtattgat ggcacctcca catataccag tggtgatcag
2161 aaaactataa agtccactag gaaaaaaaac agtgggaaga ccccacatct cctgctaatg
2221 ttattgccct cctacagact tgagtcacaa cagaccaacc ggcggaagaa gcgtgctttg
2281 gatgcggcct attgctttag aaatgtgcag gataattgct gcctacgtcc actttacatt
2341 gatttcaaga gggatctagg gtggaaatgg atacacgaac ccaaagggta caatgccaac
2401 ttctgtgctg gagcatgccc gtatttatgg agttcagaca ctcagcacag cagggtcctg
2461 agcttatata ataccataaa tccagaagca tctgcttctc cttgctgcgt gtcccaagat
2521 ttagaacctc taaccattct ctactacatt ggcaaaacac ccaagattga acagctttct
2581 aatatgattg taaagtcttg caaatgcagc taaaattctt ggaaaagtgg caagaccaaa
2641 atgacaatga tgatgataat gatgatgacg acgacaacga tgatgcttgt aacaagaaaa
2701 cataagagag ccttggttca tcagtgttaa aaaatttttg aaaaggcggt actagttcag
2761 acactttgga agtttgtgtt ctgtttgtta aaactggcat ctgacacaaa aaaagttgaa
2821 ggccttattc tacatttcac ctactttgta agtgagagag acaagaagca aatttttttt
2881 aaagaaaaaa ataaacactg gaagaattta ttagtgttaa ttatgtgaac aacgacaaca
2941 acaacaacaa caacaaacag gaaaatccca ttaagtggag ttgctgtacg taccgttcct
3001 atcccgcgcc tcacttgatt tttctgtatt gctatgcaat aggcaccctt cccattctta
3061 ctcttagagt taacagtgag ttatttattg tgtgttacta tataatgaac gtttcattgc
3121 ccttggaaaa taaaacaggt gtataaagtg gagaccaaat actttgccag aaactcatgg
3181 atggcttaag gaacttgaac tcaaacgagc cagaaaaaaa gaggtcatat taatgggatg
3241 aaaacccaag tgagttatta tatgaccgag aaagtctgca ttaagataaa gaccctgaaa
3301 acacatgtta tgtatcagct gcctaaggaa gctttcttgta aggtccaaaa actaaaaaga
3361 ctgttaataa aagaaacttt cagtcagaat aagtctgtaa gttttttttt ttctttttaa
3421 ttgtaaatgg ttctttgtca gtttagtaaa ccagtgaaat gttgaaatgt tttgacatgt
```

Fig. 2B

```
3481 actggtcaaa cttcagacct taaaatattg ctgtatagct atgctatagg tttttccctt
3541 tgttttggta tatgtaacca tacctatatt attaaaatag atggatatag aagccagcat
3601 aattgaaaac acatctgcag atctcttttg caaactatta aatcaaaaca ttaactactt
3661 tatgtgtaat gtgtaaattt ttaccatatt ttttatattc tgtaataatg tcaactatga
3721 tttagattga cttaaatttg ggctcttttt aatgatcact cacaaatgta tgtttctttt
3781 agctggccag tacttttgag taaagcccct atagtttgac ttgcactaca aatgcatttt
3841 tttttaata acatttgccc tacttgtgct ttgtgtttct ttcattatta tgacataagc
3901 tacctgggtc cacttgtctt ttcttttttt tgtttcacag aaaagatggg ttcgagttca
3961 gtggtcttca tcttccaagc atcattacta accaagtcag acgttaacaa atttttatgt
4021 taggaaaagg aggaatgtta tagatacata gaaaattgaa gtaaaatgtt ttcattttag
4081 caaggattta gggttctaac taaaactcag aatctttatt gagttaagaa aagtttctct
4141 accttggttt aatcaatatt tttgtaaaat cctattgtta ttacaaagag gacacttcat
4201 aggaaacatc tttttcttta gtcaggtttt taatattcag gggaaattg aaagatatat
4261 attttagtcg atttttcaaa aggggaaaaa agtccaggtc agcataagtc attttgtgta
4321 tttcactgaa gttataaggt ttttataaat gttctttgaa ggggaaaagg cacaagccaa
4381 tttttcctat gatcaaaaaa ttctttcttt cctctgagtg agagttatct atatctgagg
4441 ctaaagttta ccttgcttta ataaataatt tgccacatca ttgcagaaga ggtatcctca
4501 tgctggggtt aatagaatat gtcagtttat cacttgtcgc ttatttagct ttaaaataaa
4561 aattaatagg caaagcaatg gaatatttgc agtttcacct aaagagcagc ataaggaggc
4621 gggaatccaa agtgaagttg tttgatatgg tctacttctt ttttggaatt tcctgaccat
4681 taattaaaga attggatttg caagtttgaa aactggaaaa gcaagagatg ggatgccata
4741 atagtaaaca gcccttgtgt tggatgtaac ccaatcccag atttgagtgt gtgttgatta
4801 tttttttgtc ttccactttt ctattatgtg taaatcactt ttatttctgc agacattttc
4861 ctctcagata ggatgacatt ttgttttgta ttattttgtc tttcctcatg aatgcactga
4921 taatatttta aatgctctat tttaagatct cttgaatctg tttttttttt ttttaatttg
4981 ggggttctgt aaggtcttta tttcccataa gtaaatattg ccatgggagg ggggtggagg
5041 tggcaaggaa ggggtgaagt gctagtatgc aagtgggcag caattatttt tgtgttaatc
5101 agcagtacaa tttgatcgtt ggcatggtta aaaaatggaa tataagatta gctgttttgt
5161 attttgatga ccaattacgc tgtattttaa cacgatgtat gtctgttttt gtggtgctct
5221 agtggtaaat aaattatttc gatgatatgt ggatgtcttt ttcctatcag taccatcatc
5281 gagtctagaa aacacctgtg atgcaataag actatctcaa gctggaaaag tcataccacc
5341 tttccgattg ccctctgtgc tttctccctt aaggacagtc acttcagaag tcatgcttta
5401 aagcacaaga gtcaggccat atccatcaag gatagaagaa atccctgtgc cgtcttttta
5461 ttcccttatt tattgctatt tggtaattgt ttgagattta gtttccatcc agcttgactg
5521 ccgaccagaa aaaatgcaga gagatgtttg caccatgctt tggctttctg gttctatgtt
5581 ctgccaacgc cagggccaaa agaactggtc tagacagtat cccctgtagc cccataactt
5641 ggatagttgc tgagccagcc agatataaca agagccacgt gctttctggg gttggttgtt
5701 tgggatcagc tacttgcctg tcagtttcac tggtaccact gcaccacaaa caaaaaaacc
5761 caccctattt cctccaattt ttttggctgc tacctacaag accagactcc tcaaacgagt
5821 tgccaatctc ttaataaata ggattaataa aaaaagtaat tgtgactcaa aaaaaaaaaa
5881 aa
```

Fig. 3A: Nucleic acid sequence of human TGF-beta3 (SEQ ID No. 3) mRNA (NCBI Reference Sequence NM_003239.2 gacagaagca atggccgagg cagaagacaa gccgaggtgc tggtgaccct
gggcgtctga gtggatgatt ggggctgctg cgctcagagg cctgcctccc
tgccttccaa tgcatataac cccacacccc agccaatgaa gacgagaggc
agcgtgaaca aagtcattta gaaagccccc gaggaagtgt aaacaaaaga
gaaagcatga atggagtgcc tgagagacaa gtgtgtcctg tactgccccc
acctttagct gggccagcaa ctgcccggcc ctgcttctcc ccacctactc
actggtgatc tttttttttt tacttttttt tcccttttct tttccattct
cttttcttat tttctttcaa ggcaaggcaa ggattttgat tttgggaccc
agccatggtc cttctgcttc ttctttaaaa tacccacttt ctccccatcg
ccaagcggcg tttggcaata tcagatatcc actctattta tttttaccta
aggaaaaact ccagctccct tcccactccc agctgccttg ccacccctcc
cagccctctg cttgccctcc acctggcctg ctgggagtca gagcccagca
aaacctgttt agacacatgg acaagaatcc cagcgctaca aggcacacag
tccgcttctt cgtcctcagg gttgccagcg cttcctggaa gtcctgaagc
tctcgcagtg cagtgagttc atgcaccttc ttgccaagcc tcagtctttg
ggatctgggg aggccgcctg gttttcctcc ctccttctgc acgtctgctg
gggtctcttc ctctccaggc cttgccgtcc ccctggcctc tcttcccagc
tcacacatga agatgcactt gcaaagggct ctggtggtcc tggccctgct
gaactttgcc acggtcagcc tctctctgtc cacttgcacc accttggact
tcggccacat caagaagaag agggtggaag ccattagggg acagatcttg
agcaagctca ggctcaccag ccccccctgag ccaacggtga tgacccacgt
cccctatcag gtcctggccc tttacaacag cacccgggag ctgctggagg
agatgcatgg ggagagggag gaaggctgca cccaggaaaa caccgagtcg
gaatactatg ccaaagaaat ccataaattc gacatgatcc aggggctggc
ggagcacaac gaactggctg tctgccctaa aggaattacc tccaaggttt
tccgcttcaa tgtgtcctca gtggagaaaa atagaaccaa cctattccga
gcagaattcc gggtcttgcg ggtgcccaac cccagctcta agcggaatga
gcagaggatc gagctcttcc agatccttcg gccagatgag cacattgcca
aacagcgcta tatcggtggc aagaatctgc ccacacgggg cactgccgag
tggctgtcct ttgatgtcac tgacactgtg cgtgagtggc tgttgagaag

Fig. 3B agagtccaac ttaggtctag aaatcagcat tcactgtcca tgtcacacct
ttcagcccaa tggagatatc ctggaaaaca ttcacgaggt gatggaaatc
aaattcaaag gcgtggacaa tgaggatgac catggccgtg gagatctggg
gcgcctcaag aagcagaagg atcaccacaa ccctcatcta atcctcatga
tgattccccc acaccggctc gacaacccgg gccagggggg tcagaggaag
aagcgggctt tggacaccaa ttactgcttc cgcaacttgg aggagaactg
ctgtgtgcgc cccctctaca ttgacttccg acaggatctg ggctggaagt
gggtccatga acctaagggc tactatgcca acttctgctc aggcccttgc
ccatacctcc gcagtgcaga cacaacccac agcacggtgc tgggactgta
caacactctg aaccctgaag catctgcctc gccttgctgc gtgccccagg
acctggagcc cctgaccatc ctgtactatg ttgggaggac ccccaaagtg
gagcagctct ccaacatggt ggtgaagtct tgtaaatgta gctgagaccc
cacgtgcgac agagagaggg gagagagaac caccactgcc tgactgcccg
ctcctcggga aacacacaag caacaaacct cactgagagg cctggagccc
acaaccttcg gctccgggca aatggctgag atggaggttt ccttttggaa
catttctttc ttgctggctc tgagaatcac ggtggtaaag aaagtgtggg
tttggttaga ggaaggctga actcttcaga acacacagac tttctgtgac
gcagacagag gggatgggga tagaggaaag ggatggtaag ttgagatgtt
gtgtggcaat gggatttggg ctaccctaaa gggagaagga agggcagaga
atggctgggt cagggccaga ctggaagaca cttcagatct gaggttggat
ttgctcattg ctgtaccaca tctgctctag ggaatctgga ttatgttata
caaggcaagc attttttttt ttttttaaa gacaggttac gaagacaaag
tcccagaatt gtatctcata ctgtctggga ttaagggcaa atctattact
tttgcaaact gtcctctaca tcaattaaca tcgtgggtca ctacagggag
aaaatccagg tcatgcagtt cctggcccat caactgtatt gggccttttg
gatatgctga acgcagaaga aagggtggaa atcaaccctc tcctgtctgc
cctctgggtc cctcctctca cctctccctc gatcatattt ccccttggac
acttggttag acgccttcca ggtcaggatg cacatttctg gattgtggtt
ccatgcagcc ttggggcatt atgggttctt cccccacttc ccctccaaga
ccctgtgttc atttggtgtt cctggaagca ggtgctacaa catgtgaggc
attcggggaa gctgcacatg tgccacacag tgacttggcc ccagacgcat
agactgaggt ataaagacaa gtatgaatat tactctcaaa atctttgtat
aaataaatat ttttggggca tcctggatga tttcatcttc tggaatattg
tttctagaac agtaaaagcc ttattctaag gtg Fig. 4: Nucleotide /nucleoside modifications
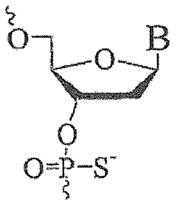
Phosphorthioate
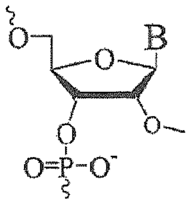
2'-O-Methyl
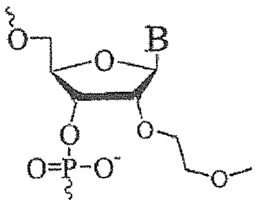
2'-MOE
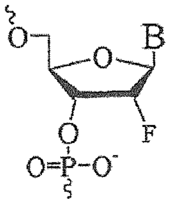
2'-Fluoro
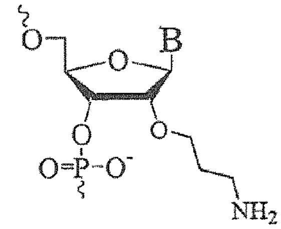
2'-AP
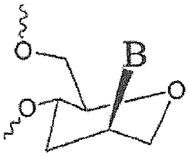
HNA
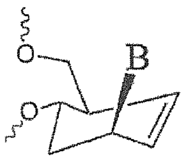
CeNA
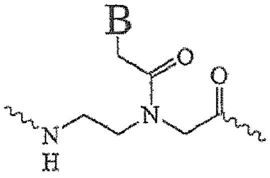
PNA
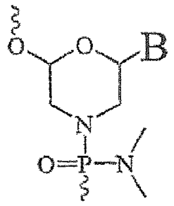
Morpholino
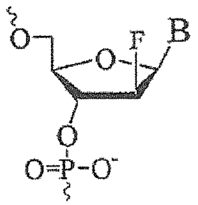
2'-F-ANA
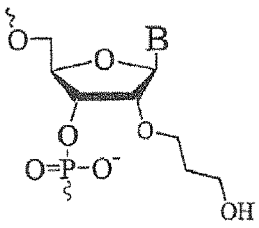
2'-(3-hydroxy)propyl
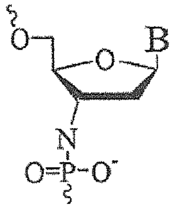
3'-Phosphoramidate
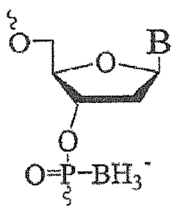
Boranophosphates Fig. 20: Homology of ASPH_1024 and ASPH_1096 with human mRNAs

ASPH_1024 and ASPH_1096: 100% homology to human TGF-beta1 a) Position of ASPH_0009, ASPH_10024, and ASPH_1096 on human TGF-beta 2 mRNA

2361 GTGGAAATGGATACACGAACCCAAAGGGTACAATGCCAACTTCTGTGCTGGAGCATGCCC

(1024: bolt+underligned, 1096: yellow shadow)

Alignment of ASPH_1096 and ASPH_1024 with human TGF-beta2 mRNA

5′ AGAAGTTGGCATGGT 3′ ASPH_1096
3′ TCTTCAACCGTAACA 5′ human TGF-beta2

5′ ATGGTAGCCCTTGG 3′ ASPH_1024
3′ TAACATGGGAAACC 5′ human TGF-beta2 b) Position of ASPH_0009, ASPH_10024, and ASPH_1096 on human TGF-beta 3 mRNA

1851 GGGTCCATGAACCTAAGGGCTACTATGCCAACTTCTGCTCAGGCCCTTGCCCATACCTCCGC

(1024: bolt+underligned, 1096: yellow shadow)

Alignment of ASPH_1096 and ASPH_1024 with human TGF-beta3 mRNA

5′ AGAAGTTGGCATGGT 3′ ASPH_1096
3′ TCTTCAACCGTATCA 5′ human TGF-beta3

5′ ATGGTAGCCCTTGG 3′ ASPH_1024
3′ TATCATCGGGAATC 3′ human TGF-beta3

Fig. 21: Homology of ASPH_1131 and ASPH_1132 with human mRNAs

100% homology with human TGF-beta1 (1123-1136) and TGF-beta3 (1073-1086)

Position on human TGF-beta2 mRNA

1561 CCGGAGGTGA TTTCCATCTA CAACAGCACC AGGGACTTGC TCCAGGAGAA GGCGAGCCGG alignment with human TGF-beta 2
5′ CGGGTGCTGTTGTA 3′ ASPH_1132
3′ GACCACGACAACAT 5′ human TGF-beta2

5′ CGGGTGCTGTTGTA 3′ ASPH_1131
3′ GACCACGACAACAT 5′ human TGF-beta2

Fig. 22: Homology of ASPH_1131 and ASPH_1132 with murine mRNAs

Position on mouse TGF-beta1 mRNA

1081 CCGCTGCCCG AGGCGGTGCT CGCTTTGTAC AACAGCACCC GCGACCGGGT GGCAGGCGAG alignment with mouse TGF-beta1 mRNA 5' CGGGTGCTGTTGTA 3' ASPH_1132
3' GCCCACGACAACAT 3' mouse TGF-beta 1

5' CGGGTGCTGTTGTA 3' ASPH_1131
3' GCCCACGACAACAT 3' mouse TGF-beta1

➔ 100% homology with mouse TGF-beta 1

Position on mouse TGF-beta2 mRNA 1401 tgaggtcccc ccggaggtga tttccatcta caacagtacc aggg

Alignment with mouse TGF-beta2

5' CGGGTGCTGTTGTA 3' ASPH_1132
3' GACCATGACAACAT 5' mouse TGF-beta2

5' CGGGTGCTGTTGTA 3' ASPH_1131
3' GACCATGACAACAT 5' mouse TGF-beta2

Position on mouse TGF-beta3 mRNA 1321 cactttacaa cagcacccgg gagttgctgg aagagatgca cggggagagg gaggaaggct Alignment with mouse TGF-beta3

5' CGGGTGCTGTTGTA 3' ASPH_1132
3' GCCCACGACAACAT 5' mouse TGF-beta3

Fig. 23: TGF-beta down-regulation in kidney
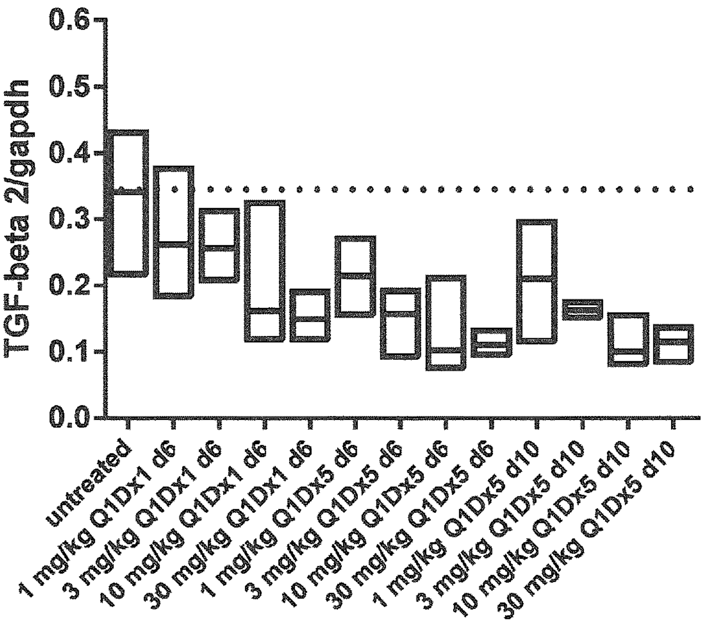
Fig. 24: TGF-beta down-regulation in human pancreatic carcinoma Panc-1 tumors
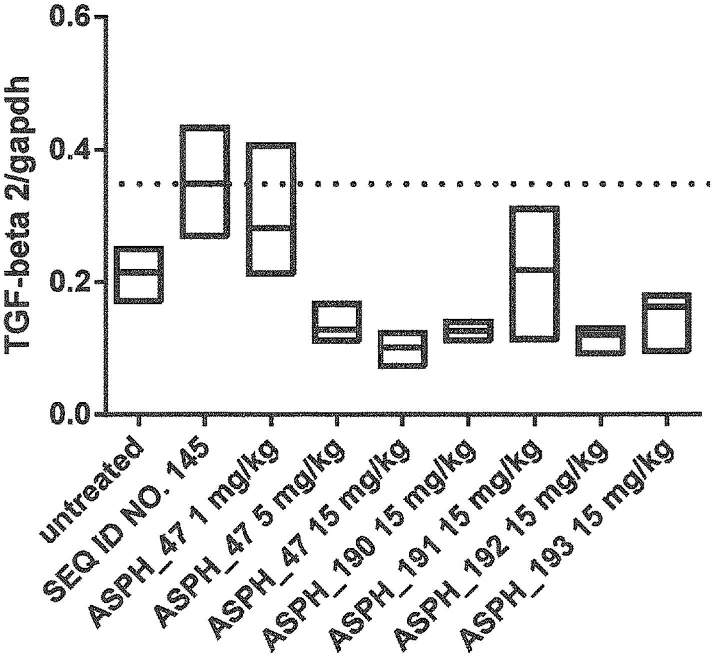

Fig. 25: TGF-beta2 down-regulation in subcutaneous human renal cell carcinoma 786-O tumors
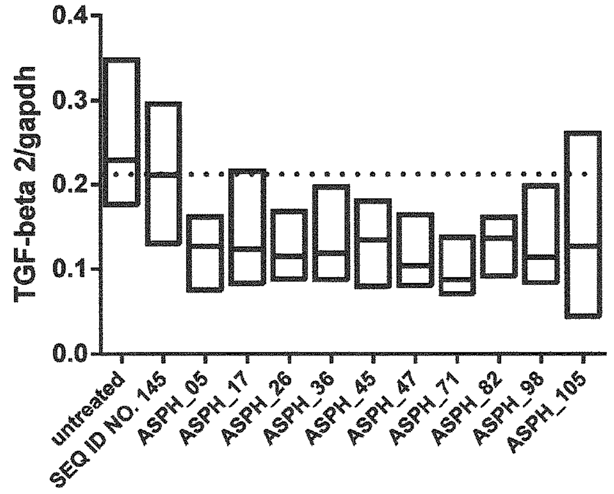
Fig. 26a: Effect on protein level by use of ASPH47
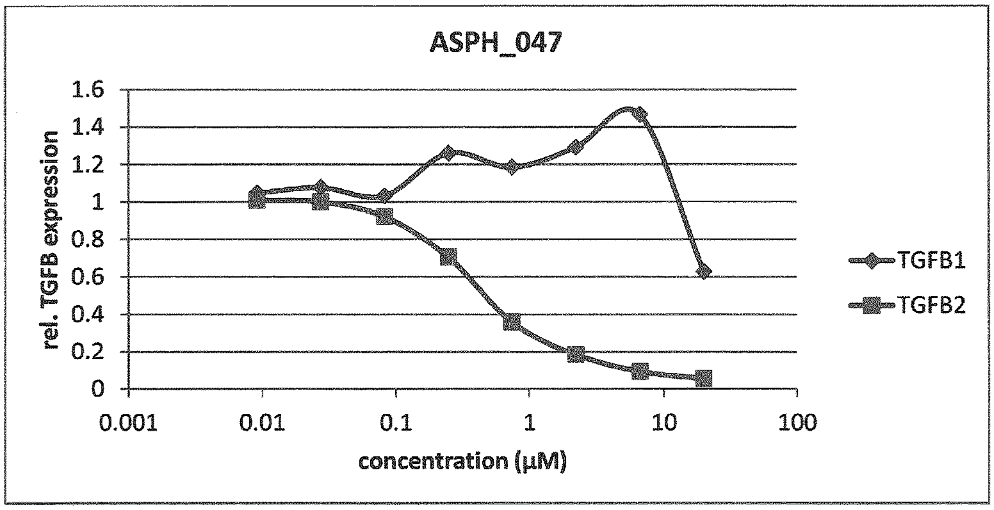

Fig, 26b: Effect on protein level by use of ASPH1047
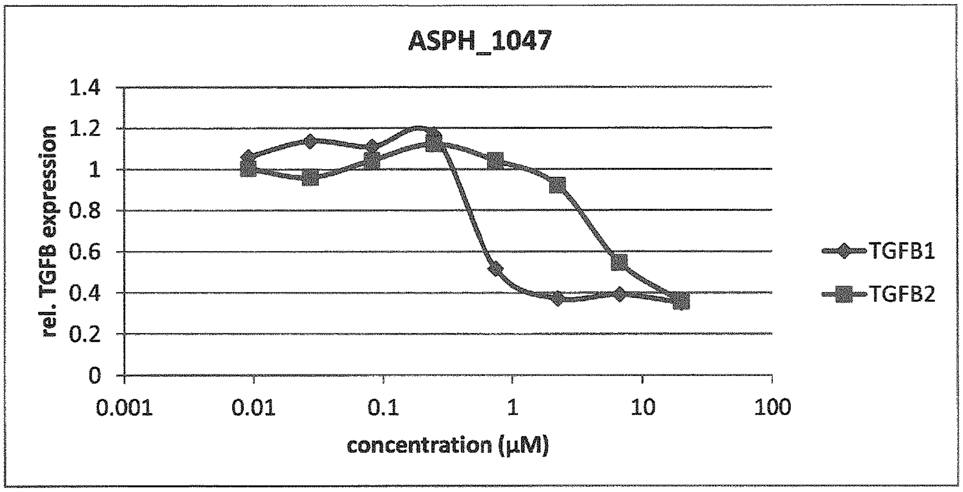
Fig. 26c: Effect on protein level by use of ASPH1106
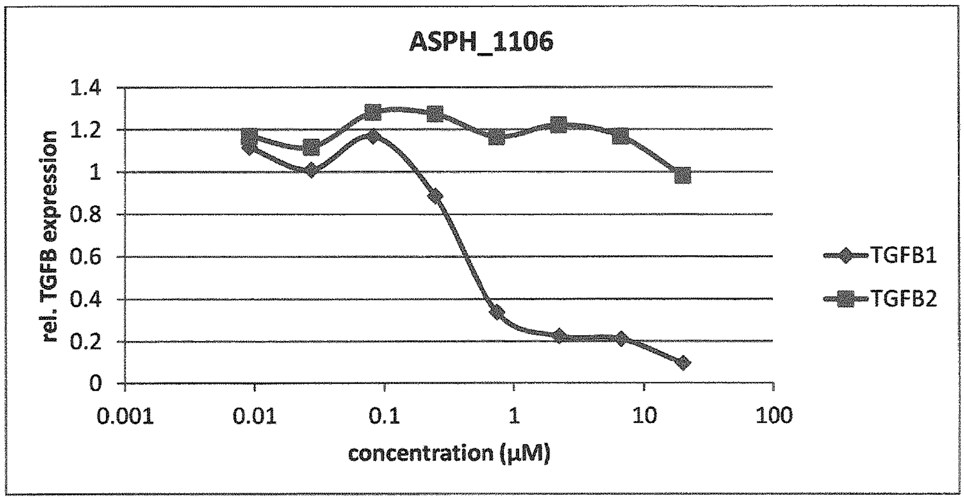

Fig. 26d: Effect on protein level by use of multispecific ASPH1132
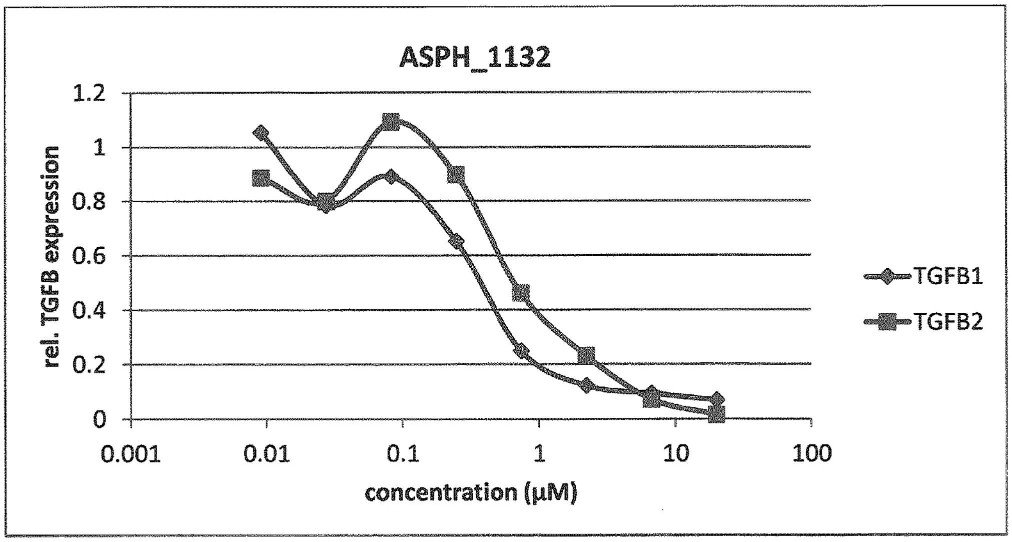
Fig. 26e: Effect on protein level by use of a combination of ASPH47 and ASPH1047
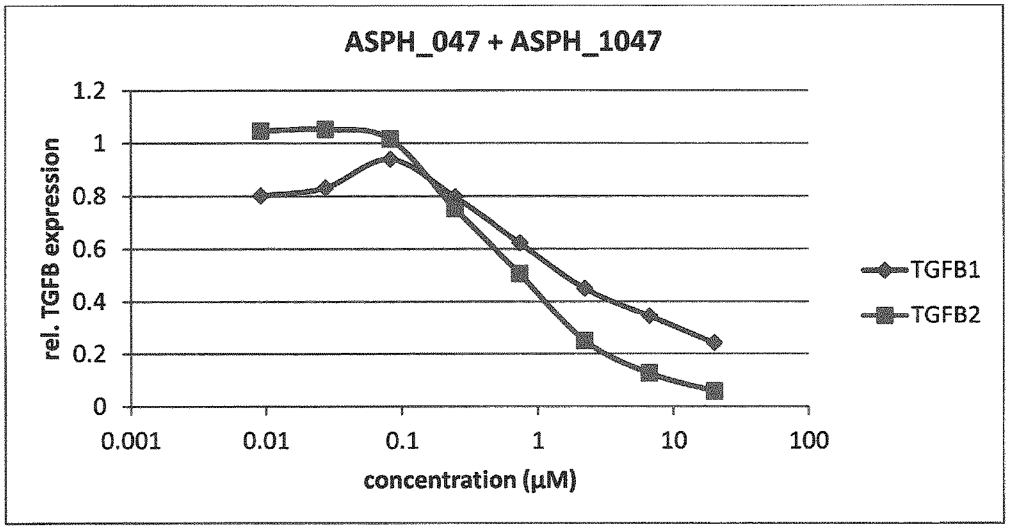

Fig. 26f: negative control - scrLNA
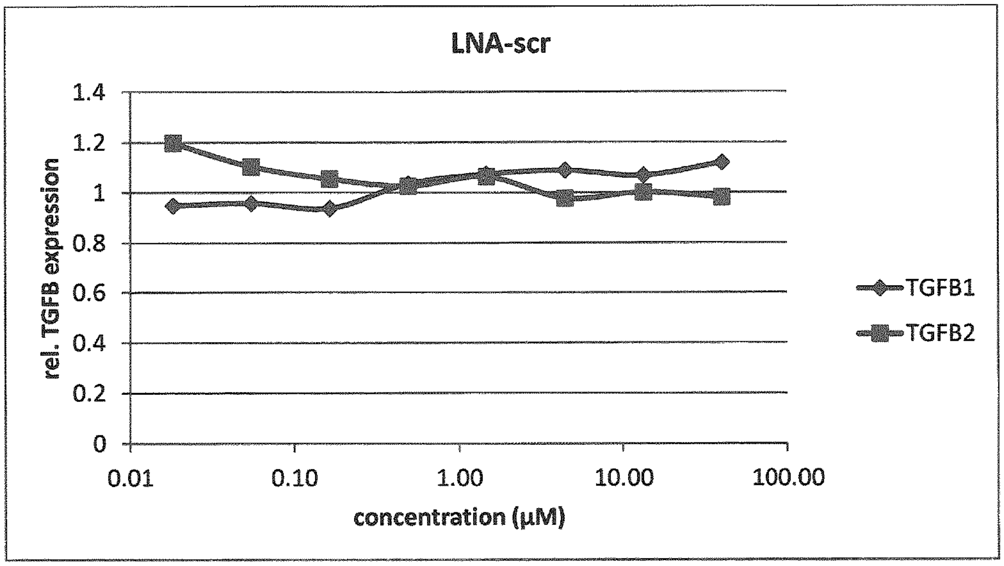

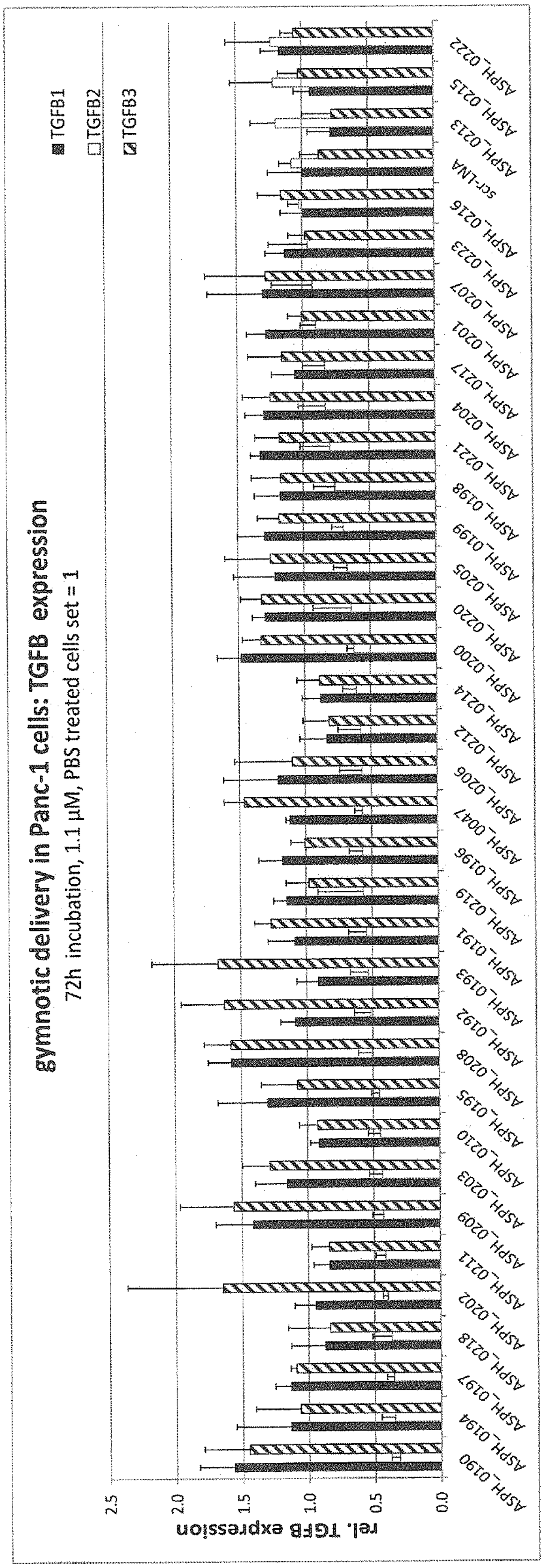
Fig. 27a: Inhibition of TGF-beta1, -2, or -3 expression in Panc-1 cells

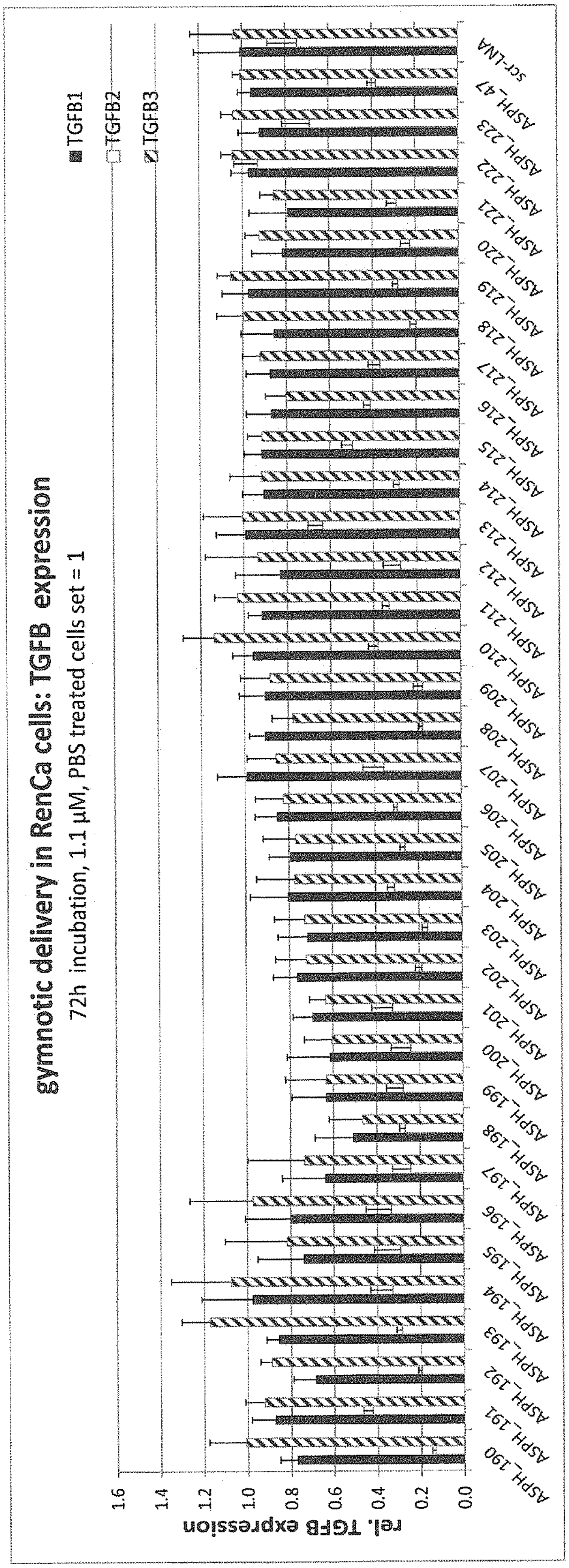
Fig. 27b: Inhibition of TGF-beta1, -2, or -3 expression in RenCa cells Fig. 29)
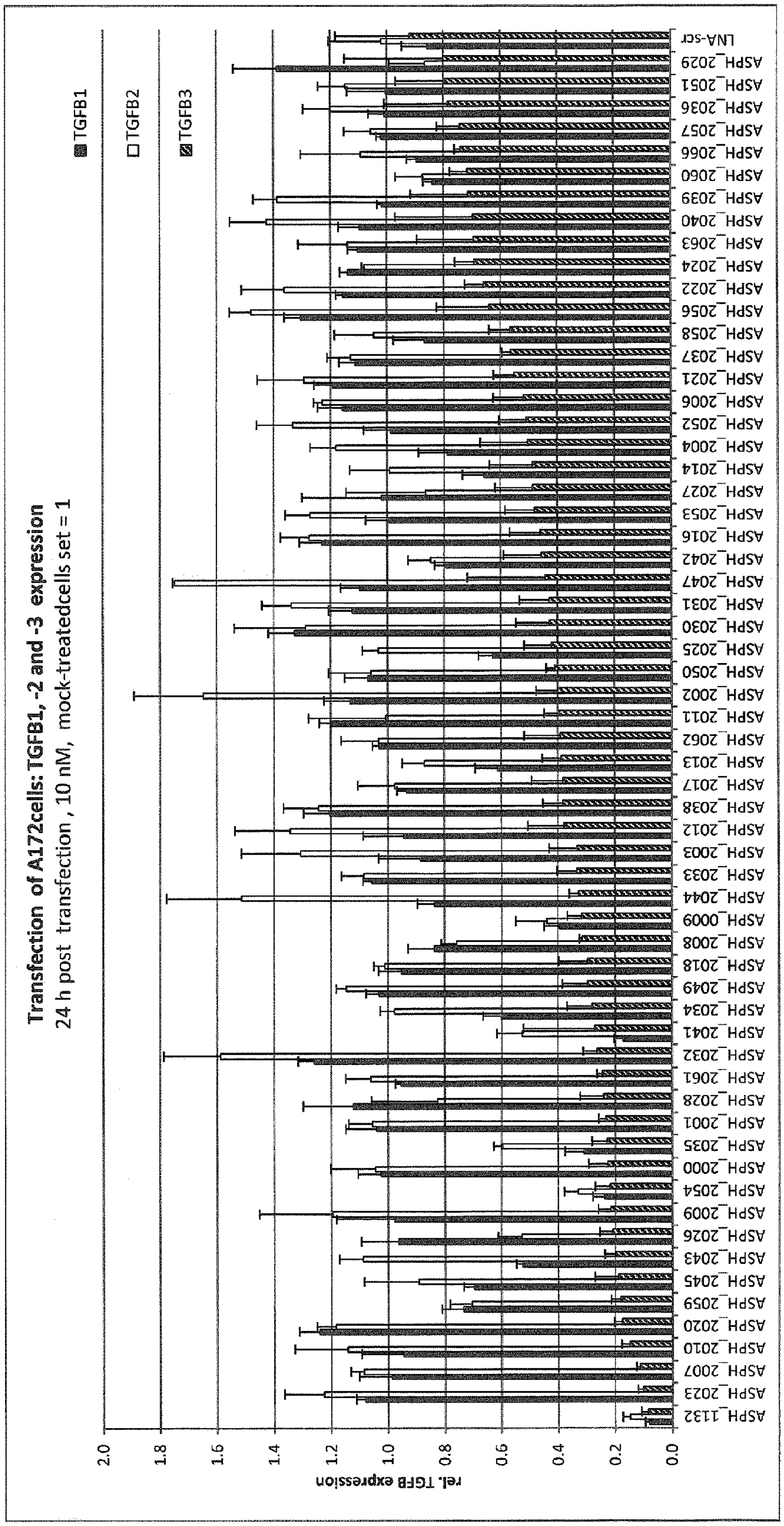

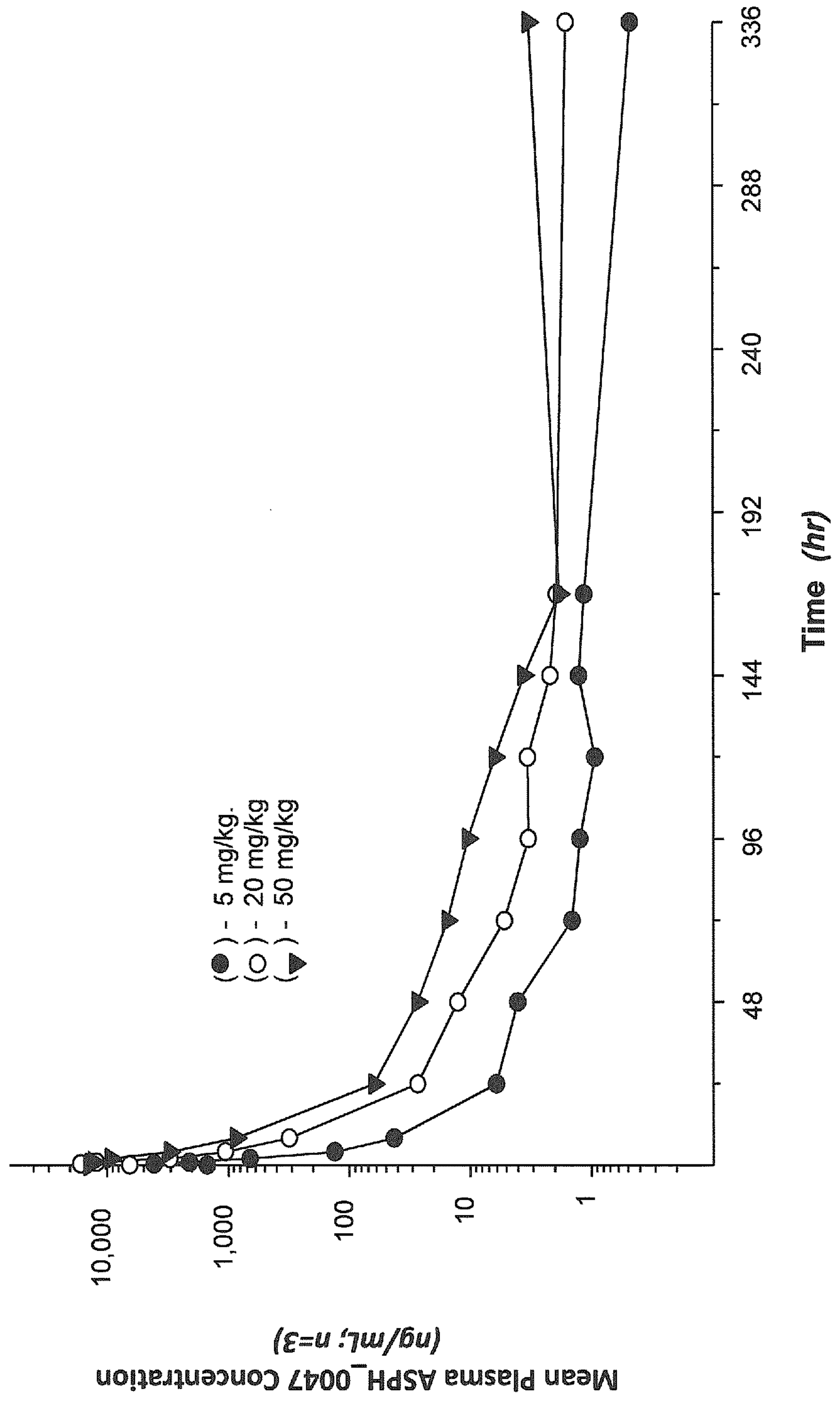
Fig. 30a) Tissue distribution of ASPH0047

Fig. 30b) TGF-beta2 downregulation by ASPH00047 in the kidney
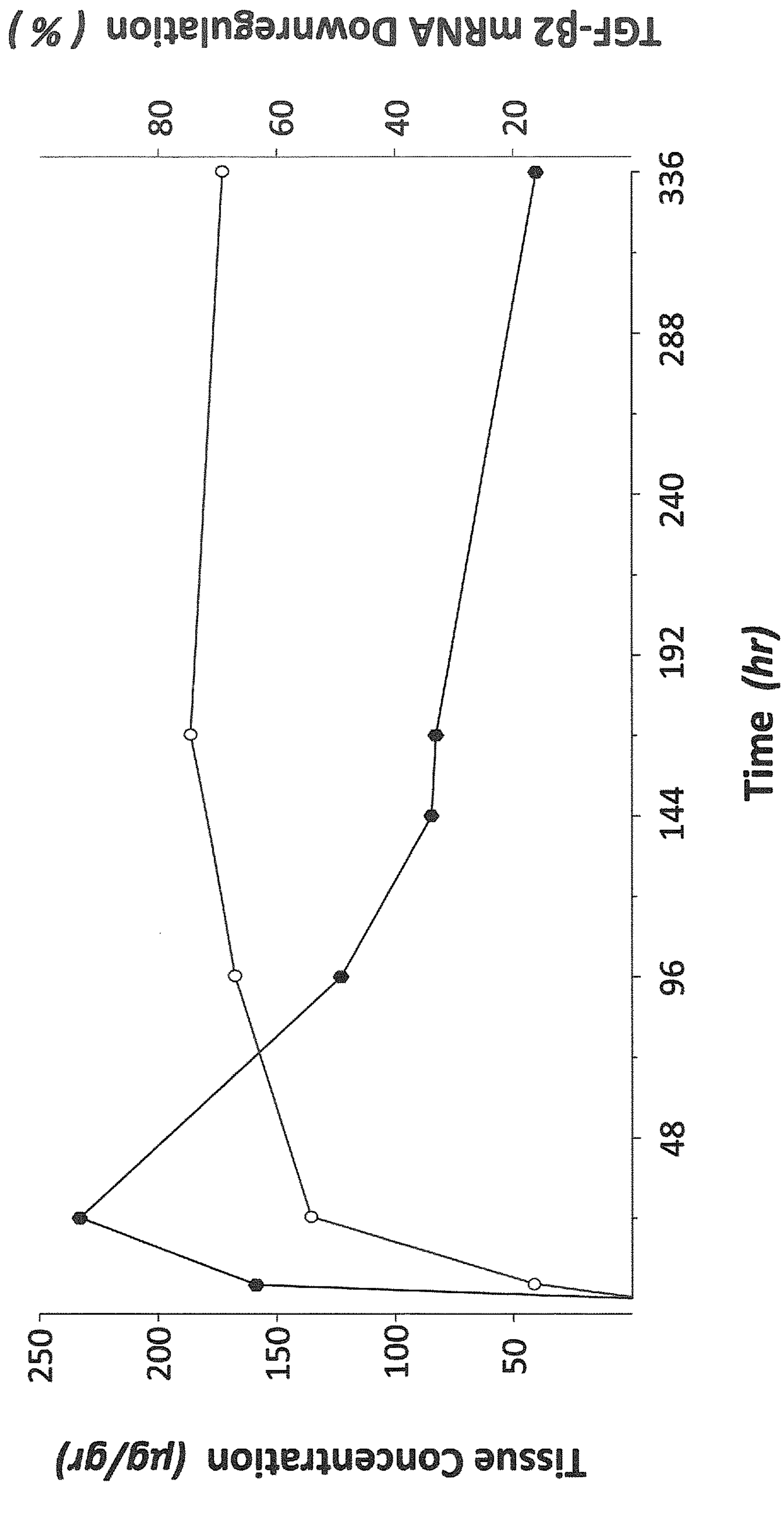

Fig. 31) TGF-β2 mRNA downregulation in established subcutaneous tumors (A-D) or kidney (E-F)
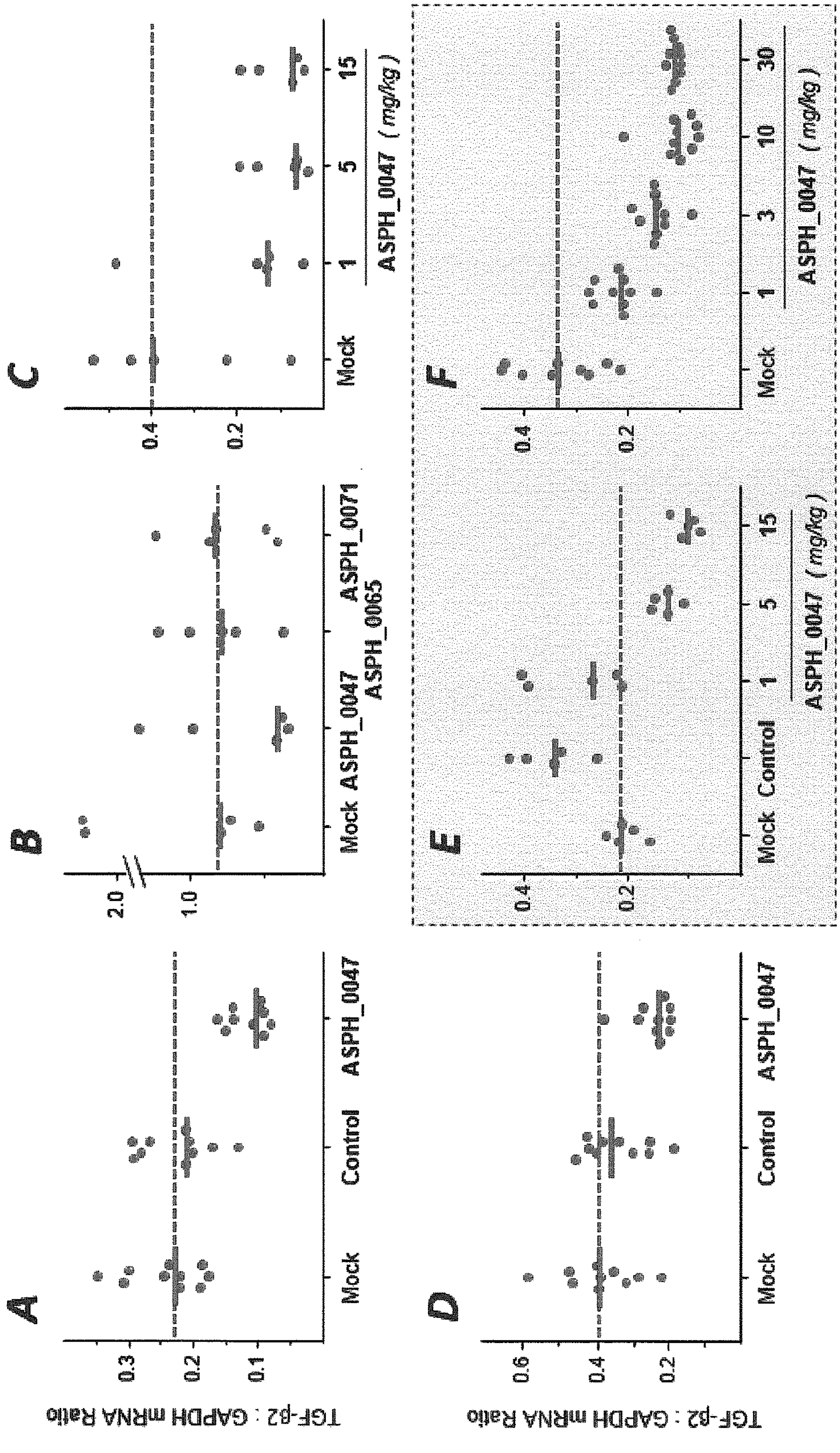

Fig. 32) Effect of systemic treatment of Balb/c mice with ASPH_0047 on lung metastasis in orthotopic and intravenous Renca models
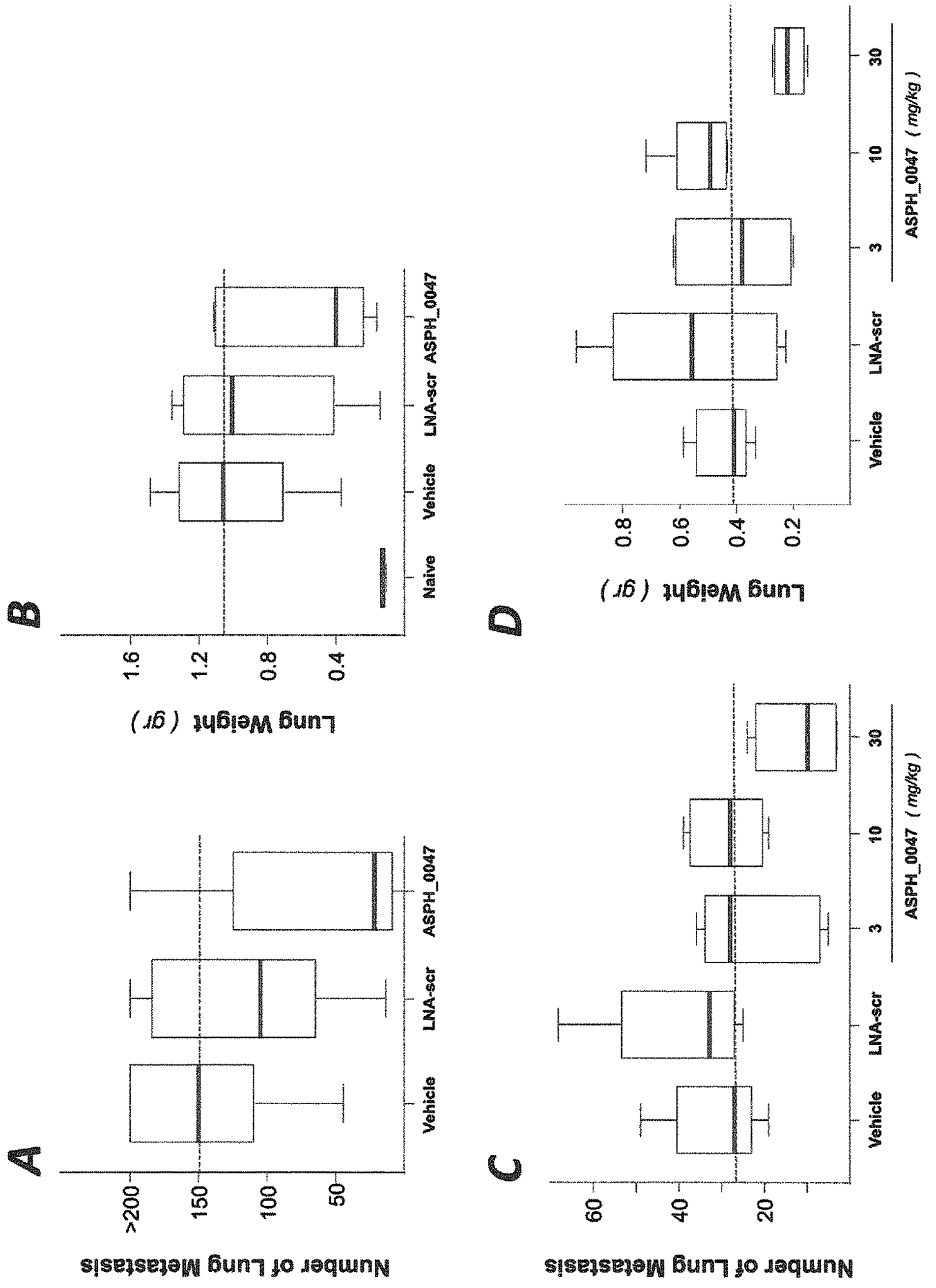

Fig. 33)
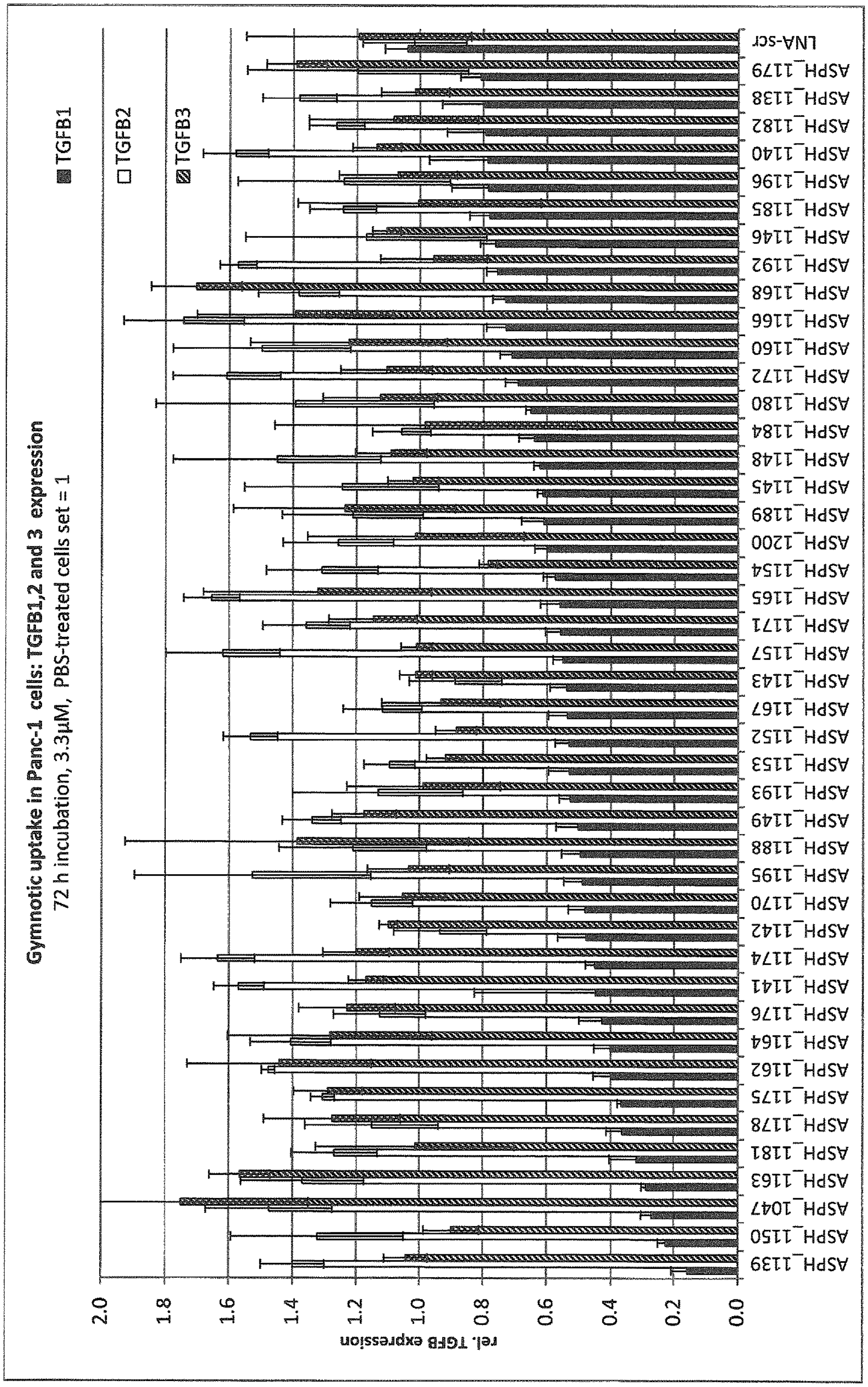

Fig. 34) Effect of systemic treatment of Balb/c mice with ASPH_0047 on lung metastasis in orthotopic mouse mammary carcinoma 4T1 model
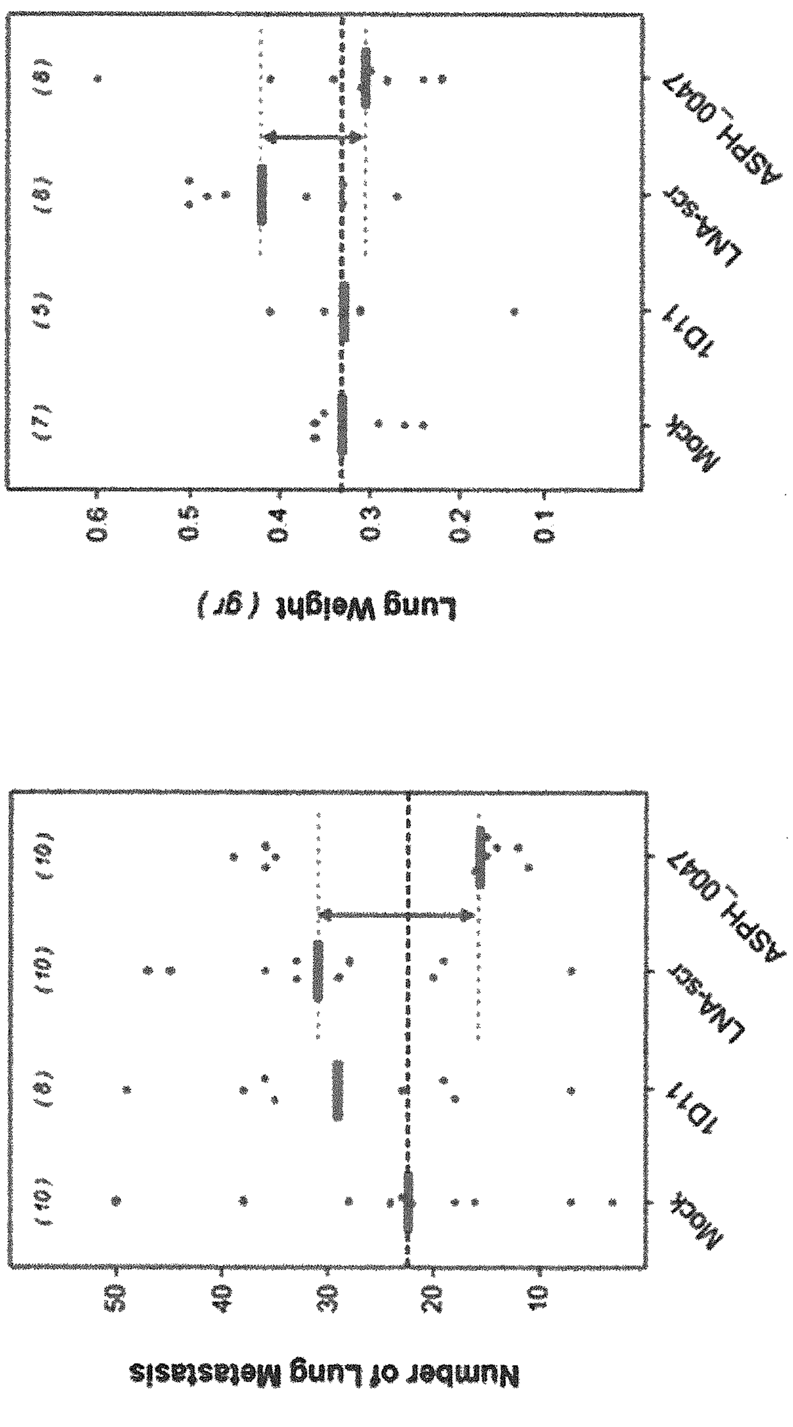

SEQUENCE LISTING

<160> NUMBER OF SEQ ID NOS: 417

<210> SEQ ID NO 1
<211> LENGTH: 2217
<212> TYPE: DNA
<213> ORGANISM: Homo sapiens

<400> SEQUENCE: 1

```
ccccgccgcc gccgcccttc gcgccctggg ccatctccct cccacctccc tccgcggagc     60
agccagacag cgagggcccc ggccgggggc aggggggacg ccccgtccgg ggcacccccc    120
cggctctgag ccgcccgcgg ggccggcctc ggcccggagc ggaggaagga gtcgccgagg    180
agcagcctga ggccccagag tctgagacga gccgccgccg cccccgccac tgcggggagg    240
agggggagga ggagcgggag gagggacgag ctggtcggga gaagaggaaa aaaacttttg    300
agacttttcc gttgccgctg ggagccggag gcgcggggac ctcttggcgc gacgctgccc    360
cgcgaggagg caggacttgg ggaccccaga ccgcctccct ttgccgccgg ggacgcttgc    420
tccctccctg ccccctacac ggcgtccctc aggcgccccc attccggacc agccctcggg    480
agtcgccgac ccggcctccc gcaaagactt ttccccagac ctcgggcgca ccccctgcac    540
gccgccttca tccccggcct gtctcctgag cccccgcgca tcctagaccc tttctcctcc    600
aggagacgga tctctctccg acctgccaca gatcccctat tcaagaccac ccaccttctg    660
gtaccagatc gcgcccatct aggttatttc cgtgggatac tgagacaccc ccggtccaag    720
cctcccctcc accactgcgc ccttctccct gaggacctca gctttccctc gaggccctcc    780
taccttttgc cgggagaccc ccagcccctg caggggcggg gcctccccac cacaccagcc    840
ctgttcgcgc tctcggcagt gccgggggc gccgcctccc ccatgccgcc ctccgggctg    900
cggctgctgc cgctgctgct accgctgctg tggctactgg tgctgacgcc tggccggccg    960
gccgcgggac tatccacctg caagactatc gacatggagc tggtgaagcg gaagcgcatc   1020
gaggccatcc gcggccagat cctgtccaag ctgcggctcg ccagcccccc gagccagggg   1080
gaggtgccgc ccggcccgct gcccgaggcc gtgctcgccc tgtacaacag cacccgcgac   1140
cgggtggccg gggagagtgc agaaccggag cccgagcctg aggccgacta ctacgccaag   1200
gaggtcaccc gcgtgctaat ggtggaaacc cacaacgaaa tctatgacaa gttcaagcag   1260
agtacacaca gcatatatat gttcttcaac acatcagagc tccgagaagc ggtacctgaa   1320
cccgtgttgc tctcccgggc agagctgcgt ctgctgaggc tcaagttaaa agtggagcag   1380
cacgtggagc tgtaccagaa atacagcaac aattcctggc gatacctcag caaccggctg   1440
ctggcaccca gcgactcgcc agagtggtta tcttttgatg tcaccggagt tgtgcggcag   1500
tggttgagcc gtggagggga aattgagggc tttcgcctta gcgcccactg ctcctgtgac   1560
agcagggata acacactgca agtggacatc aacgggttca ctaccggccg ccgaggtgac   1620
ctggccacca ttcatggcat gaaccggcct ttcctgcttc tcatggccac cccgctggag   1680
agggcccagc atctgcaaag ctcccggcac cgccgagccc tggacaccaa ctattgcttc   1740
agctccacgg agaagaactg ctgcgtgcgg cagctgtaca ttgacttccg caaggacctc   1800
ggctggaagt ggatccacga gcccaagggc taccatgcca acttctgcct cgggccctgc   1860
ccctacattt ggagcctgga cacgcagtac agcaaggtcc tggccctgta caaccagcat   1920
aacccgggcg cctcggcggc gccgtgctgc gtgccgcagg cgctggagcc gctgcccatc   1980
gtgtactacg tgggccgcaa gcccaaggtg gagcagctgt ccaacatgat cgtgcgctcc   2040
tgcaagtgca gctgaggtcc cgccccgccc cgccccgccc cggcaggccc ggccccaccc   2100
```

```
cgccccgccc ccgctgcctt gcccatgggg gctgtattta aggacacccg tgccccaagc   2160

ccacctgggg ccccattaaa gatggagaga ggactgcgga aaaaaaaaaa aaaaaaa      2217


<210> SEQ ID NO 2
<211> LENGTH: 5882
<212> TYPE: DNA
<213> ORGANISM: Homo sapiens

<400> SEQUENCE: 2

gtgatgttat ctgctggcag cagaaggttc gctccgagcg gagctccaga agctcctgac     60

aagagaaaga cagattgaga tagagataga aagagaaaga gagaaagaga cagcagagcg    120

agagcgcaag tgaaagaggc aggggagggg gatggagaat attagcctga cggtctaggg    180

agtcatccag gaacaaactg aggggctgcc cggctgcaga caggaggaga cagagaggat    240

ctattttagg gtggcaagtg cctacctacc ctaagcgagc aattccacgt tggggagaag    300

ccagcagagg ttgggaaagg gtgggagtcc aagggagccc ctgcgcaacc ccctcaggaa    360

taaaactccc cagccagggt gtcgcaaggg ctgccgttgt gatccgcagg gggtgaacgc    420

aaccgcgacg gctgatcgtc tgtggctggg ttggcgtttg gagcaagaga aggaggagca    480

ggagaaggag ggagctggag gctggaagcg tttgcaagcg gcggcggcag caacgtggag    540

taaccaagcg ggtcagcgcg cgcccgccag ggtgtaggcc acggagcgca gctcccagag    600

caggatccgc gccgcctcag cagcctctgc ggcccctgcg gcacccgacc gagtaccgag    660

cgccctgcga agcgcaccct cctccccgcg gtgcgctggg ctcgccccca gcgcgcgcac    720

acgcacacac acacacacac acacacacgc acgcacacac gtgtgcgctt ctctgctccg    780

gagctgctgc tgctcctgct ctcagcgccg cagtggaagg caggaccgaa ccgctccttc    840

tttaaatata taaatttcag cccaggtcag cctcggcggc ccccctcacc gcgctcccgg    900

cgcccctccc gtcagttcgc cagctgccag ccccgggacc ttttcatctc ttcccttttg    960

gccggaggag ccgagttcag atccgccact ccgcacccga gactgacaca ctgaactcca   1020

cttcctcctc ttaaatttat ttctacttaa tagccactcg tctctttttt tccccatctc   1080

attgctccaa gaattttttt cttcttactc gccaaagtca gggttccctc tgcccgtccc   1140

gtattaatat ttccactttt ggaactactg gccttttctt tttaaaggaa ttcaagcagg   1200

atacgttttt ctgttgggca ttgactagat tgtttgcaaa agtttcgcat caaaaacaac   1260

aacaacaaaa aaccaaacaa ctctccttga tctatacttt gagaattgtt gatttctttt   1320

ttttattctg acttttaaaa acaacttttt tttccacttt tttaaaaaat gcactactgt   1380

gtgctgagcg cttttctgat cctgcatctg gtcacggtcg cgctcagcct gtctacctgc   1440

agcacactcg atatggacca gttcatgcgc aagaggatcg aggcgatccg cgggcagatc   1500

ctgagcaagc tgaagctcac cagtccccca gaagactatc ctgagcccga ggaagtcccc   1560

ccggaggtga tttccatcta caacagcacc agggacttgc tccaggagaa ggcgagccgg   1620

agggcggccg cctgcgagcg cgagaggagc gacgaagagt actacgccaa ggaggtttac   1680

aaaatagaca tgccgccctt cttcccctcc gaaaatgcca tcccgcccac tttctacaga   1740

ccctacttca gaattgttcg atttgacgtc tcagcaatgg agaagaatgc ttccaatttg   1800

gtgaaagcag agttcagagt ctttcgtttg cagaacccaa aagccagagt gcctgaacaa   1860

cggattgagc tatatcagat tctcaagtcc aaagatttaa catctccaac ccagcgctac   1920

atcgacagca aagttgtgaa aacaagagca gaaggcgaat ggctctcctt cgatgtaact   1980
```

-continued

```
gatgctgttc atgaatggct tcaccataaa gacaggaacc tgggatttaa aataagctta   2040
cactgtccct gctgcacttt tgtaccatct aataattaca tcatcccaaa taaaagtgaa   2100
gaactagaag caagatttgc aggtattgat ggcacctcca catataccag tggtgatcag   2160
aaaactataa agtccactag gaaaaaaaac agtgggaaga ccccacatct cctgctaatg   2220
ttattgccct cctacagact tgagtcacaa cagaccaacc ggcggaagaa gcgtgctttg   2280
gatgcggcct attgctttag aaatgtgcag gataattgct gcctacgtcc actttacatt   2340
gatttcaaga gggatctagg gtggaaatgg atacacgaac ccaaagggta caatgccaac   2400
ttctgtgctg gagcatgccc gtatttatgg agttcagaca ctcagcacag cagggtcctg   2460
agcttatata ataccataaa tccagaagca tctgcttctc cttgctgcgt gtcccaagat   2520
ttagaacctc taaccattct ctactacatt ggcaaaacac ccaagattga acagctttct   2580
aatatgattg taaagtcttg caaatgcagc taaaattctt ggaaaagtgg caagaccaaa   2640
atgacaatga tgatgataat gatgatgacg acgacaacga tgatgcttgt aacaagaaaa   2700
cataagagag ccttggttca tcagtgttaa aaaatttttg aaaaggcggt actagttcag   2760
acactttgga agtttgtgtt ctgtttgtta aaactggcat ctgacacaaa aaaagttgaa   2820
ggccttattc tacatttcac ctactttgta agtgagagag acaagaagca aatttttttt   2880
aaagaaaaaa ataaacactg gaagaattta ttagtgttaa ttatgtgaac aacgacaaca   2940
acaacaacaa caacaaacag gaaaatccca ttaagtggag ttgctgtacg taccgttcct   3000
atcccgcgcc tcacttgatt tttctgtatt gctatgcaat aggcaccctt cccattctta   3060
ctcttagagt taacagtgag ttatttattg tgtgttacta tataatgaac gtttcattgc   3120
ccttggaaaa taaaacaggt gtataaagtg gagaccaaat actttgccag aaactcatgg   3180
atggcttaag gaacttgaac tcaaacgagc cagaaaaaaa gaggtcatat taatgggatg   3240
aaaacccaag tgagttatta tatgaccgag aaagtctgca ttaagataaa gaccctgaaa   3300
acacatgtta tgtatcagct gcctaaggaa gcttcttgta aggtccaaaa actaaaaaga   3360
ctgttaataa aagaaacttt cagtcagaat aagtctgtaa gttttttttt ttctttttaa   3420
ttgtaaatgg ttctttgtca gtttagtaaa ccagtgaaat gttgaaatgt tttgacatgt   3480
actggtcaaa cttcagacct taaaatattg ctgtatagct atgctatagg tttttttcctt   3540
tgttttggta tatgtaacca tacctatatt attaaaatag atggatatag aagccagcat   3600
aattgaaaac acatctgcag atctcttttg caaactatta aatcaaaaca ttaactactt   3660
tatgtgtaat gtgtaaattt ttaccatatt ttttatattc tgtaataatg tcaactatga   3720
tttagattga cttaaatttg ggctcttttt aatgatcact cacaaatgta tgtttctttt   3780
agctggccag tacttttgag taaagcccct atagtttgac ttgcactaca aatgcatttt   3840
tttttaata acatttgccc tacttgtgct ttgtgtttct ttcattatta tgacataagc   3900
tacctgggtc cacttgtctt ttcttttttt tgtttcacag aaaagatggg ttcgagttca   3960
gtggtcttca tcttccaagc atcattacta accaagtcag acgttaacaa atttttatgt   4020
taggaaaagg aggaatgtta tagatacata gaaaattgaa gtaaaatgtt ttcattttag   4080
caaggattta gggttctaac taaaactcag aatctttatt gagttaagaa aagtttctct   4140
accttggttt aatcaatatt tttgtaaaat cctattgtta ttacaaagag gacacttcat   4200
aggaaacatc tttttcttta gtcaggtttt taatattcag gggaaattg aaagatatat   4260
attttagtcg atttttcaaa aggggaaaaa agtccaggtc agcataagtc attttgtgta   4320
tttcactgaa gttataaggt ttttataaat gttctttgaa ggggaaaagg cacaagccaa   4380
```

-continued

```
tttttcctat gatcaaaaaa ttctttcttt cctctgagtg agagttatct atatctgagg   4440

ctaaagttta ccttgcttta ataaataatt tgccacatca ttgcagaaga ggtatcctca   4500

tgctggggtt aatagaatat gtcagtttat cacttgtcgc ttatttagct ttaaaataaa   4560

aattaatagg caaagcaatg gaatatttgc agtttcacct aaagagcagc ataaggaggc   4620

gggaatccaa agtgaagttg tttgatatgg tctacttctt ttttggaatt tcctgaccat   4680

taattaaaga attggatttg caagtttgaa aactggaaaa gcaagagatg ggatgccata   4740

atagtaaaca gcccttgtgt tggatgtaac ccaatcccag atttgagtgt gtgttgatta   4800

ttttttgtc ttccactttt ctattatgtg taaatcactt ttatttctgc agacattttc   4860

ctctcagata ggatgacatt ttgttttgta ttattttgtc tttcctcatg aatgcactga   4920

taatatttta aatgctctat tttaagatct cttgaatctg tttttttttt ttttaatttg   4980

ggggttctgt aaggtcttta tttcccataa gtaaatattg ccatgggagg ggggtggagg   5040

tggcaaggaa ggggtgaagt gctagtatgc aagtgggcag caattatttt tgtgttaatc   5100

agcagtacaa tttgatcgtt ggcatggtta aaaaatggaa tataagatta gctgttttgt   5160

attttgatga ccaattacgc tgtattttaa cacgatgtat gtctgttttt gtggtgctct   5220

agtggtaaat aaattatttc gatgatatgt ggatgtcttt ttcctatcag taccatcatc   5280

gagtctagaa aacacctgtg atgcaataag actatctcaa gctggaaaag tcataccacc   5340

tttccgattg ccctctgtgc tttctccctt aaggacagtc acttcagaag tcatgcttta   5400

aagcacaaga gtcaggccat atccatcaag gatagaagaa atccctgtgc cgtcttttta   5460

ttcccttatt tattgctatt tggtaattgt ttgagattta gtttccatcc agcttgactg   5520

ccgaccagaa aaaatgcaga gagatgtttg caccatgctt tggctttctg gttctatgtt   5580

ctgccaacgc cagggccaaa agaactggtc tagacagtat cccctgtagc cccataactt   5640

ggatagttgc tgagccagcc agatataaca agagccacgt gctttctggg gttggttgtt   5700

tgggatcagc tacttgcctg tcagtttcac tggtaccact gcaccacaaa caaaaaaacc   5760

caccctattt cctccaattt ttttggctgc tacctacaag accagactcc tcaaacgagt   5820

tgccaatctc ttaataaata ggattaataa aaaaagtaat tgtgactcaa aaaaaaaaaa   5880

aa                                                                  5882


<210> SEQ ID NO 3
<211> LENGTH: 3183
<212> TYPE: DNA
<213> ORGANISM: Homo sapiens

<400> SEQUENCE: 3

gacagaagca atggccgagg cagaagacaa gccgaggtgc tggtgaccct gggcgtctga     60

gtggatgatt ggggctgctg cgctcagagg cctgcctccc tgccttccaa tgcatataac    120

cccacacccc agccaatgaa gacgagaggc agcgtgaaca aagtcattta gaaagccccc    180

gaggaagtgt aaacaaaaga gaaagcatga atggagtgcc tgagagacaa gtgtgtcctg    240

tactgccccc acctttagct gggccagcaa ctgcccggcc ctgcttctcc ccacctactc    300

actggtgatc tttttttttt tacttttttt tccctttttct tttccattct cttttcttat    360

tttctttcaa ggcaaggcaa ggattttgat tttgggaccc agccatggtc cttctgcttc    420

ttctttaaaa tacccacttt ctccccatcg ccaagcggcg tttggcaata tcagatatcc    480

actctattta tttttaccta aggaaaaact ccagctccct tcccactccc agctgccttg    540
```

-continued

```
ccacccctcc cagccctctg cttgccctcc acctggcctg ctgggagtca gagcccagca    600
aaacctgttt agacacatgg acaagaatcc cagcgctaca aggcacacag tccgcttctt    660
cgtcctcagg gttgccagcg cttcctggaa gtcctgaagc tctcgcagtg cagtgagttc    720
atgcaccttc ttgccaagcc tcagtctttg ggatctgggg aggccgcctg gttttcctcc    780
ctccttctgc acgtctgctg gggtctcttc ctctccaggc cttgccgtcc ccctggcctc    840
tcttcccagc tcacacatga agatgcactt gcaaagggct ctggtggtcc tggccctgct    900
gaactttgcc acggtcagcc tctctctgtc cacttgcacc accttggact tcggccacat    960
caagaagaag agggtggaag ccattagggg acagatcttg agcaagctca ggctcaccag   1020
ccccccctgag ccaacggtga tgacccacgt ccccctatcag gtcctggccc tttacaacag   1080
cacccgggag ctgctggagg agatgcatgg ggagagggag gaaggctgca cccaggaaaa   1140
caccgagtcg gaatactatg ccaaagaaat ccataaattc gacatgatcc aggggctggc   1200
ggagcacaac gaactggctg tctgccctaa aggaattacc tccaaggttt tccgcttcaa   1260
tgtgtcctca gtggagaaaa atagaaccaa cctattccga gcagaattcc gggtcttgcg   1320
ggtgcccaac cccagctcta agcggaatga gcagaggatc gagctcttcc agatccttcg   1380
gccagatgag cacattgcca aacagcgcta tatcggtggc aagaatctgc ccacacgggg   1440
cactgccgag tggctgtcct ttgatgtcac tgacactgtg cgtgagtggc tgttgagaag   1500
agagtccaac ttaggtctag aaatcagcat tcactgtcca tgtcacacct ttcagcccaa   1560
tggagatatc ctggaaaaca ttcacgaggt gatggaaatc aaattcaaag gcgtggacaa   1620
tgaggatgac catggccgtg gagatctggg gcgcctcaag aagcagaagg atcaccacaa   1680
ccctcatcta atcctcatga tgattccccc acaccggctc gacaacccgg gccagggggg   1740
tcagaggaag aagcgggctt tggacaccaa ttactgcttc cgcaacttgg aggagaactg   1800
ctgtgtgcgc cccctctaca ttgacttccg acaggatctg ggctggaagt gggtccatga   1860
acctaagggc tactatgcca acttctgctc aggcccttgc ccatacctcc gcagtgcaga   1920
cacaacccac agcacggtgc tgggactgta caacactctg aaccctgaag catctgcctc   1980
gccttgctgc gtgccccagg acctggagcc cctgaccatc ctgtactatg ttgggaggac   2040
cccccaaagtg gagcagctct ccaacatggt ggtgaagtct tgtaaatgta gctgagaccc   2100
cacgtgcgac agagagaggg gagagagaac caccactgcc tgactgcccg ctcctcggga   2160
aacacacaag caacaaacct cactgagagg cctggagccc acaaccttcg gctccgggca   2220
aatggctgag atggaggttt ccttttggaa catttcttc ttgctggctc tgagaatcac   2280
ggtggtaaag aaagtgtggg tttggttaga ggaaggctga actcttcaga acacacagac   2340
tttctgtgac gcagacagag gggatgggga tagaggaaag ggatggtaag ttgagatgtt   2400
gtgtggcaat gggatttggg ctaccctaaa gggagaagga agggcagaga atggctgggt   2460
cagggccaga ctggaagaca cttcagatct gaggttggat ttgctcattg ctgtaccaca   2520
tctgctctag ggaatctgga ttatgttata caaggcaagc atttttttt tttttttaaa   2580
gacaggttac gaagacaaag tcccagaatt gtatctcata ctgtctggga ttaagggcaa   2640
atctattact tttgcaaact gtcctctaca tcaattaaca tcgtgggtca ctacagggag   2700
aaaatccagg tcatgcagtt cctggcccat caactgtatt gggccttttg gatatgctga   2760
acgcagaaga aagggtggaa atcaaccctc tcctgtctgc cctctgggtc cctcctctca   2820
cctctccctc gatcatattt ccccttggac acttggttag acgccttcca ggtcaggatg   2880
cacatttctg gattgtggtt ccatgcagcc ttggggcatt atgggttctt cccccacttc   2940
```

ccctccaaga ccctgtgttc atttggtgtt cctggaagca ggtgctacaa catgtgaggc 3000
attcggggaa gctgcacatg tgccacacag tgacttggcc ccagacgcat agactgaggt 3060
ataaagacaa gtatgaatat tactctcaaa atctttgtat aaataaatat ttttggggca 3120
tcctggatga tttcatcttc tggaatattg tttctagaac agtaaaagcc ttattctaag 3180
gtg 3183

<210> SEQ ID NO 4
<211> LENGTH: 10
<212> TYPE: DNA
<213> ORGANISM: Artificial Sequence
<220> FEATURE:
<223> OTHER INFORMATION: filler to provide correct SEQ ID numbering

<400> SEQUENCE: 4
aaaaaaaaaa 10

<210> SEQ ID NO 5
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 5
gaccagatgc agga 14

<210> SEQ ID NO 6
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 6
gcgaccgtga ccagat 16

<210> SEQ ID NO 7
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 7
gcgcgaccgt gacc 14

<210> SEQ ID NO 8
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 8
agcgcgaccg tga 13

<210> SEQ ID NO 9
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 9
gaccgtgacc agat 14

<210> SEQ ID NO 10
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 10
ctgcccgcgg at 12

<210> SEQ ID NO 11
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 11
tctgcccgcg gat 13

<210> SEQ ID NO 12
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 12
ggatctgccc gcgga 15

<210> SEQ ID NO 13
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 13
cttgctcagg atctgcc 17

<210> SEQ ID NO 14
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 14
gctcaggatc tgcccgcgga 20

<210> SEQ ID NO 15
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 15
ggatcgcctc gat 13

<210> SEQ ID NO 16
<211> LENGTH: 12

<212> TYPE: DNA
<213> ORGANISM: Artificial Sequence
<220> FEATURE:
<223> OTHER INFORMATION: modified TGF-beta2 oligonucleotide

<400> SEQUENCE: 16
ccgcggatcg cc 12

<210> SEQ ID NO 17
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 17
acctccttgg cgtagta 17

<210> SEQ ID NO 18
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 18
cctccttggc gtagta 16

<210> SEQ ID NO 19
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 19
ctccttggcg tagta 15

<210> SEQ ID NO 20
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 20
tccttggcgt agta 14

<210> SEQ ID NO 21
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 21
cagaagttgg cat 13

<210> SEQ ID NO 22
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 22
aagtgggcgg gat 13

<210> SEQ ID NO 23
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 23
gcgggatggc at 12

<210> SEQ ID NO 24
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 24
gaaatcacct ccg 13

<210> SEQ ID NO 25
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 25
aagtgggcgg gat 13

<210> SEQ ID NO 26
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 26
tgtagcgctg ggt 13

<210> SEQ ID NO 27
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 27
cgaaggagag cca 13

<210> SEQ ID NO 28
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 28
tcgcgctcgc aggc 14

<210> SEQ ID NO 29
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 29
aagtgggcgg gatg 14

<210> SEQ ID NO 30
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 30
atgtagcgct gggt 14

<210> SEQ ID NO 31
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 31
cgaaggagag ccat 14

<210> SEQ ID NO 32
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 32
gaaagtgggc gggat 15

<210> SEQ ID NO 33
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 33
cgaaggagag ccatt 15

<210> SEQ ID NO 34
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 34
cgatcctctt gcgcat 16

<210> SEQ ID NO 35
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 35
aagtgggcgg gatggc 16

<210> SEQ ID NO 36
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 36
gatggaaatc acctccg 17

<210> SEQ ID NO 37
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 37
aaacctcctt ggcgtag 17

<210> SEQ ID NO 38
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 38
tagaaagtgg gcgggat 17

<210> SEQ ID NO 39
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 39
ggcgggatgg cat 13

<210> SEQ ID NO 40
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 40
gggtctgtag aaagtg 16

<210> SEQ ID NO 41
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 41
gaaggagagc cattc 15

<210> SEQ ID NO 42
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 42
ccaggttcct gtctt 15

<210> SEQ ID NO 43
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 43
tctgatcacc actgg 15

<210> SEQ ID NO 44
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 44
tttctgatca ccactgg 17

<210> SEQ ID NO 45
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 45
gtctgtagga gggca 15

<210> SEQ ID NO 46
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 46
agtctgtagg agggca 16

<210> SEQ ID NO 47
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 47
tctgtaggag ggc 13

<210> SEQ ID NO 48
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 48
cagatgccag ttttaac 17

<210> SEQ ID NO 49

-continued

<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 49
caaagtattt ggtctcc 17

<210> SEQ ID NO 50
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 50
ccttaagcca tccatga 17

<210> SEQ ID NO 51
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 51
gtactggcca gctaa 15

<210> SEQ ID NO 52
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 52
gcctcgatcc tcttgcgcat 20

<210> SEQ ID NO 53
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 53
aaacctcctt ggcgtagtac 20

<210> SEQ ID NO 54
<211> LENGTH: 20
<212> TYPE: DNA
<213> ORGANISM: Artificial Sequence
<220> FEATURE:
<223> OTHER INFORMATION: modified TGF-beta2 oligonucleotide

<400> SEQUENCE: 54
gaaagtgggc gggatggcat 20

<210> SEQ ID NO 55
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 55
gaattgctcg cttaggg 17

<210> SEQ ID NO 56
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 56
cgtcgcggtt gcgttca 17

<210> SEQ ID NO 57
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 57
cgtggcctac accctgg 17

<210> SEQ ID NO 58
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 58
ttctaaagca ataggcc 17

<210> SEQ ID NO 59
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 59
agaatggtta gaggttc 17

<210> SEQ ID NO 60
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 60
tctgaactag taccgcc 17

<210> SEQ ID NO 61
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 61
cccattaata tgacctc 17

<210> SEQ ID NO 62
<211> LENGTH: 17
<212> TYPE: DNA

<213> ORGANISM: Artificial Sequence
<220> FEATURE:
<223> OTHER INFORMATION: modified TGF-beta2 oligonucleotide

<400> SEQUENCE: 62
tttagttaga accctaa 17

<210> SEQ ID NO 63
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 63
cctcagatat agataac 17

<210> SEQ ID NO 64
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 64
tactattatg gcatccc 17

<210> SEQ ID NO 65
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 65
tgcccacttg catacta 17

<210> SEQ ID NO 66
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 66
agcgtaattg gtcatca 17

<210> SEQ ID NO 67
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 67
cgttggcaga acataga 17

<210> SEQ ID NO 68
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 68
gggatactgt ctagacc 17

-continued

<210> SEQ ID NO 69
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 69
attggcaact cgtttga 17

<210> SEQ ID NO 70
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 70
cgtcaggcta atattc 16

<210> SEQ ID NO 71
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 71
ggatgactcc ctagac 16

<210> SEQ ID NO 72
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 72
gtcgcggttg cgttca 16

<210> SEQ ID NO 73
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 73
ctcggtactc ggtcgg 16

<210> SEQ ID NO 74
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 74
ggttcggtcc tgcctt 16

<210> SEQ ID NO 75
<211> LENGTH: 16
<212> TYPE: DNA
<213> ORGANISM: Artificial Sequence
<220> FEATURE:

<223> OTHER INFORMATION: modified TGF-beta2 oligonucleotide

<400> SEQUENCE: 75
aataggccgc atccaa 16

<210> SEQ ID NO 76
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 76
aactagtacc gccttt 16

<210> SEQ ID NO 77
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 77
tcggtcatat aataac 16

<210> SEQ ID NO 78
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 78
agaccgtcag gctaa 15

<210> SEQ ID NO 79
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 79
gtcgcggttg cgttc 15

<210> SEQ ID NO 80
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 80
ttccactgcg gcgct 15

<210> SEQ ID NO 81
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 81
aaggagcggt tcggt 15

<210> SEQ ID NO 82
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 82
ctcgggtgcg gagtg 15

<210> SEQ ID NO 83
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 83
ctgactttgg cgagt 15

<210> SEQ ID NO 84
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 84
gataggaacg gtacg 15

<210> SEQ ID NO 85
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 85
cactttggat tcccg 15

<210> SEQ ID NO 86
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 86
gtcgcggttg cgtt 14

<210> SEQ ID NO 87
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 87
tacaccctgg cggg 14

<210> SEQ ID NO 88
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 88
ctcggtactc ggtc 14

<210> SEQ ID NO 89
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 89
aggagcggtt cggt 14

<210> SEQ ID NO 90
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 90
gtctcgggtg cgga 14

<210> SEQ ID NO 91
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 91
tacgggacgg gcag 14

<210> SEQ ID NO 92
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 92
cgtcgctcct ctcg 14

<210> SEQ ID NO 93
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 93
tagcgctggg ttgg 14

<210> SEQ ID NO 94
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 94
aagcaatagg ccgc 14

<210> SEQ ID NO 95
<211> LENGTH: 14

<212> TYPE: DNA
<213> ORGANISM: Artificial Sequence
<220> FEATURE:
<223> OTHER INFORMATION: modified TGF-beta2 oligonucleotide

<400> SEQUENCE: 95
tacgggcatg ctcc 14

<210> SEQ ID NO 96
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 96
aggcgcggga tagg 14

<210> SEQ ID NO 97
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 97
tttggattcc cgcc 14

<210> SEQ ID NO 98
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 98
accactagag cacc 14

<210> SEQ ID NO 99
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 99
gcgttggcag aaca 14

<210> SEQ ID NO 100
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 100
ttgctcgctt agg 13

<210> SEQ ID NO 101
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 101

-continued gtcgcggttg cgt 13

<210> SEQ ID NO 102
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 102
ggcgctcggt act 13

<210> SEQ ID NO 103
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 103
atctgaactc ggc 13

<210> SEQ ID NO 104
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 104
cggttggtct gtt 13

<210> SEQ ID NO 105
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 105
tccaccctag atc 13

<210> SEQ ID NO 106
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 106
ctagtaccgc ctt 13

<210> SEQ ID NO 107
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 107
ggtcggcagt caa 13

<210> SEQ ID NO 108
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 108
cttgcgacac cc 12

<210> SEQ ID NO 109
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 109
gagcggttcg gt 12

<210> SEQ ID NO 110
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 110
acacagtagt gcat 14

<210> SEQ ID NO 111
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 111
gggtctgtag aaag 14

<210> SEQ ID NO 112
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 112
ggttggagat gtta 14

<210> SEQ ID NO 113
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 113
tgggttggag atgt 14

<210> SEQ ID NO 114
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 114
gctgggttgg agat 14

<210> SEQ ID NO 115
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 115
gcgctgggtt ggag 14

<210> SEQ ID NO 116
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 116
agcgctgggt tgga 14

<210> SEQ ID NO 117
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 117
tagcgctggg ttgg 14

<210> SEQ ID NO 118
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 118
gtagcgctgg gttg 14

<210> SEQ ID NO 119
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 119
gatgtagcgc tggg 14

<210> SEQ ID NO 120
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 120
ccattcgcct tctg 14

<210> SEQ ID NO 121
<211> LENGTH: 14
<212> TYPE: DNA
<213> ORGANISM: Artificial Sequence
<220> FEATURE:
<223> OTHER INFORMATION: modified TGF-beta2 oligonucleotide -continued

<400> SEQUENCE: 121
gagagccatt cgcc 14

<210> SEQ ID NO 122
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 122
agcagggaca gtgt 14

<210> SEQ ID NO 123
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 123
gcaggagatg tggg 14

<210> SEQ ID NO 124
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 124
cggttggtct gttg 14

<210> SEQ ID NO 125
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 125
ccggttggtc tgtt 14

<210> SEQ ID NO 126
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 126
gccggttggt ctgt 14

<210> SEQ ID NO 127
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 127
agttggcatt gtac 14

<210> SEQ ID NO 128

<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 128
ggttagaggt tcta 14

<210> SEQ ID NO 129
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 129
atggttagag gttc 14

<210> SEQ ID NO 130
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 130
agaatggtta gagg 14

<210> SEQ ID NO 131
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 131
agagaatggt taga 14

<210> SEQ ID NO 132
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 132
cgttgtcgtc gtca 14

<210> SEQ ID NO 133
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 133
accaaggctc tctt 14

<210> SEQ ID NO 134
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 134
gcttcttgtc tctc 14

<210> SEQ ID NO 135
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 135
ggaacggtac gtac 14

<210> SEQ ID NO 136
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 136
taggaacggt acgt 14

<210> SEQ ID NO 137
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 137
gggataggaa cggt 14

<210> SEQ ID NO 138
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 138
cgcgggatag gaac 14

<210> SEQ ID NO 139
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 139
aggcgcggga tagg 14

<210> SEQ ID NO 140
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 140
gtcaagctgg atgg 14

<210> SEQ ID NO 141
<211> LENGTH: 13
<212> TYPE: DNA

<213> ORGANISM: Artificial Sequence
<220> FEATURE:
<223> OTHER INFORMATION: modified TGF-beta2 oligonucleotide

<400> SEQUENCE: 141
tctgtaggag ggc 13

<210> SEQ ID NO 142
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 142
gaccagatgc agga 14

<210> SEQ ID NO 143
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 143
ctccttggcg tagta 15

<210> SEQ ID NO 144
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 144
cctccttggc gtagta 16

<210> SEQ ID NO 145
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 145
cagatgccag ttttaac 17

<210> SEQ ID NO 146
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 146
agcgtaattg gtcatca 17

<210> SEQ ID NO 147
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 147
agtatttggt ctcc 14

<210> SEQ ID NO 148
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 148
aagtatttgg tctc 14

<210> SEQ ID NO 149
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 149
caaagtattt ggtctcc 17

<210> SEQ ID NO 150
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 150
aagtatttgg tctcc 15

<210> SEQ ID NO 151
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 151
agctcgtccc tcctccc 17

<210> SEQ ID NO 152
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 152
gagggctggt ccggaat 17

<210> SEQ ID NO 153
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 153
cgagggctgg tccggaa 17

<210> SEQ ID NO 154
<211> LENGTH: 17
<212> TYPE: DNA
<213> ORGANISM: Artificial Sequence
<220> FEATURE:

<223> OTHER INFORMATION: modified TGF-beta1 oligonucleotide

<400> SEQUENCE: 154
gagggcggca tggggga 17

<210> SEQ ID NO 155
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 155
gcgggtgctg ttgtaca 17

<210> SEQ ID NO 156
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 156
cgcgggtgct gttgtac 17

<210> SEQ ID NO 157
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 157
gtcgcgggtg ctgttgt 17

<210> SEQ ID NO 158
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 158
ggtcgcgggt gctgttg 17

<210> SEQ ID NO 159
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 159
ccggtcgcgg gtgctgt 17

<210> SEQ ID NO 160
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 160
cccggtcgcg ggtgctg 17

<210> SEQ ID NO 161
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 161
agcacgcggg tgacctc 17

<210> SEQ ID NO 162
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 162
ttagcacgcg ggtgacc 17

<210> SEQ ID NO 163
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 163
gggctcgtgg atccact 17

<210> SEQ ID NO 164
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 164
ccttgggctc gtggatc 17

<210> SEQ ID NO 165
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 165
tggcatggta gcccttg 17

<210> SEQ ID NO 166
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 166
cgagggctgg tccgga 16

<210> SEQ ID NO 167
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 167
gcgggtgctg ttgtac 16

<210> SEQ ID NO 168
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 168
gcacgcgggt gacctc 16

<210> SEQ ID NO 169
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 169
ccttgggctc gtggat 16

<210> SEQ ID NO 170
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 170
ggcatggtag cccttg 16

<210> SEQ ID NO 171
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 171
gggtgctgtt gtac 14

<210> SEQ ID NO 172
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 172
tcgcgggtgc tgtt 14

<210> SEQ ID NO 173
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 173
gtcgcgggtg ctgt 14

<210> SEQ ID NO 174
<211> LENGTH: 14

<212> TYPE: DNA
<213> ORGANISM: Artificial Sequence
<220> FEATURE:
<223> OTHER INFORMATION: modified TGF-beta1 oligonucleotide

<400> SEQUENCE: 174
ctcgtggatc cact 14

<210> SEQ ID NO 175
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 175
atggtagccc ttgg 14

<210> SEQ ID NO 176
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 176
tggcatggta gccc 14

<210> SEQ ID NO 177
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 177
gaagttggca tggt 14

<210> SEQ ID NO 178
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 178
tcgcgggtgc tgt 13

<210> SEQ ID NO 179
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 179
cacccggtcg cgg 13

<210> SEQ ID NO 180
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 180
ccacccggtc gcg 13

<210> SEQ ID NO 181
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 181
cgccaggaat tgt 13

<210> SEQ ID NO 182
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 182
ggctcgtgga tcc 13

<210> SEQ ID NO 183
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 183
tgggctcgtg gat 13

<210> SEQ ID NO 184
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 184
gcatggtagc cct 13

<210> SEQ ID NO 185
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 185
agttggcatg gta 13

<210> SEQ ID NO 186
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 186
ttgcaggagc gca 13

<210> SEQ ID NO 187
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 187
attagcacgc gggtgac 17

<210> SEQ ID NO 188
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 188
accattagca cgcgggt 17

<210> SEQ ID NO 189
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 189
caccattagc acgcggg 17

<210> SEQ ID NO 190
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 190
ccaccattag cacgcgg 17

<210> SEQ ID NO 191
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 191
tccaccatta gcacgcg 17

<210> SEQ ID NO 192
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 192
tccaccttgg gcttgcg 17

<210> SEQ ID NO 193
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 193
ttagcacgcg ggtgac 16

<210> SEQ ID NO 194
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 194
accattagca cgcggg 16

<210> SEQ ID NO 195
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 195
caccattagc acgcgg 16

<210> SEQ ID NO 196
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 196
caccattagc acgcg 15

<210> SEQ ID NO 197
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 197
gcggcacgca gcacg 15

<210> SEQ ID NO 198
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 198
tcgatgcgct tccg 14

<210> SEQ ID NO 199
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 199
tagcacgcgg gtga 14

<210> SEQ ID NO 200
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 200
attagcacgc gggt 14

<210> SEQ ID NO 201
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 201
cattagcacg cggg 14

<210> SEQ ID NO 202
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 202
accattagca cgcg 14

<210> SEQ ID NO 203
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 203
caccattagc acgc 14

<210> SEQ ID NO 204
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 204
ccaccattag cacg 14

<210> SEQ ID NO 205
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 205
tccaccatta gcac 14

<210> SEQ ID NO 206
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 206
gaccttgctg tact 14

<210> SEQ ID NO 207

<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 207
ggaccttgct gtac 14

<210> SEQ ID NO 208
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 208
aggaccttgc tgta 14

<210> SEQ ID NO 209
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 209
cggcacgcag cacg 14

<210> SEQ ID NO 210
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 210
accttgggct tgcg 14

<210> SEQ ID NO 211
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 211
ttagcacgcg ggt 13

<210> SEQ ID NO 212
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 212
accattagca cgc 13

<210> SEQ ID NO 213
<211> LENGTH: 13
<212> TYPE: DNA
<213> ORGANISM: Artificial Sequence
<220> FEATURE:
<223> OTHER INFORMATION: modified TGF-beta1 oligonucleotide

<400> SEQUENCE: 213
cggcacgcag cac 13

<210> SEQ ID NO 214
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 214
caccagctcc atgtcga 17

<210> SEQ ID NO 215
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 215
tcgcgggtgc tgttgta 17

<210> SEQ ID NO 216
<211> LENGTH: 17
<212> TYPE: DNA
<213> ORGANISM: Artificial Sequence
<220> FEATURE:
<223> OTHER INFORMATION: modified TGF-beta1 oligonucleotide

<400> SEQUENCE: 216
gtgtccaggc tccaaat 17

<210> SEQ ID NO 217
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 217
gctcgtccct cctccc 16

<210> SEQ ID NO 218
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 218
accagctcgt ccctcc 16

<210> SEQ ID NO 219
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 219
ggaggccccg cccctg 16

<210> SEQ ID NO 220
<211> LENGTH: 16
<212> TYPE: DNA

-continued

<213> ORGANISM: Artificial Sequence
<220> FEATURE:
<223> OTHER INFORMATION: modified TGF-beta1 oligonucleotide

<400> SEQUENCE: 220
catgggggag gcggcg 16

<210> SEQ ID NO 221
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 221
accagctcca tgtcga 16

<210> SEQ ID NO 222
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 222
ggtcgcgggt gctgtt 16

<210> SEQ ID NO 223
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 223
ggaccttgct gtactg 16

<210> SEQ ID NO 224
<211> LENGTH: 16
<212> TYPE: DNA
<213> ORGANISM: Artificial Sequence
<220> FEATURE:
<223> OTHER INFORMATION: modified TGF-beta1 oligonucleotide

<400> SEQUENCE: 224
tccaccttgg gcttgc 16

<210> SEQ ID NO 225
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 225
agctcgtccc tcctc 15

<210> SEQ ID NO 226
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 226
ccagctcgtc cctcc 15

<210> SEQ ID NO 227
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 227
gagggctggt ccgga 15

<210> SEQ ID NO 228
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 228
tcccgagggc tggtc 15

<210> SEQ ID NO 229
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 229
cggcatgggg gaggc 15

<210> SEQ ID NO 230
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 230
cagctccatg tcgat 15

<210> SEQ ID NO 231
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 231
accagctcca tgtcg 15

<210> SEQ ID NO 232
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 232
tcgcgggtgc tgttg 15

<210> SEQ ID NO 233
<211> LENGTH: 15
<212> TYPE: DNA
<213> ORGANISM: Artificial Sequence
<220> FEATURE:

<223> OTHER INFORMATION: modified TGF-beta1 oligonucleotide

<400> SEQUENCE: 233
gtcgcgggtg ctgtt 15

<210> SEQ ID NO 234
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 234
ggtcgcgggt gctgt 15

<210> SEQ ID NO 235
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 235
agcacgcggg tgacc 15

<210> SEQ ID NO 236
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 236
tagcacgcgg gtgac 15

<210> SEQ ID NO 237
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 237
cattagcacg cgggt 15

<210> SEQ ID NO 238
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 238
tccaccatta gcacg 15

<210> SEQ ID NO 239
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 239
ccaggaattg ttgct 15

<210> SEQ ID NO 240
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 240
ttgggctcgt ggatc 15

<210> SEQ ID NO 241
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 241
cttgggctcg tggat 15

<210> SEQ ID NO 242
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 242
ttggcatggt agccc 15

<210> SEQ ID NO 243
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 243
gaagttggca tggta 15

<210> SEQ ID NO 244
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 244
agaagttggc atggt 15

<210> SEQ ID NO 245
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 245
tgtccaggct ccaaa 15

<210> SEQ ID NO 246
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 246
aggaccttgc tgtac 15

<210> SEQ ID NO 247
<211> LENGTH: 15
<212> TYPE: DNA
<213> ORGANISM: Artificial Sequence
<220> FEATURE:
<223> OTHER INFORMATION: modified TGF-beta1 oligonucleotide

<400> SEQUENCE: 247
caccttgggc ttgcg 15

<210> SEQ ID NO 248
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 248
agctcgtccc tcct 14

<210> SEQ ID NO 249
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 249
cagctcgtcc ctcc 14

<210> SEQ ID NO 250
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 250
accagctcgt ccct 14

<210> SEQ ID NO 251
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 251
cccgagggct ggtc 14

<210> SEQ ID NO 252
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 252
gcggcatggg ggag 14

<210> SEQ ID NO 253
<211> LENGTH: 14

<212> TYPE: DNA
<213> ORGANISM: Artificial Sequence
<220> FEATURE:
<223> OTHER INFORMATION: modified TGF-beta1 oligonucleotide

<400> SEQUENCE: 253
gtcttgcagg tgga 14

<210> SEQ ID NO 254
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 254
tcgatgcgct tccg 14

<210> SEQ ID NO 255
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 255
ggacaggatc tggc 14

<210> SEQ ID NO 256
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 256
acctccccct ggct 14

<210> SEQ ID NO 257
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 257
accattagca cgcg 14

<210> SEQ ID NO 258
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 258
cagcagttct tctc 14

<210> SEQ ID NO 259
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 259
tacagctgcc gcac 14

<210> SEQ ID NO 260
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 260
agttggcatg gtag 14

<210> SEQ ID NO 261
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 261
aagttggcat ggta 14

<210> SEQ ID NO 262
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 262
gaagttggca tggt 14

<210> SEQ ID NO 263
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 263
tccaggctcc aaat 14

<210> SEQ ID NO 264
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 264
accttgctgt actg 14

<210> SEQ ID NO 265
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 265
ttgcaggagc gcac 14

<210> SEQ ID NO 266
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 266
gcagaagttg gcat 14

<210> SEQ ID NO 267
<211> LENGTH: 14
<212> TYPE: DNA
<213> ORGANISM: Artificial Sequence
<220> FEATURE:
<223> OTHER INFORMATION: modified TGF-beta1 oligonucleotide

<400> SEQUENCE: 267
cgggtgctgt tgta 14

<210> SEQ ID NO 268
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 268
cccagcggca acggaaa 17

<210> SEQ ID NO 269
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 269
caagaggtcc ccgcgcc 17

<210> SEQ ID NO 270
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 270
gcgtccccgg cggcaaa 17

<210> SEQ ID NO 271
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 271
ggtcggcgac tcccgag 17

<210> SEQ ID NO 272
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 272
tcggagagag atccgtc 17

<210> SEQ ID NO 273
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 273
atcccacgga aataacc 17

<210> SEQ ID NO 274
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 274
ctcagtatcc cacggaa 17

<210> SEQ ID NO 275
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 275
actgccgaga gcgcgaa 17

<210> SEQ ID NO 276
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 276
ctgatgtgtt gaagaac 17

<210> SEQ ID NO 277
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 277
tgaggtatcg ccaggaa 17

<210> SEQ ID NO 278
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 278
actgccgcac aactccg 17

<210> SEQ ID NO 279
<211> LENGTH: 17
<212> TYPE: DNA
<213> ORGANISM: Artificial Sequence
<220> FEATURE:
<223> OTHER INFORMATION: modified TGF-beta oligonucleotide

<400> SEQUENCE: 279
cggcccacgt agtacac 17

<210> SEQ ID NO 280
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 280
cccagcggca acggaa 16

<210> SEQ ID NO 281
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 281
tcgcgccaag aggtcc 16

<210> SEQ ID NO 282
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 282
ggtcggcgac tcccga 16

<210> SEQ ID NO 283
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 283
gtcggagaga gatccg 16

<210> SEQ ID NO 284
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 284
tcagtatccc acggaa 16

<210> SEQ ID NO 285
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 285
cgagagcgcg aacagg 16

<210> SEQ ID NO 286

<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 286
actgccgaga gcgcga 16

<210> SEQ ID NO 287
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 287
ggcgtcagca ccagta 16

<210> SEQ ID NO 288
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 288
ggtttccacc attagc 16

<210> SEQ ID NO 289
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 289
gaggtatcgc caggaa 16

<210> SEQ ID NO 290
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 290
aaccactgcc gcacaa 16

<210> SEQ ID NO 291
<211> LENGTH: 16
<212> TYPE: DNA
<213> ORGANISM: Artificial Sequence
<220> FEATURE:
<223> OTHER INFORMATION: modified TGF-beta oligonucleotide

<400> SEQUENCE: 291
cggcccacgt agtaca 16

<210> SEQ ID NO 292
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 292
cggcggctcg tctca 15

<210> SEQ ID NO 293
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 293
cccagcggca acgga 15

<210> SEQ ID NO 294
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 294
tcgcgccaag aggtc 15

<210> SEQ ID NO 295
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 295
cgtcgcgcca agagg 15

<210> SEQ ID NO 296
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 296
ggagcaagcg tcccc 15

<210> SEQ ID NO 297
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 297
gtgcgcccga ggtct 15

<210> SEQ ID NO 298
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 298
gtctaggatg cgcgg 15

<210> SEQ ID NO 299
<211> LENGTH: 15
<212> TYPE: DNA

<213> ORGANISM: Artificial Sequence
<220> FEATURE:
<223> OTHER INFORMATION: modified TGF-beta oligonucleotide

<400> SEQUENCE: 299
cagtatccca cggaa 15

<210> SEQ ID NO 300
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 300
ccgagagcgc gaaca 15

<210> SEQ ID NO 301
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 301
ggcgtcagca ccagt 15

<210> SEQ ID NO 302
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 302
gttgctgagg tatcg 15

<210> SEQ ID NO 303
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 303
accactgccg cacaa 15

<210> SEQ ID NO 304
<211> LENGTH: 15
<212> TYPE: DNA
<213> ORGANISM: Artificial Sequence
<220> FEATURE:
<223> OTHER INFORMATION: modified TGF-beta oligonucleotide

<400> SEQUENCE: 304
cggcccacgt agtac 15

<210> SEQ ID NO 305
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 305
ctcggcgact cctt 14

<210> SEQ ID NO 306
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 306
agcggcaacg gaaa 14

<210> SEQ ID NO 307
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 307
tcgcgccaag aggt 14

<210> SEQ ID NO 308
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 308
tccccggcgg caaa 14

<210> SEQ ID NO 309
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 309
tgcgcccgag gtct 14

<210> SEQ ID NO 310
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 310
gtctaggatg cgcg 14

<210> SEQ ID NO 311
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 311
ggtcggagag agat 14

<210> SEQ ID NO 312
<211> LENGTH: 14
<212> TYPE: DNA
<213> ORGANISM: Artificial Sequence
<220> FEATURE:

<223> OTHER INFORMATION: modified TGF-beta oligonucleotide

<400> SEQUENCE: 312
cacggaaata acct 14

<210> SEQ ID NO 313
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 313
agagcgcgaa cagg 14

<210> SEQ ID NO 314
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 314
atagtcccgc ggcc 14

<210> SEQ ID NO 315
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 315
tagtagtcgg cctc 14

<210> SEQ ID NO 316
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 316
atagatttcg ttgt 14

<210> SEQ ID NO 317
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 317
gaggtatcgc cagg 14

<210> SEQ ID NO 318
<211> LENGTH: 14
<212> TYPE: DNA
<213> ORGANISM: Artificial Sequence
<220> FEATURE:
<223> OTHER INFORMATION: modified TGF-beta oligonucleotide

<400> SEQUENCE: 318
gccgcacaac tccg 14

<210> SEQ ID NO 319
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 319
tcgcgccaag agg 13

<210> SEQ ID NO 320
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 320
aagcgtcccc ggc 13

<210> SEQ ID NO 321
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 321
gacgccgtgt agg 13

<210> SEQ ID NO 322
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 322
gtcggcgact ccc 13

<210> SEQ ID NO 323
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 323
tgcgcccgag gtc 13

<210> SEQ ID NO 324
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 324
gtcggagaga gat 13

<210> SEQ ID NO 325
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 325
tcccacggaa ata 13

<210> SEQ ID NO 326
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 326
tgccgagagc gcg 13

<210> SEQ ID NO 327
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 327
tagtcccgcg gcc 13

<210> SEQ ID NO 328
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 328
tagtagtcgg cct 13

<210> SEQ ID NO 329
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 329
catagatttc gtt 13

<210> SEQ ID NO 330
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 330
tttaacttga gcc 13

<210> SEQ ID NO 331
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 331
gaggtatcgc cag 13

<210> SEQ ID NO 332
<211> LENGTH: 13

<212> TYPE: DNA
<213> ORGANISM: Artificial Sequence
<220> FEATURE:
<223> OTHER INFORMATION: modified TGF-beta oligonucleotide

<400> SEQUENCE: 332
actccggtga cat 13

<210> SEQ ID NO 333
<211> LENGTH: 13
<212> TYPE: DNA
<213> ORGANISM: Artificial Sequence
<220> FEATURE:
<223> OTHER INFORMATION: modified TGF-beta oligonucleotide

<400> SEQUENCE: 333
gcccacgtag tac 13

<210> SEQ ID NO 334
<211> LENGTH: 12
<212> TYPE: DNA
<213> ORGANISM: Artificial Sequence
<220> FEATURE:
<223> OTHER INFORMATION: modified TGF-beta oligonucleotide

<400> SEQUENCE: 334
tcggcgactc cc 12

<210> SEQ ID NO 335
<211> LENGTH: 12
<212> TYPE: DNA
<213> ORGANISM: Artificial Sequence
<220> FEATURE:
<223> OTHER INFORMATION: modified TGF-beta oligonucleotide

<400> SEQUENCE: 335
gtcggcgact cc 12

<210> SEQ ID NO 336
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 336
caggaagcgc tggcaac 17

<210> SEQ ID NO 337
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 337
ggtgcatgaa ctcactg 17

<210> SEQ ID NO 338
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 338
gtcccctaat ggcttcc 17

<210> SEQ ID NO 339
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 339
atctgtcccc taatggc 17

<210> SEQ ID NO 340
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 340
ccgggtgctg ttgtaaa 17

<210> SEQ ID NO 341
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 341
cctggatcat gtcgaat 17

<210> SEQ ID NO 342
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 342
ccctggatca tgtcgaa 17

<210> SEQ ID NO 343
<211> LENGTH: 17
<212> TYPE: DNA
<213> ORGANISM: Artificial Sequence
<220> FEATURE:
<223> OTHER INFORMATION: modified TGF-beta3 oligonucleotide

<400> SEQUENCE: 343
gtagcacctg cttccag 17

<210> SEQ ID NO 344
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 344
gggctttcta aatgac 16

<210> SEQ ID NO 345
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 345
tgactcccag caggcc 16

<210> SEQ ID NO 346
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 346
gtgcatgaac tcactg 16

<210> SEQ ID NO 347
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 347
ggtgcatgaa ctcact 16

<210> SEQ ID NO 348
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 348
atctgtcccc taatgg 16

<210> SEQ ID NO 349
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 349
cgggtgctgt tgtaaa 16

<210> SEQ ID NO 350
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 350
ccgggtgctg ttgtaa 16

<210> SEQ ID NO 351
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 351
cctggatcat gtcgaa 16

<210> SEQ ID NO 352
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 352
ccctggatca tgtcga 16

<210> SEQ ID NO 353
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 353
tttgaatttg atttcc 16

<210> SEQ ID NO 354
<211> LENGTH: 16
<212> TYPE: DNA
<213> ORGANISM: Artificial Sequence
<220> FEATURE:
<223> OTHER INFORMATION: modified TGF-beta3 oligonucleotide

<400> SEQUENCE: 354
gggcctgagc agaagt 16

<210> SEQ ID NO 355
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 355
gggggctttc taaat 15

<210> SEQ ID NO 356
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 356
tttgtttaca cttcc 15

<210> SEQ ID NO 357
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 357
ccagctaaag gtggg 15

<210> SEQ ID NO 358
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 358
atggctgggt cccaa 15

<210> SEQ ID NO 359
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 359
gagtttttcc ttagg 15

<210> SEQ ID NO 360
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 360
aggggtggca aggca 15

<210> SEQ ID NO 361
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 361
tgactcccag caggc 15

<210> SEQ ID NO 362
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 362
gaagcgctgg caacc 15

<210> SEQ ID NO 363
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 363
gtgcatgaac tcact 15

<210> SEQ ID NO 364
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 364
gtggtgcaag tggac 15

<210> SEQ ID NO 365

<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 365
ctaatggctt ccacc 15

<210> SEQ ID NO 366
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 366
cccctaatgg cttcc 15

<210> SEQ ID NO 367
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 367
atctgtcccc taatg 15

<210> SEQ ID NO 368
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 368
gatctgtccc ctaat 15

<210> SEQ ID NO 369
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 369
agatctgtcc cctaa 15

<210> SEQ ID NO 370
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 370
ggtgctgttg taaag 15

<210> SEQ ID NO 371
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 371
ccgggtgctg ttgta 15

<210> SEQ ID NO 372
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 372
gatcatgtcg aattt 15

<210> SEQ ID NO 373
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 373
cctggatcat gtcga 15

<210> SEQ ID NO 374
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 374
ccctggatca tgtcg 15

<210> SEQ ID NO 375
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 375
gatttccatc acctc 15

<210> SEQ ID NO 376
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 376
ttgaatttga tttcc 15

<210> SEQ ID NO 377
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 377
agcagttctc ctcca 15

<210> SEQ ID NO 378
<211> LENGTH: 15
<212> TYPE: DNA

<213> ORGANISM: Artificial Sequence
<220> FEATURE:
<223> OTHER INFORMATION: modified TGF-beta3 oligonucleotide

<400> SEQUENCE: 378
gcctgagcag aagtt 15

<210> SEQ ID NO 379
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 379
gggcaagggc ctgag 15

<210> SEQ ID NO 380
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 380
cccacacttt cttta 15

<210> SEQ ID NO 381
<211> LENGTH: 15
<212> TYPE: DNA
<213> ORGANISM: Artificial Sequence
<220> FEATURE:
<223> OTHER INFORMATION: modified TGF-beta3 oligonucleotide

<400> SEQUENCE: 381
tagcacctgc ttcca 15

<210> SEQ ID NO 382
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 382
cgggggcttt ctaa 14

<210> SEQ ID NO 383
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 383
ccattcatgc tttc 14

<210> SEQ ID NO 384
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 384
aagcgctggc aacc 14

-continued

<210> SEQ ID NO 385
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 385
accagagccc tttg 14

<210> SEQ ID NO 386
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 386
cccctaatgg cttc 14

<210> SEQ ID NO 387
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 387
gtcccctaat ggct 14

<210> SEQ ID NO 388
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 388
atctgcccct aat 13

<210> SEQ ID NO 389
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 389
agatctgtcc ccta 14

<210> SEQ ID NO 390
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 390
cgggtgctgt tgta 14

<210> SEQ ID NO 391
<211> LENGTH: 14
<212> TYPE: DNA
<213> ORGANISM: Artificial Sequence
<220> FEATURE:

<223> OTHER INFORMATION: modified TGF-beta3 oligonucleotide

<400> SEQUENCE: 391
atcatgtcga attt 14

<210> SEQ ID NO 392
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 392
ccctggatca tgtc 14

<210> SEQ ID NO 393
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 393
cctttgaatt tgat 14

<210> SEQ ID NO 394
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 394
ttgcggaagc agta 14

<210> SEQ ID NO 395
<211> LENGTH: 14
<212> TYPE: DNA
<213> ORGANISM: Artificial Sequence
<220> FEATURE:
<223> OTHER INFORMATION: modified TGF-beta3 oligonucleotide

<400> SEQUENCE: 395
gcctgagcag aagt 14

<210> SEQ ID NO 396
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 396
gggggctttc taa 13

<210> SEQ ID NO 397
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 397
agcgctggca acc 13

<210> SEQ ID NO 398
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 398
cccctaatgg ctt 13

<210> SEQ ID NO 399
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 399
tcccctaatg gct 13

<210> SEQ ID NO 400
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 400
tcatgtcgaa ttt 13

<210> SEQ ID NO 401
<211> LENGTH: 13
<212> TYPE: DNA
<213> ORGANISM: Artificial Sequence
<220> FEATURE:
<223> OTHER INFORMATION: modified TGF-beta3 oligonucleotide

<400> SEQUENCE: 401
atcatgtcga att 13

<210> SEQ ID NO 402
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 402
agtatttggt ctcc 14

<210> SEQ ID NO 403
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 403
agtatttggt ctcca 15

<210> SEQ ID NO 404
<211> LENGTH: 15
<212> TYPE: DNA
<213> ORGANISM: Artificial Sequence
<220> FEATURE:
<223> OTHER INFORMATION: modified TGF-beta2 oligonucleotide -continued

<400> SEQUENCE: 404
aagtatttgg tctcc 15

<210> SEQ ID NO 405
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 405
caaagtattt ggtctc 16

<210> SEQ ID NO 406
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 406
caaagtattt ggtct 15

<210> SEQ ID NO 407
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 407
caaagtattt ggtc 14

<210> SEQ ID NO 408
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 408
aaagtatttg gtctcc 16

<210> SEQ ID NO 409
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 409
aaagtatttg gtctc 15

<210> SEQ ID NO 410
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 410
aaagtatttg gtct 14

<210> SEQ ID NO 411
<211> LENGTH: 13

```
<212> TYPE: DNA
<213> ORGANISM: Artificial Sequence
<220> FEATURE:
<223> OTHER INFORMATION: modified TGF-beta2 oligonucleotide

<400> SEQUENCE: 411

aaagtatttg gtc                                                          13


<210> SEQ ID NO 412
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 412

aagtatttgg tct                                                          13


<210> SEQ ID NO 413
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 413

aagtatttgg tc                                                           12


<210> SEQ ID NO 414
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 414

agtatttggt ctc                                                          13


<210> SEQ ID NO 415
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 415

agtatttggt ct                                                           12


<210> SEQ ID NO 416
<211> LENGTH: 11
<212> TYPE: DNA
<213> ORGANISM: Artificial Sequence
<220> FEATURE:
<223> OTHER INFORMATION: modified TGF-beta2 oligonucleotide

<400> SEQUENCE: 416

agtatttggt c                                                            11


<210> SEQ ID NO 417
<211> LENGTH: 14
<212> TYPE: DNA
<213> ORGANISM: Artificial Sequence
<220> FEATURE:
<223> OTHER INFORMATION: modified TGF-beta2 oligonucleotide
```

-continued

<400> SEQUENCE: 417
aagtatttgg tctc 14

MODIFIED TGF-BETA OLIGONUCLEOTIDE FOR USE IN A METHOD OF PREVENTING AND/OR TREATING AN OPHTHALMIC DISEASE

CROSS REFERENCE TO RELATED APPLICATIONS

This application claims the priority of PCT/EP2014/056222, filed on Mar. 27, 2014, which claims priority to European Patent Application No. 13161474.5, filed on Mar. 27, 2013; European Patent Application No. 13173078.0, filed on Jun. 20, 2013; European Patent Application No. 13199826.2, filed on Dec. 30, 2013; European Patent Application No. 13199831.2, tiled on Dec. 30, 2013; and European Patent Application 13199838.7, filed on Dec. 30, 2013, the entire contents of each of which are hereby incorporated in total by reference.

SEQUENCE LISTING

This application incorporates by reference the Sequence Listing contained in an ASCII text file named "362346_00028_SeqList.txt" submitted via EFS-Web. The text file was created on Sept. 24, 2015, and is 100 kb in size.

The invention is directed to a TGF-beta oligonucleotide comprising a bridged nucleotide, polyalkylene oxide-, 2'-fluoro, 2'-O-methoxy and/or 2'-O-methyl modified nucleotide for use in a method of preventing and/or treating an ophthalmic disease.

Technical Background

Transforming growth factor beta (TGF-beta), a multifunctional growth factor that for example controls proliferation or cellular differentiation, is one of the most important ligands involved in the regulation of cell behavior in ocular tissues in physiological or pathological processes of development or tissue repair, although various other growth factors are also involved. Increased activity of this ligand may induce unfavorable inflammatory responses and tissue fibrosis. In mammals, three isoforms of TGF-beta, that is beta1, beta2, and beta3, are known. In most cases, TGF-beta enhances extracellular matrix production and suppresses cell proliferation. Moreover, TGF-beta is capable of inducing a number of growth factors, that is connective tissue growth factor (CTGF), platelet-derived growth factor (PDGF), fibroblast growth factors (FGFs), and vascular endothelial growth factor (VEGF), as well as TGF-beta1 itself. All these factors have important roles in restoration of normal tissue following injury.

The aqueous humor that bathes the inner ocular structures (corneal endothelium, iris, crystalline lens, trabecular meshwork, and retina) contains various cytokines and growth factors. TGF-beta, in particular TGF-beta2, is the predominant cytokine. Physiologically, TGF-beta is mainly produced in the ciliary epithelium and lens epithelium as a latent, inactive, form consisting of mature TGF-beta, the latency-associated peptide (LAP) (small latent form), and the latent-TGF-beta-binding protein (LTBP). Heterogeneous expression patterns of each TGF-beta isoform in the crystalline lens have been reported in humans and animals. During the clinical course of various ocular diseases, the concentration of TGF-beta2 in the aqueous humor changes. For example, in an eye with proliferative vitreoretinopathy (PVR), a disorder of post-retinal detachment and retinal fibrosis, the concentration of TGF-beta2 in the vitreous humor increases in association with the progression of retinal fibrosis. The concentration of total and active TGF-beta2 is also higher in patients with diabetic retinopathy and open-angle glaucoma than in normal subjects. In diabetic retinopathy, chronic obstruction of retinal microvessels induces upregulation of VEGF and chemotaxis of macrophages, a potent source of TGF-beta. VEGF and TGF-beta cooperate to induce both retinal neovascularization and fibrosis around these new vessels, which may potentially cause retinal detachment or bleeding. Increased TGF-beta2 levels induce matrix expression and deposition in trabecular meshwork cells, leading to obstruction of the aqueous drainage route and an increase of intraocular pressure in a glaucomatous eye. In each of these examples, TGF-beta plays a role in disease pathogenesis. In eyes with pseudo-exforiation syndrome, a kind of glaucoma with deposition of exforiative material on the lens, iris, or trabecular meshwork, the level of TGF-beta1 increases, but the exact role of TGF-beta1 in the pathogenesis of this disease is unknown (see Shizuya Saika, Laborartory Investigation (2006), 86, 106-115).

TGF-beta is one of the most potent regulators of the production and deposition of extracellular matrix. It stimulates the production and affects the adhesive properties of the extracellular matrix by two major mechanisms. First, TGF-beta stimulates fibroblasts and other cells to produce extra-cellular-matrix proteins and cell-adhesion proteins, including collagen, fibronectin, and integrins. Second, TGF-beta decreases the production of enzymes that degrade the extra-cellular matrix, including collagenase, heparinase, and stromelysin, and increases the production of proteins that inhibit enzymes that degrade the extracellular matrix, including plasminogen-activator inhibitor type 1 and tissue inhibitor of metalloprotease. The net effect of these changes is to increase the production of extracellular-matrix proteins and either to increase or to decrease the adhesive properties of cells in a cell-specific manner (see Blobe G C et al., May 2000, "Role of transforming growth factor beta in human disease", N. Engl. J. Med. 342 (18), 1350-1358).

Targeting TGF-beta has been proposed as a potential therapeutic measure for example in glaucoma. Concerning various aspects of TGF-beta in the pathogenesis of glaucoma, therapies should be directed to modulate its production, activation, interaction with receptors, downstream intracellular regulatory mechanisms and/or the final structural and ECM changes (see Prendes M A et al., Br J Ophthalmol (2013), 97, 680-686).

Glaucoma (GCM), based upon chronically increased intraocular pressure, is a progressive optic neuropathy characterized by progressive loss of retinal ganglion cells, which manifests clinically with loss of optic disc neuroretinal rim tissue, defects in the retinal nerve fiber layer, and deficits on functional visual field testing (see Danesh-Meyer et al., Ophthalmol. 2006, 113: 603-611). Glaucoma is the second leading cause for blindness in the adult in the USA. Despite a multitude of treatment options, including surgical procedures in referactory patients, blindness remains a major threat. Primary open-angle glaucoma (POAG) is the most common form of glaucoma in the USA. Worldwide, in the year 2000 the number of people with POAG has been estimated at nearly 66.8 million with 6.7 million having bilateral blindness (see Quingley, Br J Ophthalmol. 1996 May; 80(5):389-393).

Cataract surgery is the most common ophthalmic surgical procedure. Alone in the USA, up to 3.000.000 cataract surgeries are performed per year. The US government spends currently more than USD 3 billion per year on treating cataract (Medicare patients only). The lens of the eye is removed by the procedure, and an intraocular lens is implanted. The lens capsule remains in situ, and the posterior part of the capsule frequently develops posterior capsule opacification (PCO) due to mechanical disruption and potential other factors associated with lens replacement. This condition occurs in 20 to 40% of PCO patients, YAG-laser posterior capsulotomy (rates depend on country, lens type used and surgical experience) is performed within the first two years, to remove the opacification (see Johansson B et al., Br J Ophthalmol (2010), 94, 450-455; Mathew R G et al., Ophthalmic Surg Lasers Imaging (2010), 41, 651-655). The use of the YAG-laser is associated with distinct risks, including retinal detachment (1-3%), cystoid macular oedema (up to 5%) and secondary glaucoma (see Billotte C and Berdeaux G, J Cataract Refract Surg (2004), 30(10), 2064-2071).

TGF-beta has been closely associated with the pathophysiology of both, GCM and PCO; so far, the effect of the TGF-beta protein has been inhibited by ALK5 inhibitors as for example described in WO 2009/146408 or antibodies directed to TGF-beta, i.e., one of its isoforms, which are disclosed for example in WO 2012/167143. None of these compounds has so far been successful in effective inhibiting TGF-beta in the eye, and thus, to be successful in the prevention and/or treatment of ophthalmic diseases such as GCM or PCO.

It is the objective of the present invention to provide an oligonucleotide, preferably an antisense oligonucleotide, which is specifically inhibiting the expression of TGF-beta1, TGF-beta2, and/or TGF-beta3 mRNA, TGF-beta1 and TGF-beta2 mRNA, or TGF-beta1 and TGF-beta3 mRNA, or TGF-beta2 and TGF-beta3 mRNA, and consequently is highly efficient for use in prevention and/or treatment of an ophthalmic disease without causing any (severe) side effects.

Summary of the Invention

The present invention refers to the use of a TGF-beta oligonucleotides, preferably a TGF-beta1, TGF-beta2, and/or TGF-beta3 antisense oligonucleotide for use in a method for treating an ophthalmic disease such as dry eye, glaucoma or posterior capsule opacification.

The TGF-beta oligonucleotide consists of 10 to 20, preferably 12 to 18 nucleotides of the TGF-beta1 nucleic acid sequence of SEQ ID NO. 1 (see FIG. 1), or of the TGF-beta2 nucleic acid sequence of SEQ ID NO. 2 (see FIG. 2), or of the TGF-beta3 nucleic acid sequence of SEQ ID NO. 3 (see FIG. 3), wherein one or more nucleotide(s) of the oligonucleotide is/are modified. Some of the oligonucleotides of the present invention correspond to TGF-beta1, TGF-beta2, and TGF-beta3, or to TGF-beta1 and TGF-beta2, or TGF-beta1 and TGF-beta3, or TGF-beta2 and TGF-beta3, and hybridize with one or more of these sequences.

In particular, oligonucleotides for use in the present invention comprise or consist of 10 to 20, more preferred of 12 to 18 nucleotides of the region of nucleic acid no. 1380 to 1510 of SEQ ID NO. 2, wherein one or more nucleotide(s) of the oligonucleotide is/are modified. These oligonucleotides are highly effective in the reduction and inhibition of TGF-beta2 expression and activity, respectively. A preferred oligonucleotide comprises or consists of SEQ ID NO. 5 (e.g., ASPH36: GACCAGATGCAGGA), SEQ ID NO. 6 (e.g., ASPH80: GCGACCGTGACCAGAT), SEQ ID NO. 7 (e.g., ASPH98: GCGCGACCGTGACC), SEQ ID NO. 8 (e.g., ASPH111: AGCGCGACCGTGA), or SEQ ID NO. 9 (e.g., ASPH121 or ASPH153: GACCGTGACCAGAT), SEQ ID NO. 10 (e.g., ASPH15: CTGCCCGCGGAT), SEQ ID NO. 11 (e.g., ASPH17: TCTGCCCGCGGAT), SEQ ID NO. 12 (e.g., ASPH26 or ASPH27: GGATCTGCCCGCGGA), SEQ ID NO. 13 (e.g., ASPH37: CTTGCTCAGGATCTGCC), SEQ ID NO. 14 (e.g., ASPH52 or 53: GCTCAGGATCTGCCCGCGGA), SEQ ID NO. 15 (e.g., ASPH112: GGATCGCCTCGAT), SEQ ID NO. 16 (e.g., ASPH119: CCGCGGATCGCC), or SEQ ID NO. 34 (e.g., ASPH30: CGATCCTCTTGCGCAT).

In another embodiment the invention refers to an oligonucleotide, comprising or consisting of 10 to 20, more preferred of 12 to 18 nucleotides of the region of nucleic acid no. 2740 to 2810 of the TGF-beta2 nucleic acid sequence of SEQ ID NO. 2 wherein one or more nucleotide(s) of the oligonucleotide is/are modified. These oligonucleotides are highly effective in the reduction and inhibition of TGF-beta2 expression and activity, respectively. A preferred oligonucleotide comprises or consists of SEQ ID NO. 60 (e.g., ASPH65: TCTGAACTAGTACCGCC), SEQ ID NO. 76 (e.g., ASPH82: AACTAGTACCGCCTTT), or SEQ ID NO. 106 (e.g., ASPH115: CTAGTACCGCCTT).

In a further embodiment the invention refers to an oligonucleotide, comprising or consisting of 10 to 20, more preferred of 12 to 18 nucleotides of the region of nucleic acid no. 1660 to 1680 of the TGF-beta2 nucleic acid sequence of SEQ ID NO. 2 wherein one or more nucleotide(s) of the oligonucleotide is/are modified. These oligonucleotides are highly effective in the reduction and inhibition of TGF-beta1 and/or TGF-beta2 expression and activity, respectively. A preferred oligonucleotide comprises or consists of SEQ ID NO. 17 (e.g., ASHP01 or ASPH02: ACCTCCTTGGCGTAGTA), SEQ ID NO. 18 (e.g., ASPH03 or ASPH04: CCTCCTTGGCGTAGTA), SEQ ID NO. 19 (e.g., ASPH05, ASPH06, or ASPH07: CTCCTTGGCGTAGTA), or SEQ ID NO.20 (e.g., ASPH08: TCCTTGGCGTAGTA).

In another embodiment the invention relates to an oligonucleotide, comprising or consisting of 10 to 20, more preferred of 12 to 18 nucleotides, most preferably 13 nucleotides of the region of nucleic acid no. 2390 to 2410 of the TGF-beta2 nucleic acid sequence of SEQ ID NO. 2 wherein one or more nucleotide(s) of the oligonucleotide is/are modified. These oligonucleotides are highly effective in the reduction and inhibition of TGF-beta1, TGF-beta2, and/or TGF-beta3 expression and activity, respectively. A preferred oligonucleotide comprises or consists of SEQ ID NO. 21 (e.g., ASPH9 or ASPH10: CAGAAGTTGGCAT).

In another embodiment the invention relates to an oligonucleotide, comprising or consisting of 10 to 20, more preferred of 12 to 18 nucleotides of the TGF-beta2 nucleic acid sequence of SEQ ID NO. 2 wherein one or more nucleotide(s) of the oligonucleotide is/are modified. These oligonucleotides are highly effective in the reduction and inhibition of TGF-beta1, TGF-beta2, and/or TGF-beta3, most preferably of TGF-beta2 expression and activity, respectively. A preferred oligonucleotide comprises or consists of one of SEQ ID NO. 22 to 59, 61 to 75, 77 to 105, 107 to 140 (e.g., ASHP11-ASPH14, ASPH16, ASPH18-ASPH25, ASPH28-ASPH35, ASPH38-ASPH51, ASPH60-ASPH64, ASPH66-ASPH79, ASPH81, ASPH83-ASPH97, ASPH99-ASPH110, ASPH113, ASPH114, ASPH116-ASPH118, ASPH120, ASPH122-ASPH152, ASPH154-ASPH183, or T-LNA (SEQ ID NO: 144)).

Preferred oligonucleotides of the present invention are ASPH01, ASPH03, ASPH05, ASPH17, ASPH22, ASPH26, ASPH27, ASPH35, ASPH36, ASPH37, ASPH45, ASPH47, ASPH48, ASPH65, ASPH69, ASPH71, ASPH80, ASPH82, ASPH98, ASPH105, ASPH115, ASPH190, ASPH191, ASPH192, and ASPH193, respectively.

Further preferred oligonucleotides of the present invention are ASPH1000 to ASPH1132 as shown in Table 1, which preferably inhibit the expression and/or activity of TGFbeta1 mRNA. Preferred oligonucleotides this group are for example ASPH1047, ASPH1051, ASPH1059, ASPH1106, ASPH1139, ASPH1150, ASPH1162, ASPH1163, ASPH1175, ASPH1178, and ASPH1181, respectively.

In an alternative embodiment oligonucleotides are preferably inhibiting the expression and/or activity of TGF-beta3 mRNA. Such oligonucleotides are for example ASPH2000, ASPH2001, ASPH2002, ASPH2003, ASPH2004, ASPH2005, ASPH2006, ASPH2007, ASPH2008, ASPH2009, ASPH2010, ASPH2011, ASPH2012, ASPH2013, ASPH2014, ASPH2015, ASPH2016, ASPH2017, ASPH2018, ASPH2019, ASPH2020, ASPH2021, ASPH2022, ASPH2023, ASPH2024, ASPH2025, ASPH2026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2042, ASPH2043, ASPH2044, ASPH2045, ASPH2046, ASPH2047, ASPH2048, ASPH2049, ASPH2050, ASPH2051, ASPH2052, ASPH2053, ASPH2054, ASPH2055, ASPH2056, ASPH2057, ASPH2058, ASPH2059, ASPH2060, ASPH2061, ASPH2062, ASPH2063, ASPH2064, ASPH2065, and ASPH2066, respectively.

Oligonucleotides of the present invention show an unexpected strong and specific inhibition of TGF-beta1, TGF-beta2, or TGF-beta3, or TGF-beta1 and TGF-beta2. Alternatively, oligonucleotides of the present invention show strong and specific inhibition of TGF-beta1 and TGF-beta3, or TGF-beta1 and TGF-beta2, or TGF-beta2 and TGF-beta3, and in a further alternative TGF-beta1, TGF-beta2 and TGF-beta3.

Modifications of one or more nucleotides of the oligonucleotides of the present invention are selected from the group consisting of LNA, ENA, polyalkylene oxide such as triethylene glycol (TEG), 2'-fluoro, 2'-O-methoxy and 2'-O-methyl. The modifications are preferably located at the 5'- and/or 3'-end of the oligonucleotide. An oligonucleotide comprising such modified nucleotide is a modified oligonucleotide.

Modified nucleotides are for example arranged in a row, one directly next to the other, or in different patterns, where one or more unmodified nucleotides follow a modified nucleotide. For example an oligonucleotide starts with one or more modified nucleotides followed by one or more, e.g., one, two, three or four, unmodified or unlocked nucleotides followed again by one or more modified nucleotides. In one embodiment both ends of the oligonucleotide comprise an identical pattern of modified and unmodified or unlocked nucleotides. In another embodiment, the pattern of modifications at the 3'- and 5'-end differ including that one end does not comprise a modified nucleotide. Preferably the modified oligonucleotides comprise a series of 8 or 9 unlocked nucleotides.

Alternatively, a nucleotide at any other position in the oligonucleotide is modified, or at least one nucleotide at the 5'- and/or 3'-end of the oligonucleotide and at any other position in the oligonucleotide. For example ASPH1071, ASPH1100, ASPH1109, ASPH 1110, ASPH1111, ASPH1115, ASPH1126, ASPH1127 and ASPH1128 belong to a group of TGF-beta oligonucleotides, for example TGF-beta1 oligonucleotides, which comprises modified nucleosides such as LNA, ENA etc. in different patterns, e.g., separated from each other by an unlocked nucleotide. The oligonucleotides comprise either one type of modification, or one or more different modifications. Optionally, at least one phosphate linkage between two consecutive nucleotides (modified or unmodified) of the oligonucleotide is a phosphorothioate or a methylphosphonate. In a preferred embodiment, the oligonucleotides of the present invention are phosphorothioates.

Moreover, the present invention refers to TGF-beta antisense oligonucleotides, which interact and inhibit the expression of more than one TGF-beta isoform, even if the oligonucleotide is not 100% complementary to the TGF-beta1, TGF-beta2 and/or TGF-beta3 sequence. Such antisense oligonucleotides are for example ASPH1024, ASPH1096, ASPH1131 and ASPH1132, respectively. These oligonucleotides preferably interact with TGF-beta sequences of the same or different species such as human, monkey, rat or mouse as for example ASPH1131 and ASPH1132, respectively.

All the oligonucleotides of the different embodiments are for use in a method of the prevention and/or treatment of an ophthalmic disease such as dry eye, glaucoma, posterior capsular opacification (PCO), retinoblastoma, choroidcarcinoma, Marfan or Loeys-Dietz syndrome, macular degeneration, such as age-related macular degeneration, diabetic macular endma, or cataract.

FIGURES

FIG. 1 presents the nucleic acid sequence of human TGF-beta1 mRNA (NM_000660.4).

FIG. 2 shows the nucleic acid sequence of human TGF-beta2 mRNA (NM_003238.3).

FIG. 3 depicts the nucleic acid sequence of human TGF-beta3 mRNA (NM_003239.2).

FIG. 4 presents examples of nucleotide modifications.

Figure 5A:
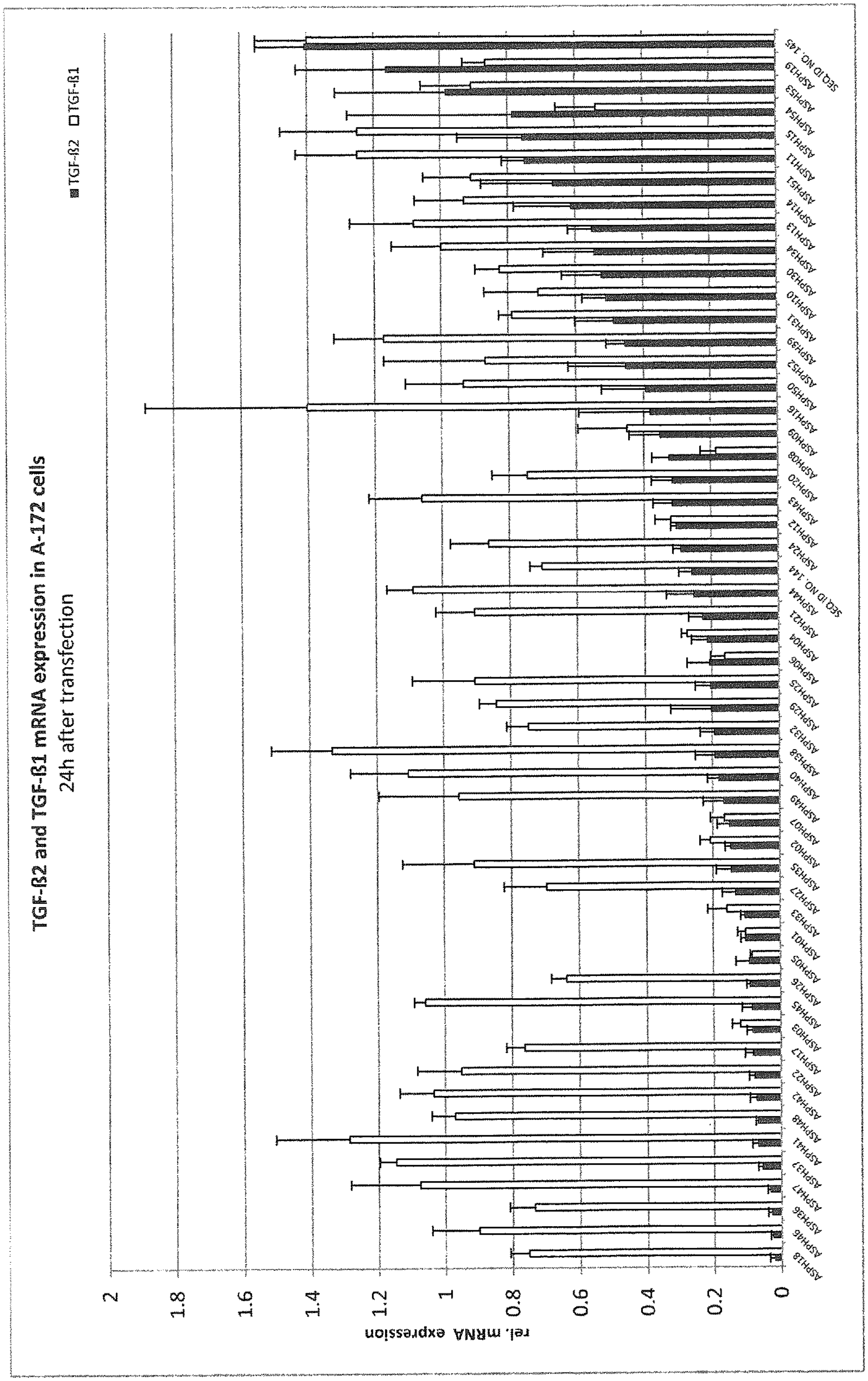
Figure 5B:
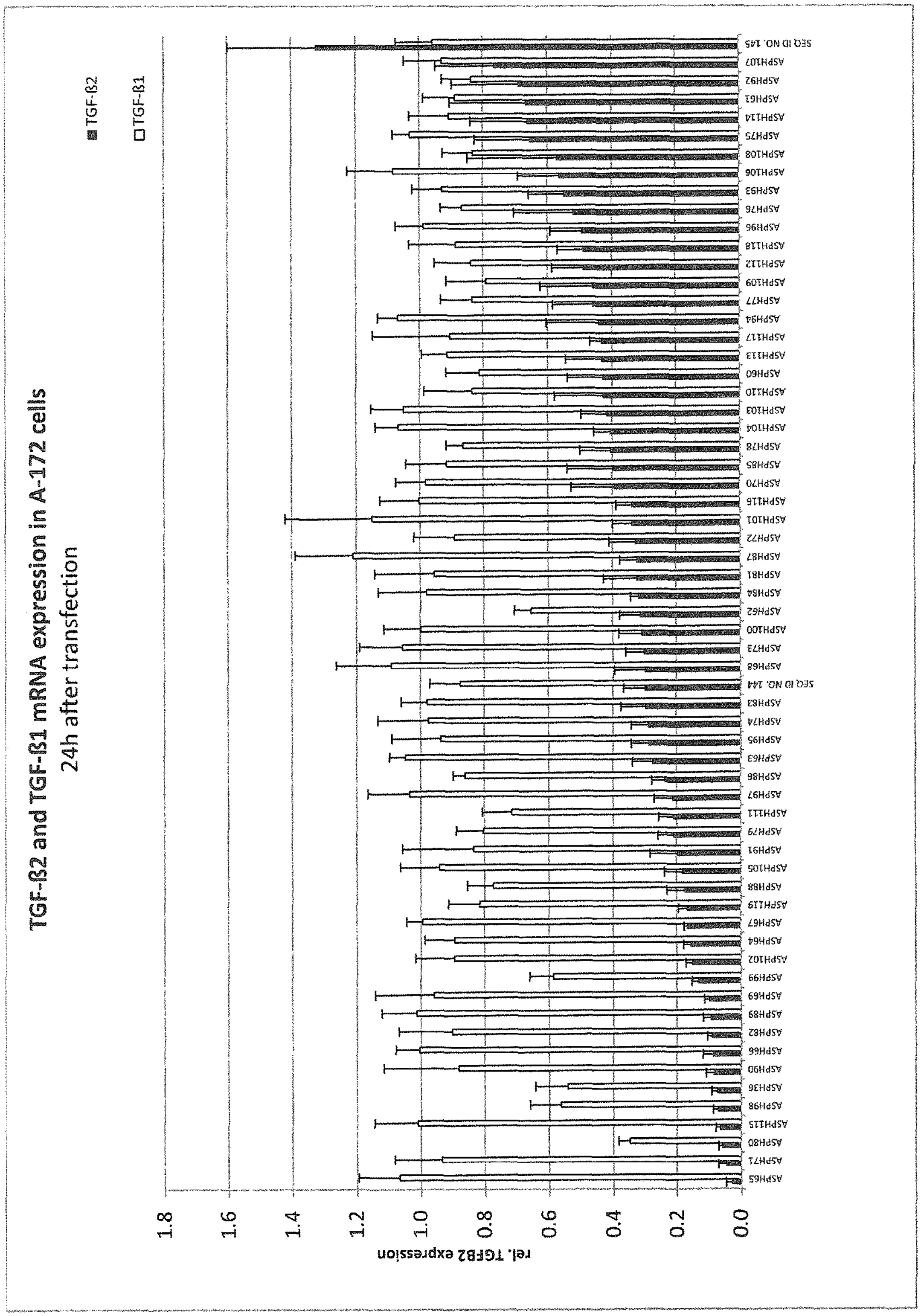
Figure 5C:
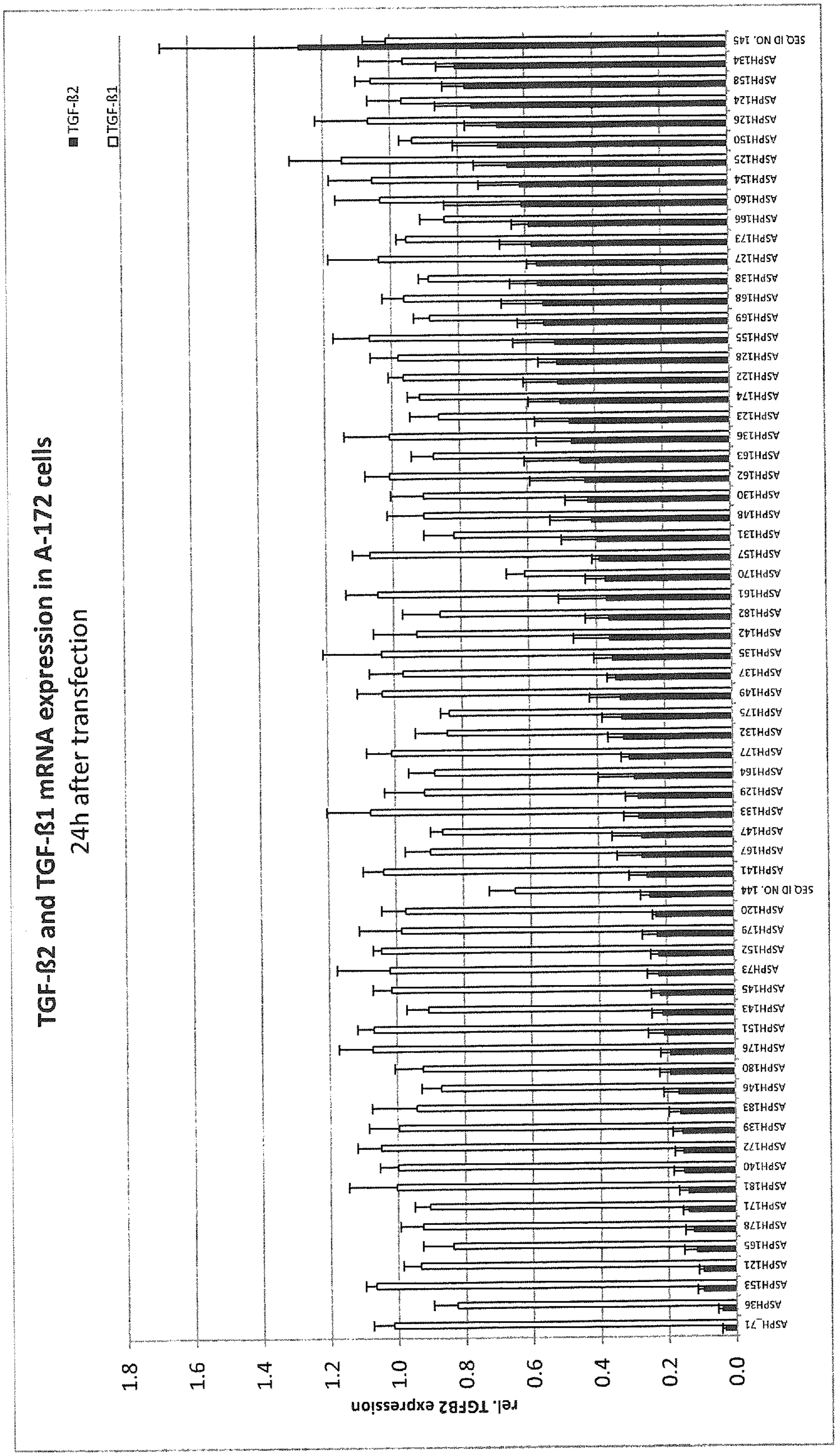

FIG. 5*a*) to 5*c*) depict the inhibition of the expression of TGF-beta1 and TGF-beta2 mRNA in human A172 glioma cells. A172 cells were transfected with different modified oligonucleotides in a dose of 10 nM (in the presence of a transfecting agent), and the inhibition of the TGF-beta1 (white columns) and TGF-beta2 (black columns) mRNA expression was measured 24 h after transfection. FIG. 5*a*) refers to the results for the modified oligonucleotides ASPH01, ASPH02, ASPH03, ASPH04, ASPH05, ASPH06, ASPH07, ASPH08, ASPH09, ASPH10, ASPH11, ASPH12, ASPH13, ASPH14, ASPH15, ASPH16, ASPH17, ASPH18, ASPH19, ASPH20, ASPH21, ASPH22, ASPH24, ASPH25, ASPH26, ASPH27, ASPH29, ASPH30, ASPH31, ASPH32, ASPH33, ASPH34, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, ASPH52, ASPH53, and ASPH54; FIG. 5*b*) to the results for the modified oligonucleotides ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH95, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119; and FIG. 5*c*) to the results for the modified oligonucleotides ASPH36, ASPH71, ASPH73, ASPH120, ASPH121, ASPH122, ASPH123, ASPH124, ASPH125, ASPH126, ASPH127, ASPH128, ASPH129, ASPH130, ASPH131, ASPH132, ASPH133, ASPH134, ASPH135, ASPH136, ASPH137, ASPH138, ASPH139, ASPH140, ASPH141, ASPH142, ASPH143, ASPH145, ASPH146, ASPH147, ASPH148, ASPH149, ASPH150, ASPH151, ASPH152, ASPH153, ASPH154, ASPH155, ASPH157, ASPH158, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183. Experiments are described in Example 1.

Figure 6A:
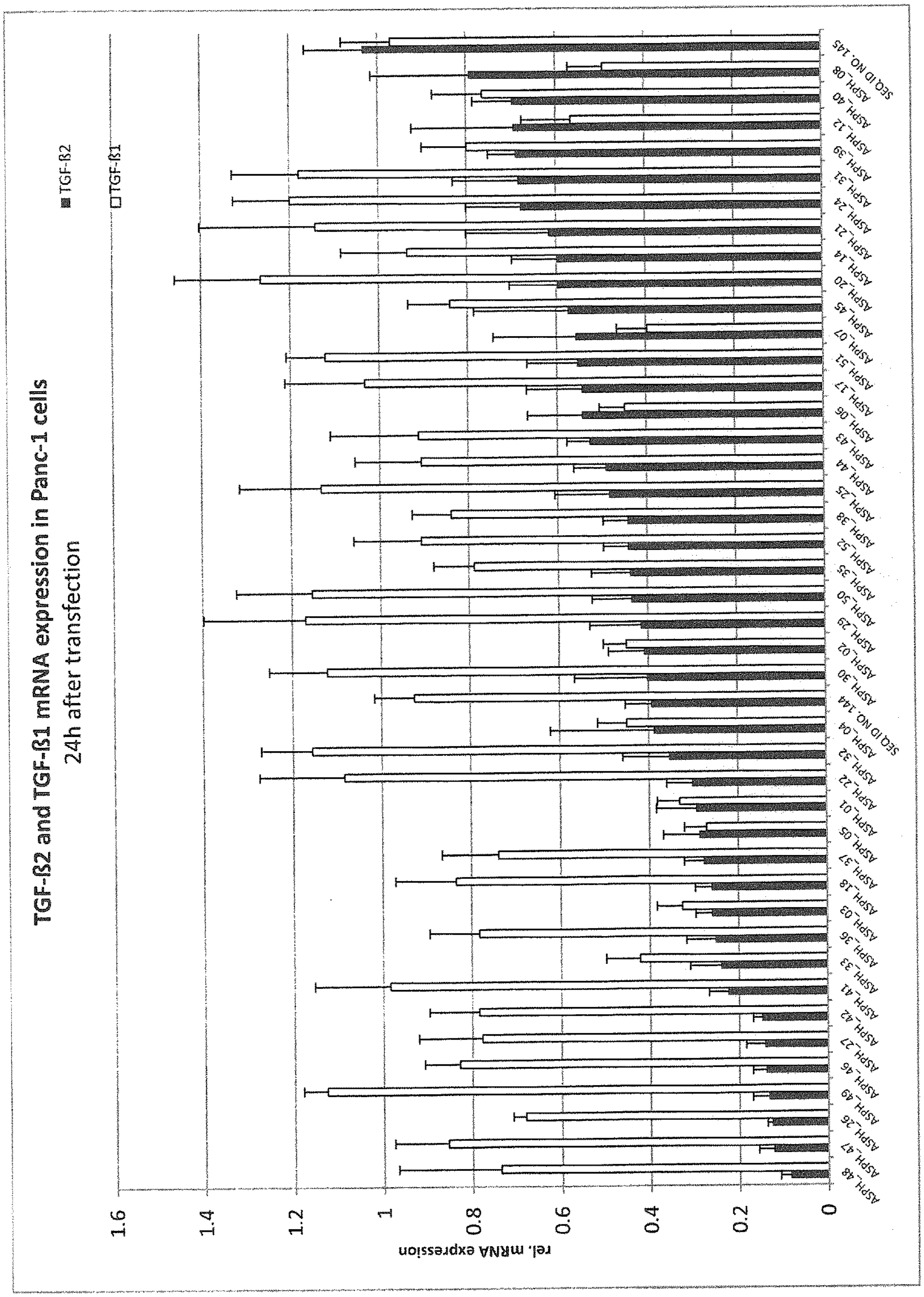
Figure 6B:
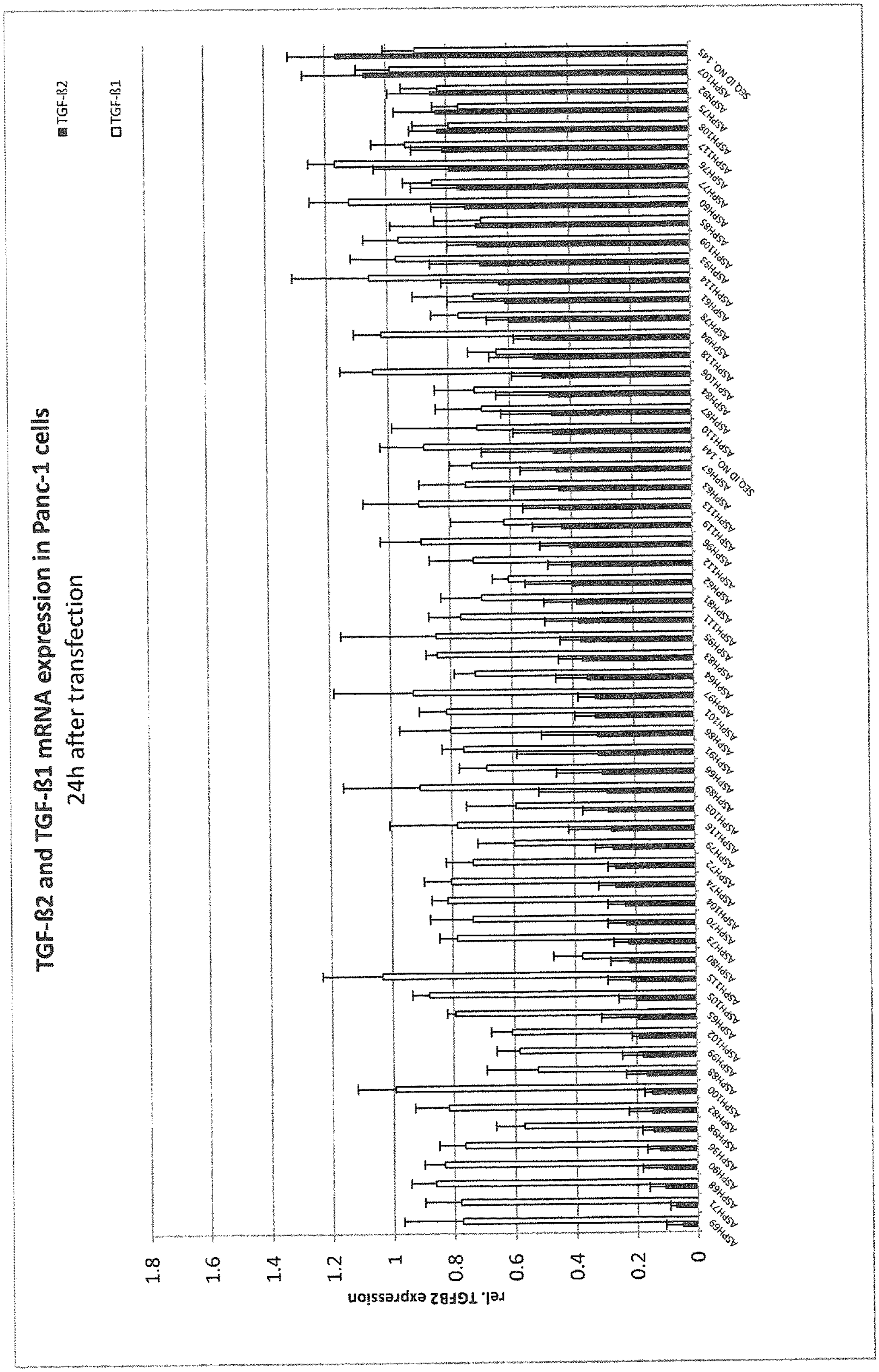
Figure 6C:
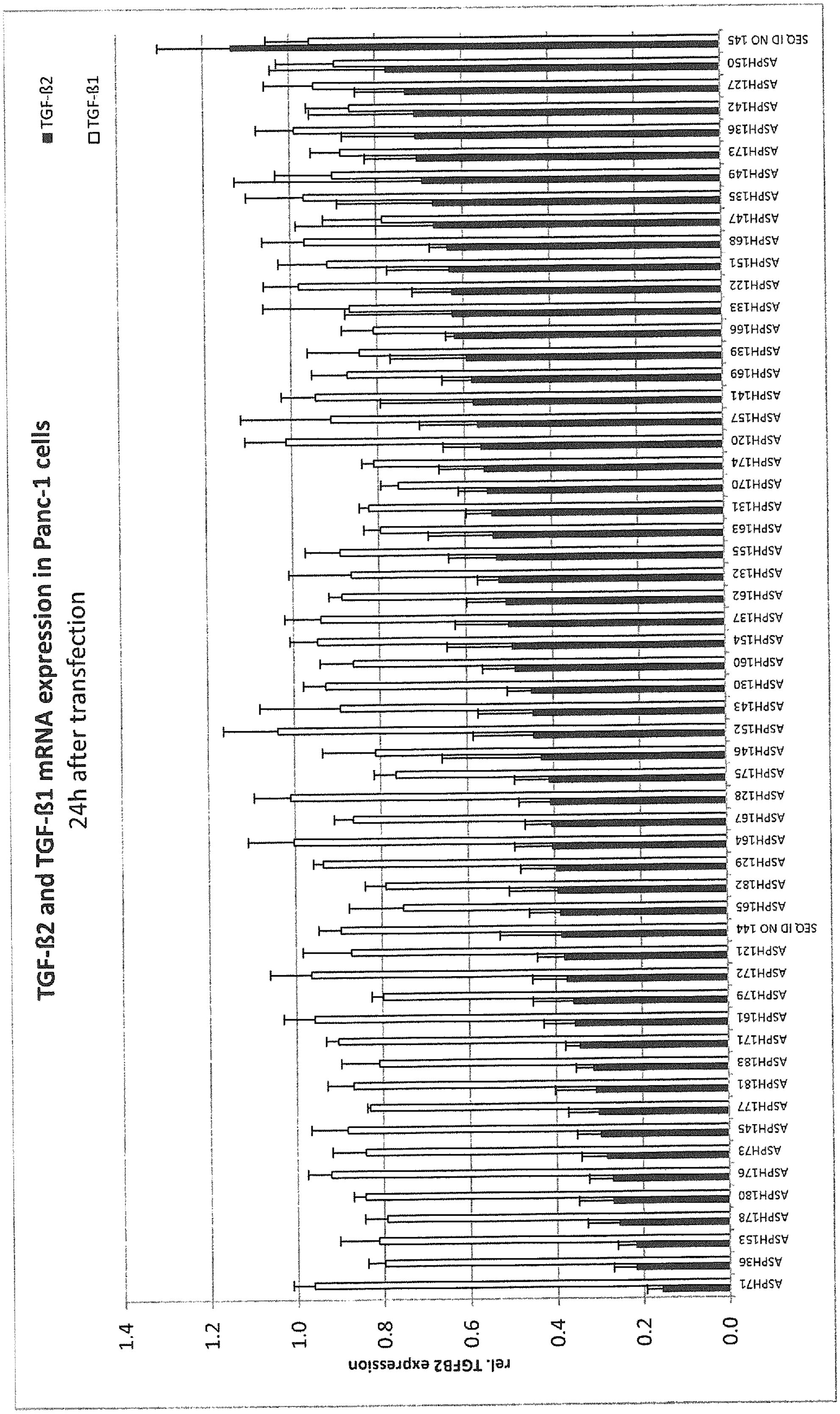

FIG. 6*a*) to 6*c*) depict the inhibition of the expression of TGF-beta1 and TGF-beta2 mRNA in human Panc-1 pancreatic cancer cells. Panc-1 cells were transfected with different modified oligonucleotides in a dose of 10 nM (in the presence of a transfecting agent), and the inhibition of the TGF-beta1 (white columns) and TGF-beta2 (black columns) mRNA expression was measured 24 h after transfection. FIG. 6*a*) refers to the results for the modified oligonucleotides ASPH01, ASPH02, ASPH03, ASPH04, ASPH05, ASPH06, ASPH07, ASPH08, ASPH12, ASPH14, ASPH17, ASPH18, ASPH20, ASPH21, ASPH22, ASPH24, ASPH25, ASPH26, ASPH27, ASPH29, ASPH30, ASPH31, ASPH32, ASPH33, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, and ASPH52; FIG. 6*b*) to the results for the modified oligonucleotides ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119; and FIG. 6*c*) to the results for the modified oligonucleotides ASPH36, ASPH71, ASPH73, ASPH120, ASPH121, ASPH122, ASPH127, ASPH128, ASPH129, ASPH130, ASPH131, ASPH132, ASPH133, ASPH135, ASPH136, ASPH137, ASPH139, ASPH141, ASPH142, ASPH143, ASPH145, ASPH146, ASPH147, ASPH149, ASPH150, ASPH151, ASPH152, ASPH153, ASPH154, ASPH155, ASPH157, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183. Experiments are described in Example 2.

Figure 7:
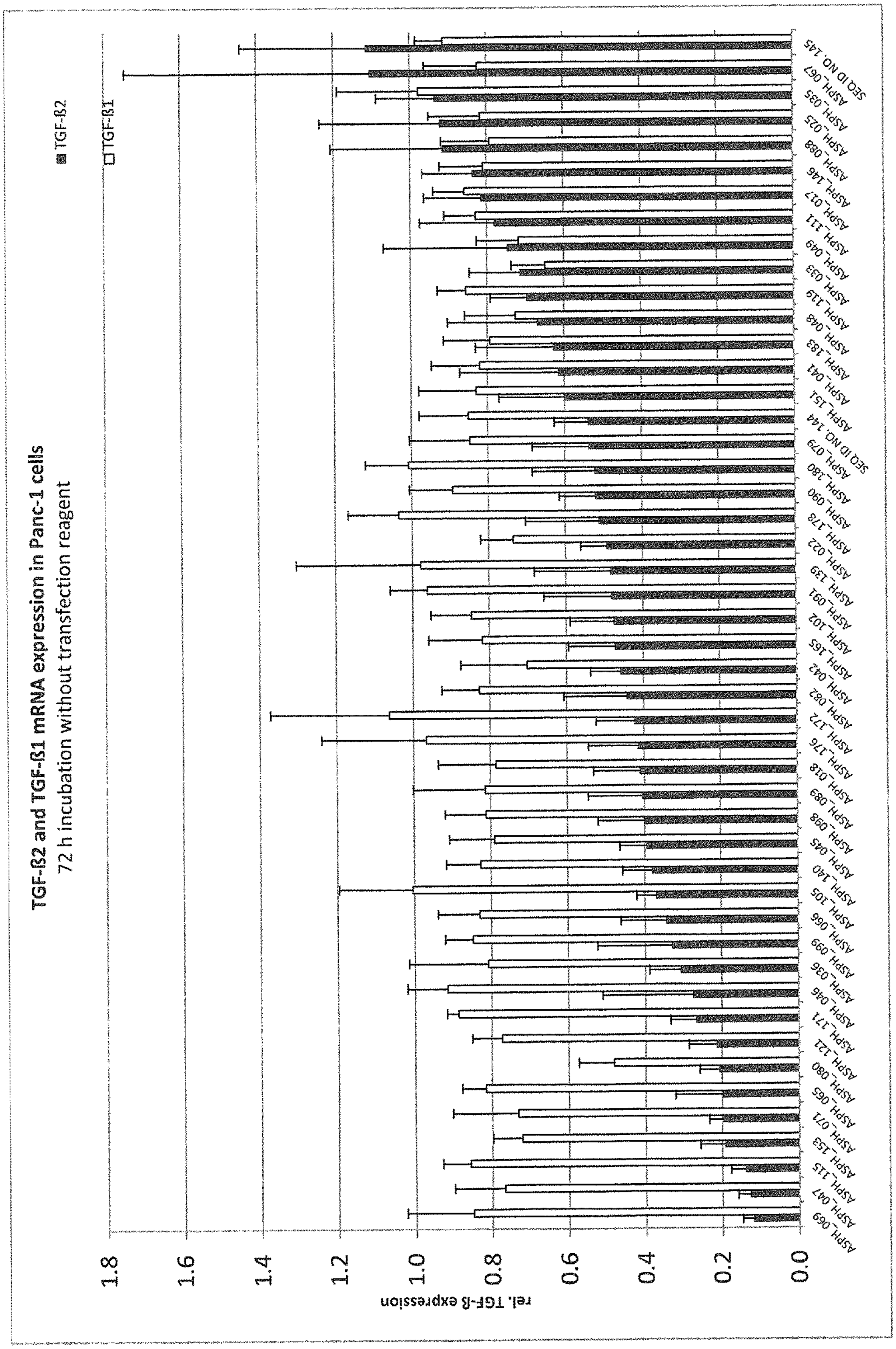

FIG. 7 shows the inhibition of the expression of TGF-beta1 and TGF-beta2 mRNA in Panc-1 cells. Panc-1 cells were treated with different modified oligonucleotides in a dose of 3.3 μM in the absence of any transfection reagent (gymnotic transfection or unassisted transfection), and the inhibition of the TGF-beta1 (white columns) and TGF-beta2 (black columns) mRNA expression was measured after 72 h. FIG. 7 presents the results for the modified oligonucleotides ASPH17, ASPH18, ASPH22, ASPH25, ASPH33, ASPH35, ASPH36, ASPH41, ASPH42, ASPH45, ASPH46, ASPH47, ASPH48, ASPH49, ASPH65, ASPH66, ASPH67, ASPH69, ASPH71, ASPH79, ASPH80, ASPH82, ASPH88, ASPH89, ASPH90, ASPH91, ASPH98, ASPH99, ASPH102, ASPH105, ASPH111, ASPH115, ASPH119, ASPH121, ASPH139, ASPH140, ASPH146, ASPH151, ASPH153, ASPH165, ASPH171, ASPH172, ASPH176, ASPH178, ASPH180, and ASPH183. Experiments are described in Example 4.

Figure 8A:
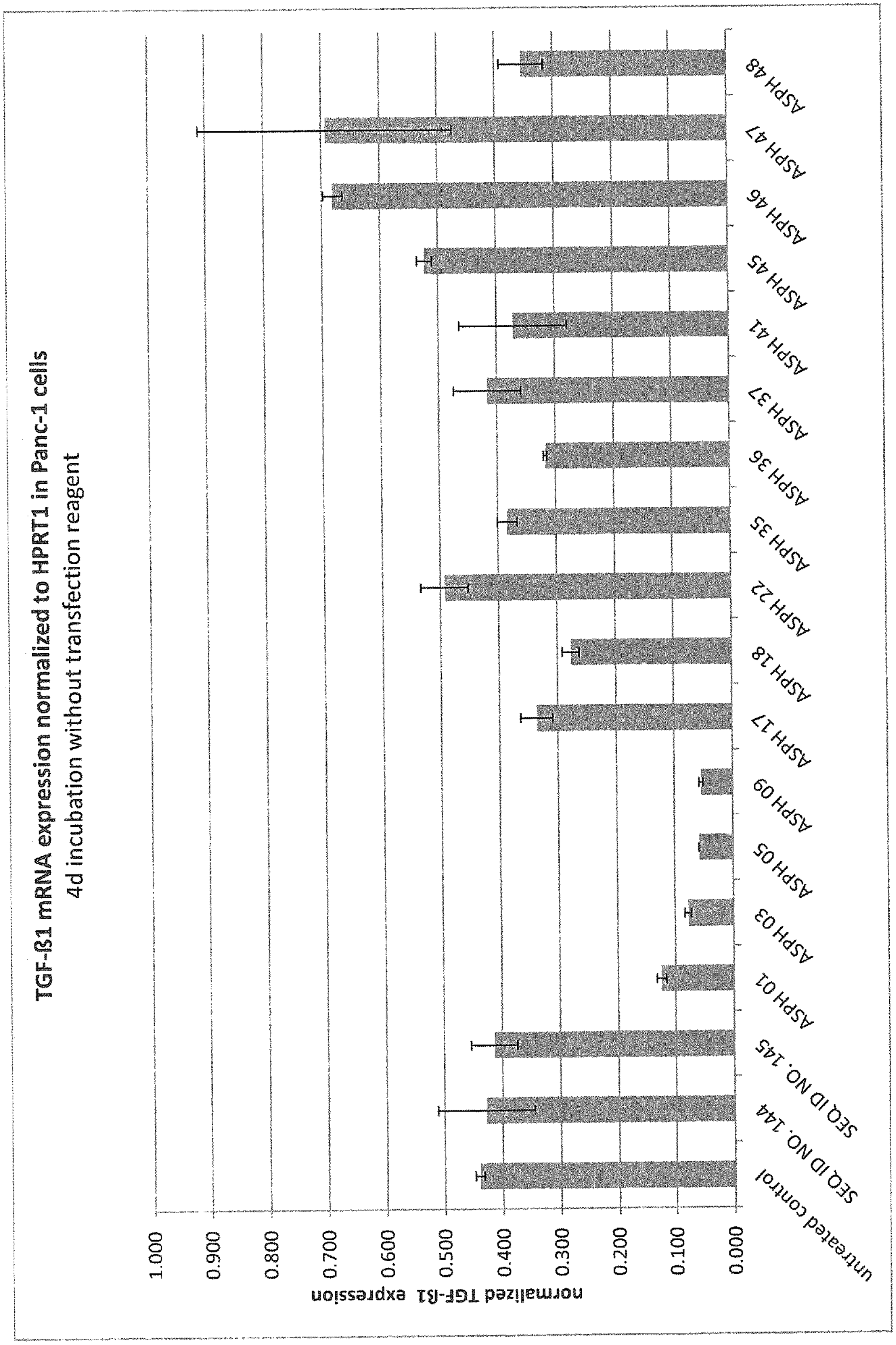
Figure 8B:
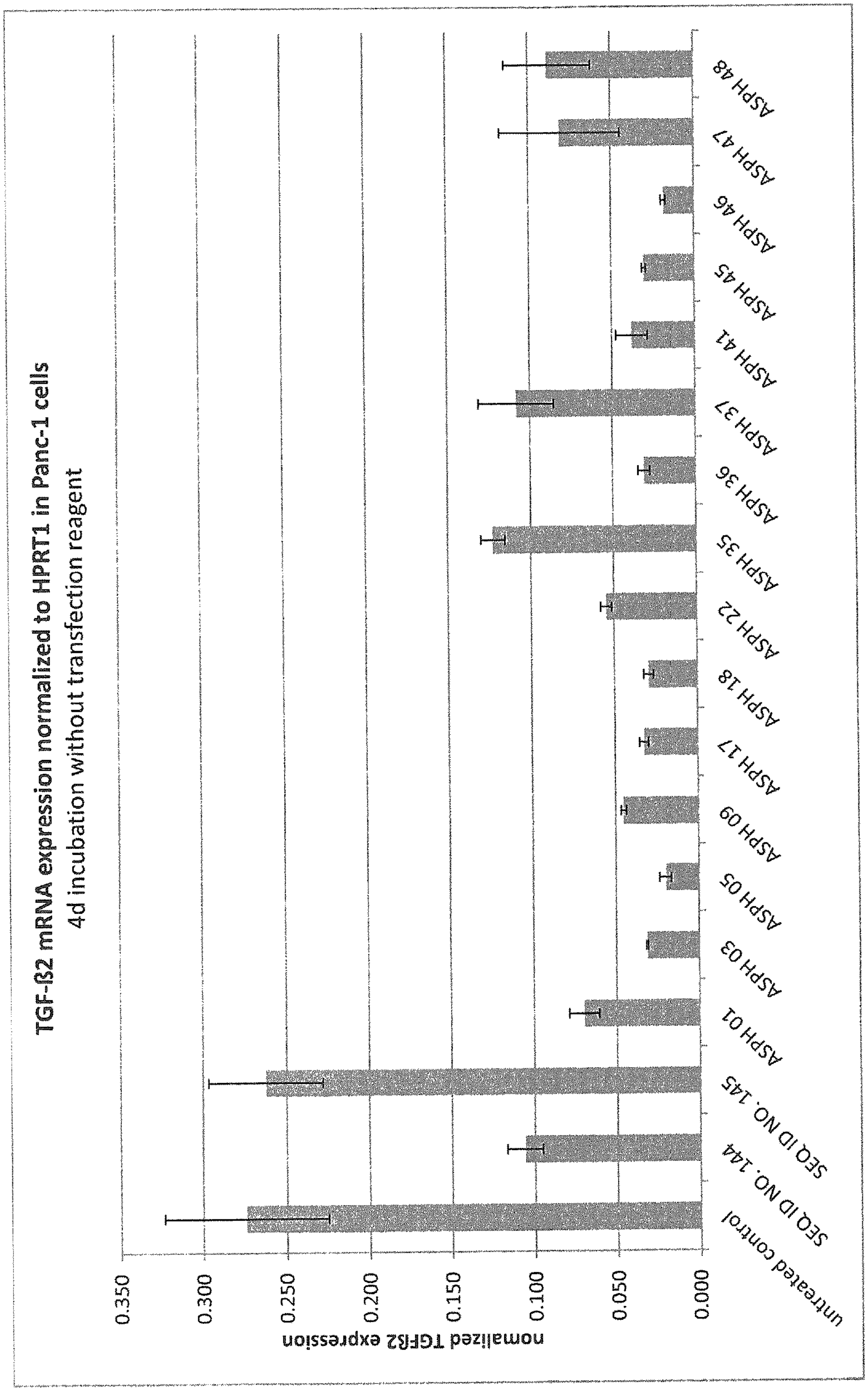
Figure 9A:
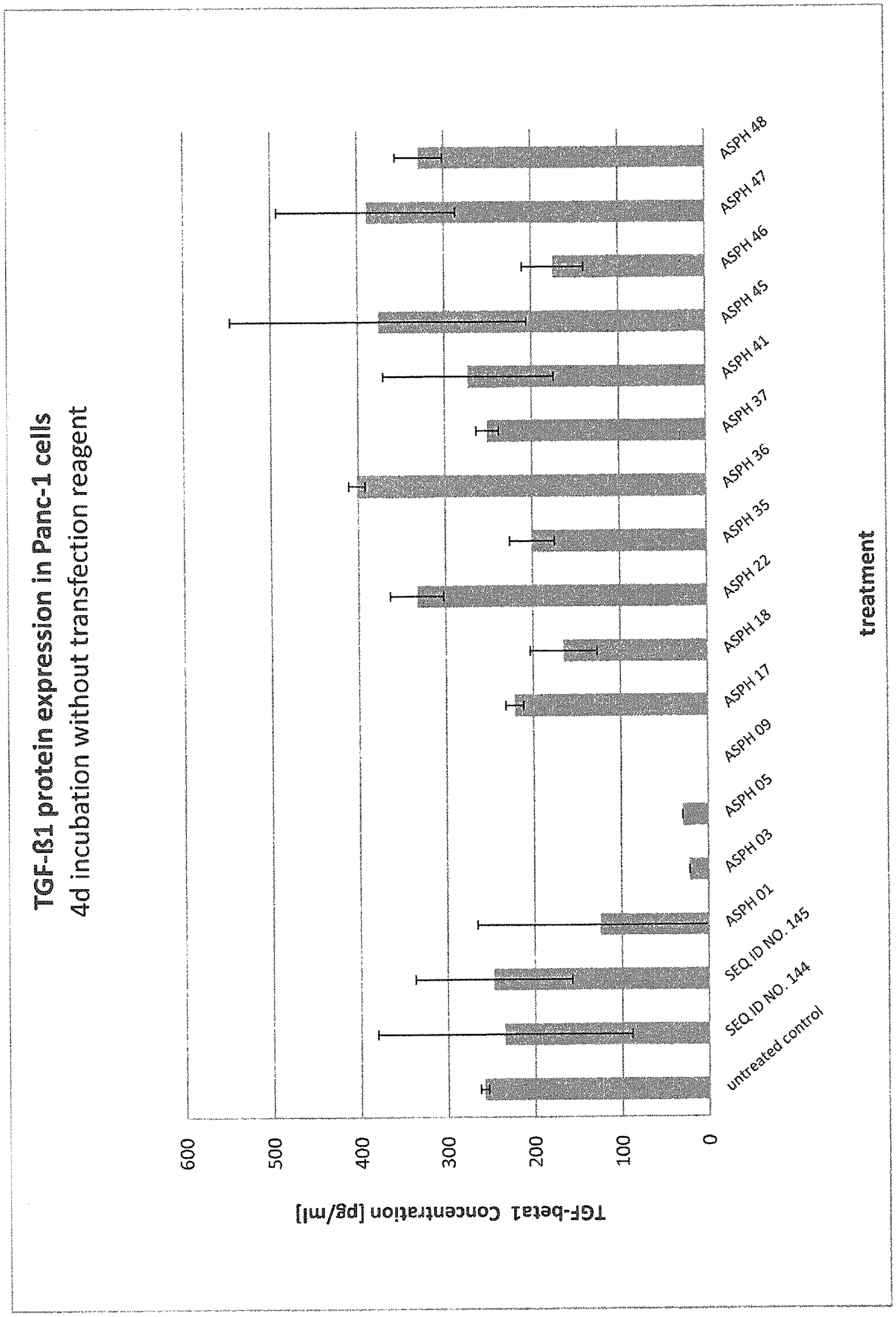
Figure 9B:
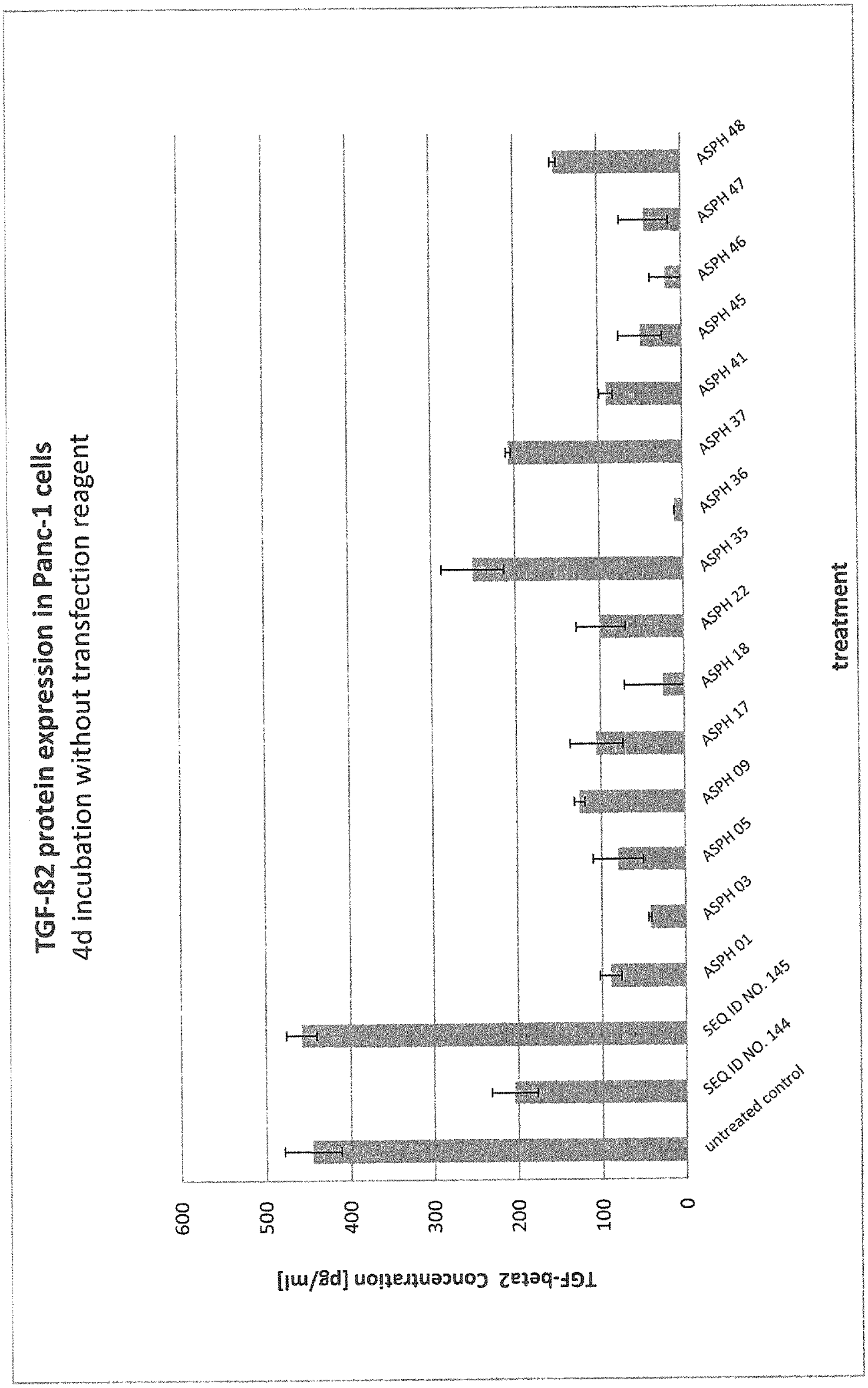

FIG. 8 and FIG. 9 present the inhibition of the expression of TGF-beta1 (FIG. 8*a*) and TGF-beta2 (FIG. 8*b*) mRNA as well as the inhibition of TGF-beta1 (FIG. 9*a*) and TGF-beta2 (FIG. 9*b*) protein in Panc-1 cells. Panc-1 cells were treated with different modified oligonucleotides in a dose of 10 μM via gymnotic transfection, i.e., in the absence of any transfecting reagent, and the inhibition of the TGF-beta1 and TGF-beta2 mRNA expression and protein was measured 4 days after transfection. FIG. 8*a*) and FIG. 8*b*) show the results for the modified oligonucleotides ASPH01, ASPH03, ASPH05, ASPH09, ASPH17, ASPH18, ASPH22, ASPH35, ASPH36, ASPH37, ASPH41, ASPH45, ASPH46, ASPH47, and ASPH48 on mRNA level, and FIG. 9*a*) and FIG. 9*b*) on protein level. Experiments are described in Example 5.

Figure 10A:
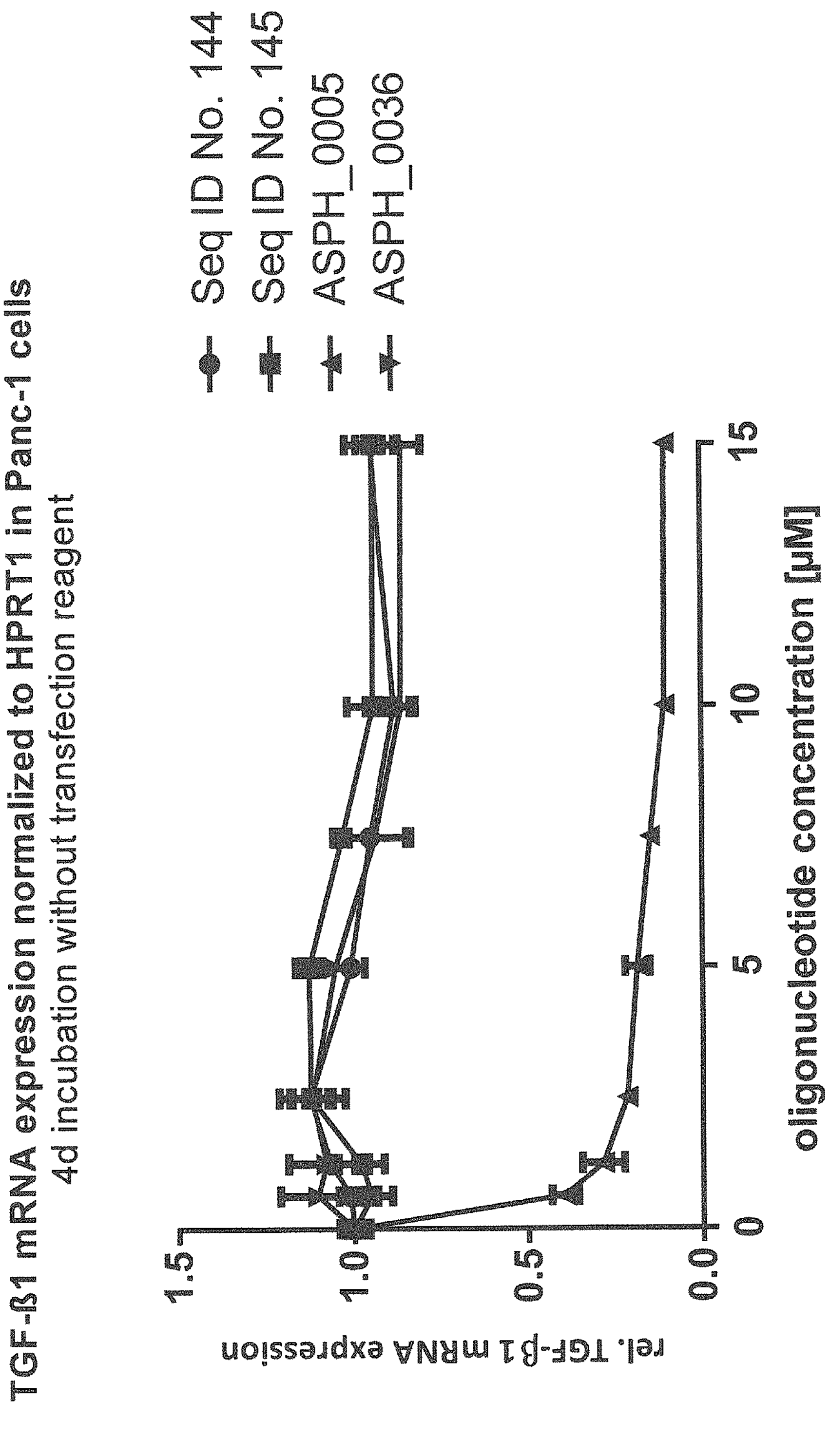
Figure 10B:
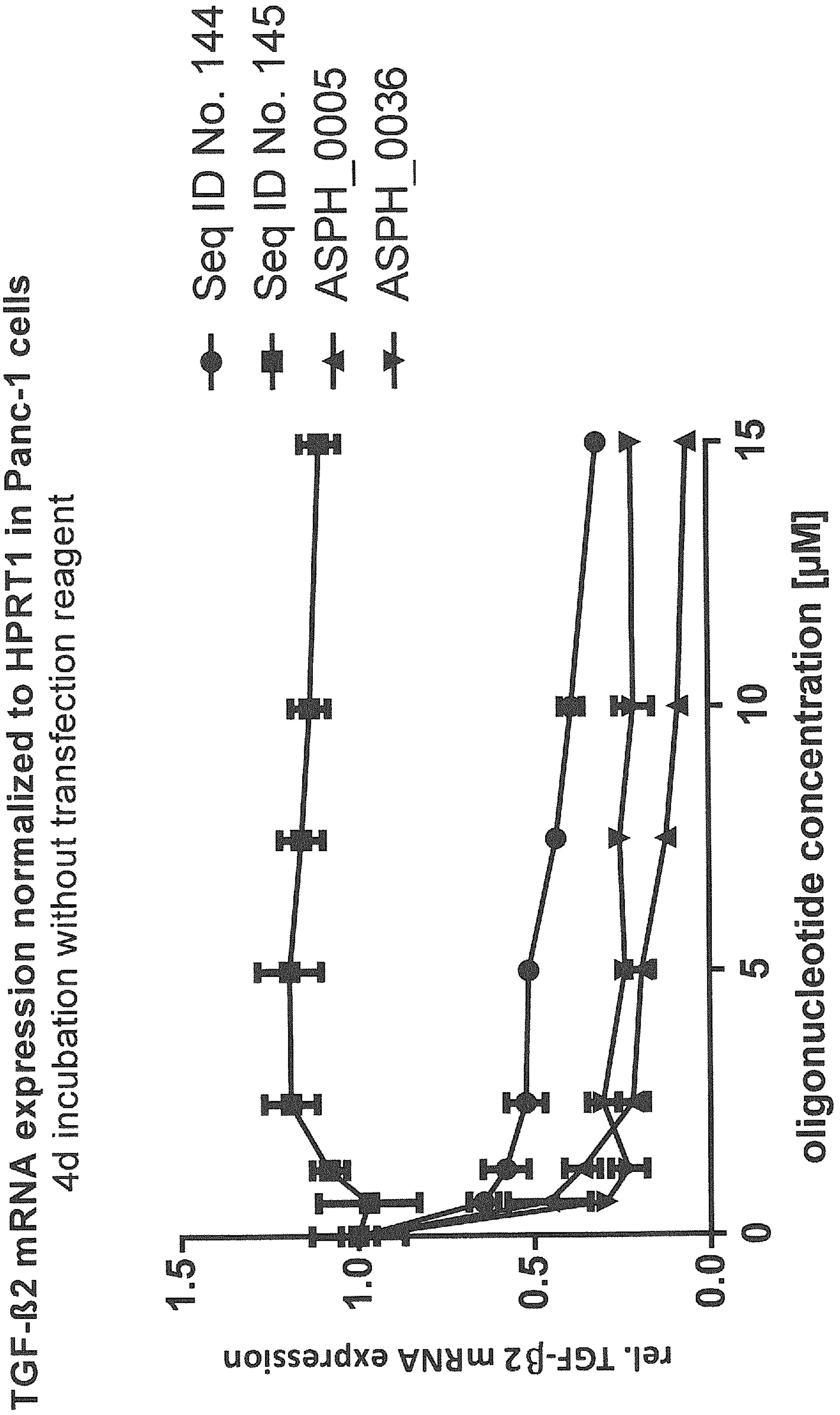

FIG. 10 depicts the dose-dependent effect of modified oligonucleotides ASPH05 and ASPH36 on TGF-beta1 and TGF-beta2 mRNA expression. Panc-1 cells were treated for 4 days with 15 μM, 10 μM, 7.5 μM, 5 μM, 2.5 μM, 1.25 μM, or 0.625 μM of either ASPH05 (dual TGF-beta1 and TGF-beta2 oligonucleotide) or ASPH36 (selective TGF-beta2 oligonucleotide) modified oligonucleotide in the absence of a transfection reagent. Remaining TGF-beta1 (FIG. 10*a*) or TGF-beta2 mRNA (FIG. 10*b*) was measured after 4 days. Experiments are described in Example 6.

Figure 11:
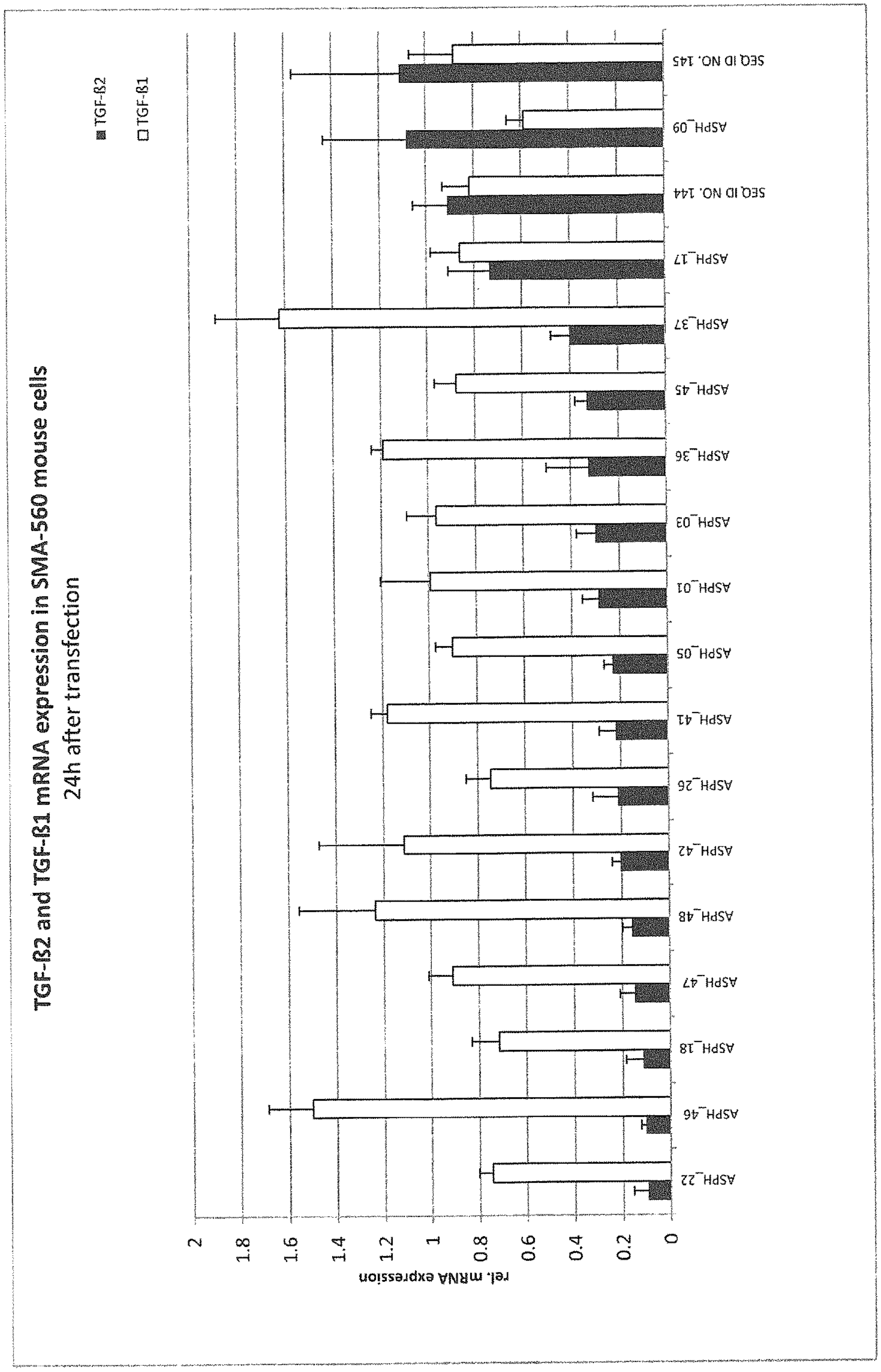

FIG. 11 shows the inhibition of the expression of TGF-beta1 and TGF-beta2 mRNA in mouse SMA-560 glioma cells. SMA-560 cells were transfected with ASPH01, ASPH03, ASPH05, ASPH09, ASPH17, ASPH18, ASPH22, ASPH26, ASPH36, ASPH37, ASPH41, ASPH42, ASPH45, ASPH46, ASPH47, or ASPH48 in a dose of 10 nM (in the presence of a transfecting agent). Inhibition of the mouse TGF-beta1 (white columns) and TGF-beta2 (black columns) mRNA expression was determined 24 h after transfection. Experiments are described in Example 7.

Figure 12:
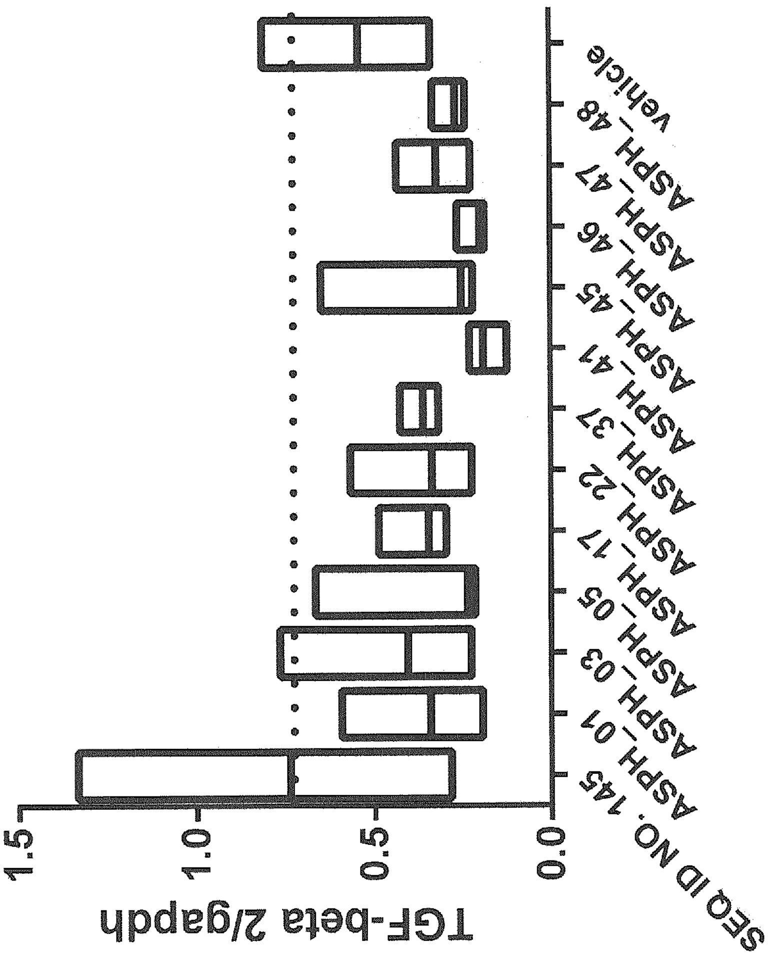

FIG. 12 presents in vivo data referring to the treatment of female athymic nude mice with ASPH01, ASPH03, ASPH05, ASPH17, ASPH22, ASPH37, ASPH41, ASPH45, ASPH46, ASPH47, or ASPH48 at 14 mg/kg body weight by subcutaneous injection for 5 consecutive days. 24 h after the last treatment, mice were sacrificed and mouse TGF-beta 2 mRNA was quantified in kidney tissue lysates. Data—representing TGF-beta2 to GAPDH mRNA ratio—are shown as a box plot in which median values and min. and max. values are presented (data expressed as n=4, except ASPH46 group n=3). Experiments are described in Example 8.

Figure 13:
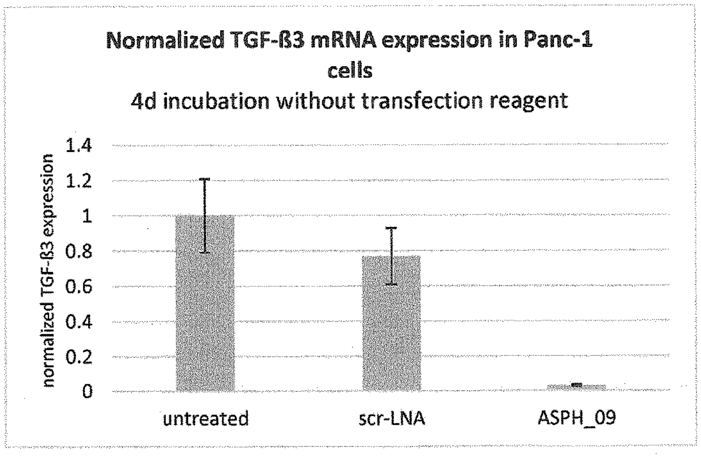

FIG. 13 shows the inhibition of the expression of TGF-beta3 mRNA in Panc-1 cells. Panc-1 cells were treated with ASPH09 in a dose of 10 μM in the absence of any transfection reagent (gymnotic transfection or unassisted transfection), and the inhibition of the TGF-beta3 mRNA expression was measured after 4 days. ASPH09 is a panspecific oliogonucleotide inhibiting the expression of TGF-beta3 as well as of TGF-beta1 and TGF-beta2 (FIGS. 8*a* and 8*b*). Experiment is described in Example 9.

Figure 14:
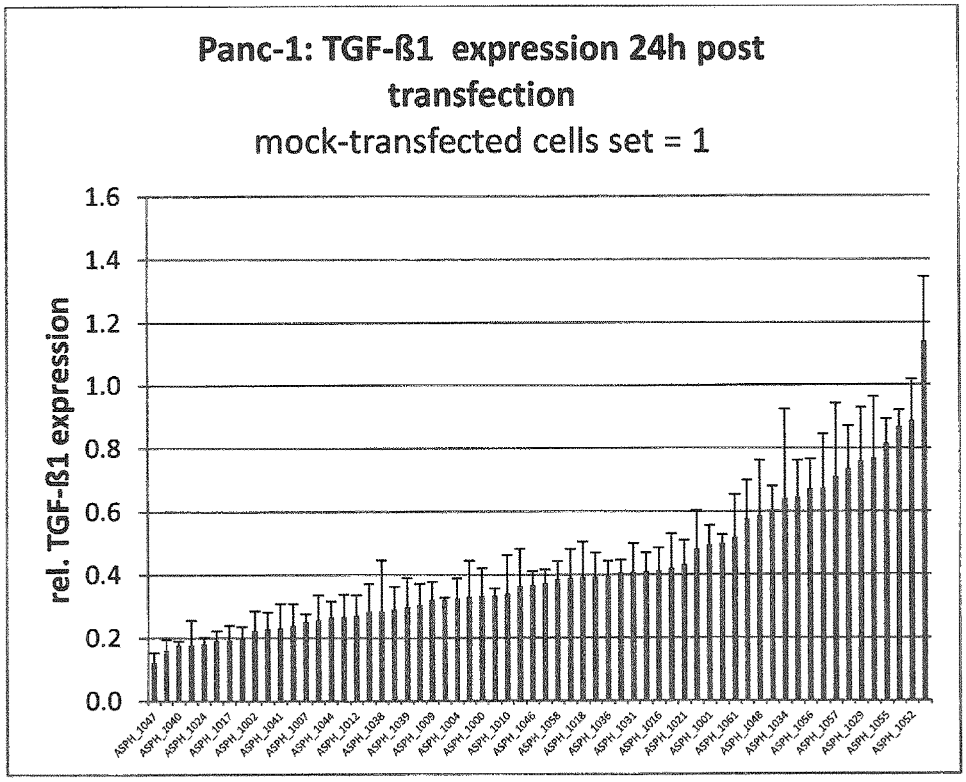

FIG. 14 depicts the inhibition of the expression of TGF-beta1 mRNA in human Panc-1 pancreatic cancer cells. Panc-1 cells were transfected with different modified oligonucleotides in a dose of 10 nM (in the presence of a transfecting agent), and the inhibition of the TGF-beta1 mRNA expression was measured 24 h after transfection.

FIG. 14 refers to the results for the modified oligonucleotides ASPH05, ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH 1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1054, ASPH1055, ASPH1056, ASPH1057, ASPH1058, ASPH1059, ASPH1060, and ASPH1061. Experiments are described in Example 12.

Figure 15:
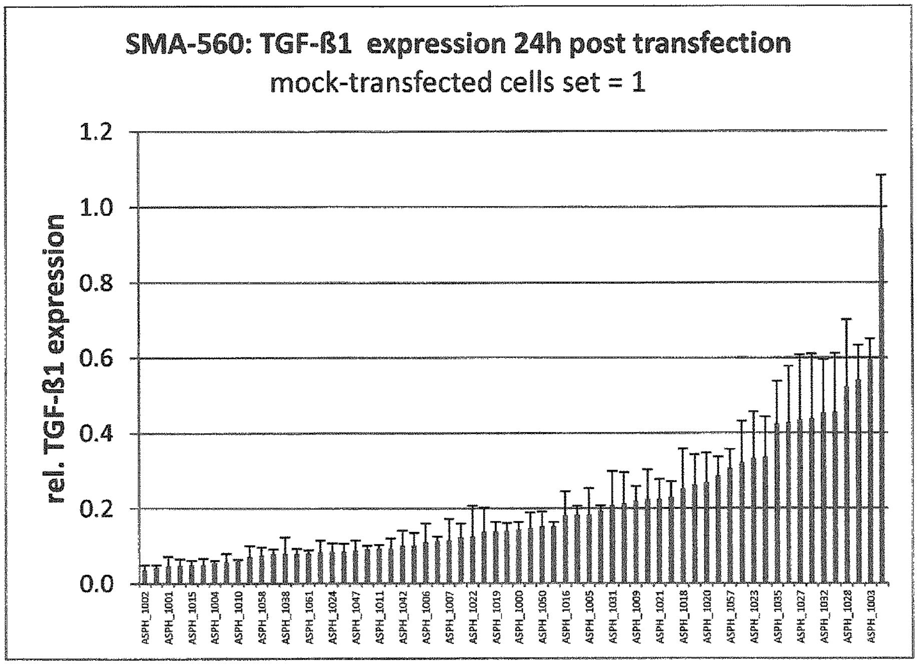

FIG. 15 shows the inhibition of the expression of TGF-beta1 mRNA in mouse SMA-560 glioma cells. The cells were transfected with different modified oligonucleotides in a dose of 10 nM (in the presence of a transfecting agent), and the inhibition of the TGF-beta1 mRNA expression was measured 24 h after transfection. FIG. 15 refers to the results for the modified oligonucleotides ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH 1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, and ASPH1062. Experiments are described in Example 13.

Figure 16:
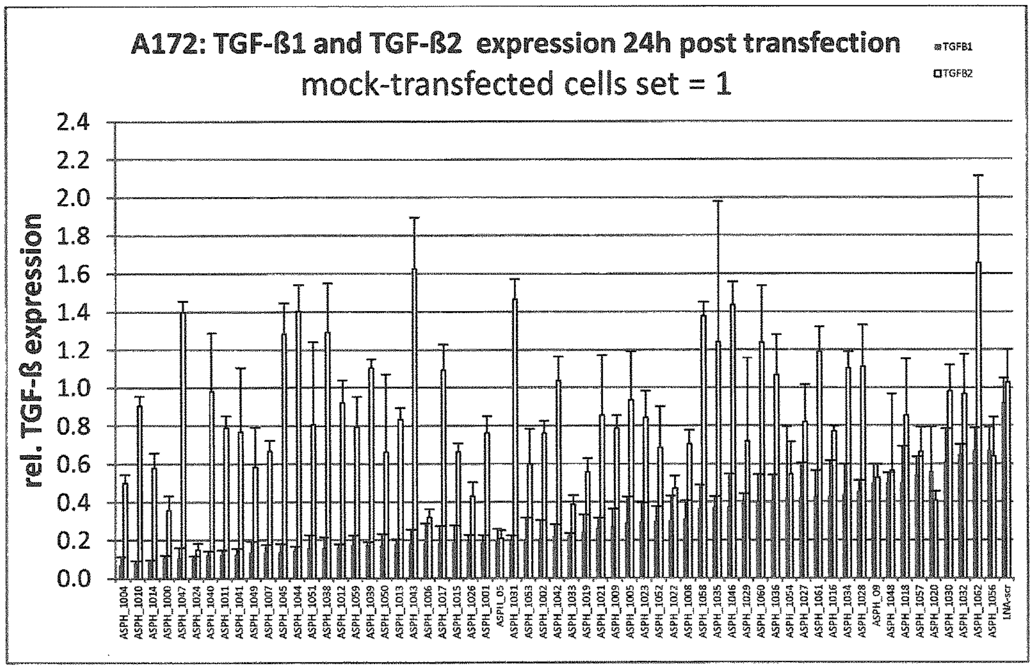

FIG. 16 depicts the inhibition of the expression of TGF-beta1 and TGF-beta2 mRNA in human A172 cells. The cells were transfected with different modified oligonucleotides in a dose of 10 nM (in the presence of a transfecting agent), and the inhibition of the TGF-beta1 and TGF-beta2 mRNA expression was measured 24 h after transfection. FIG. 16 refers to the results for the modified oligonucleotides ASPH05, ASPH09, ASPH1000, ASPH1001, ASPH1002, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1056, ASPH1057, ASPH1058, ASPH1059, ASPH1060, ASPH1061, and ASPH1062. Experiments are described in Example 14.

Figure 17:
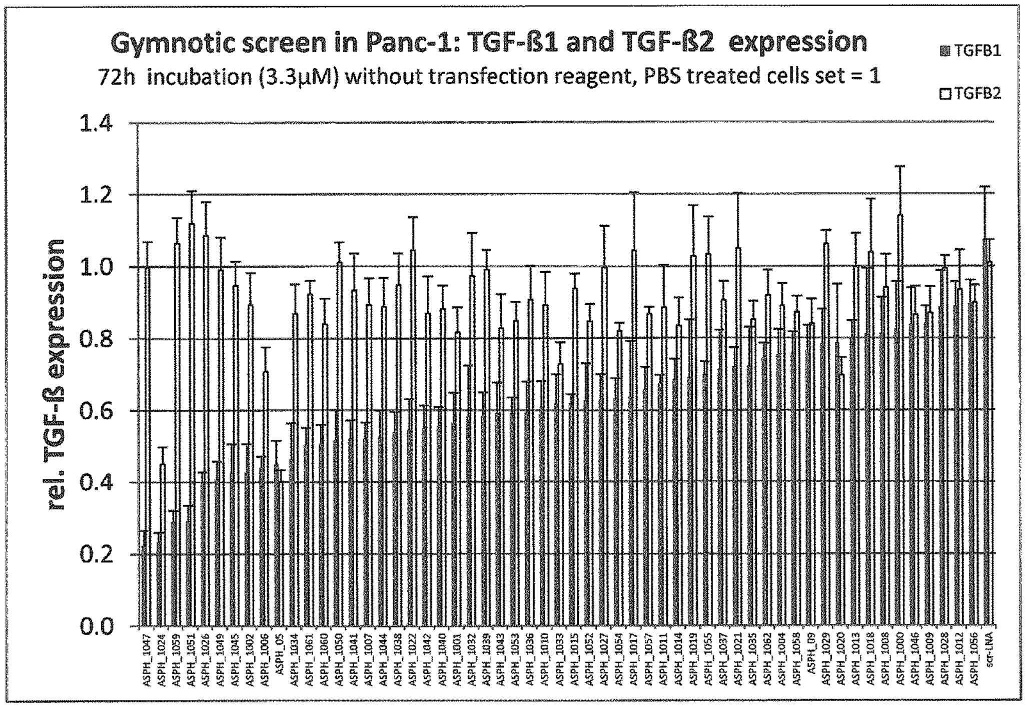

FIG. 17 shows the inhibition of the expression of TGF-beta1 and TGF-beta2 mRNA in Panc-1 cells. Panc-1 cells were treated with different modified oligonucleotides in a dose of 3.3 μM in the absence of any transfection reagent (gymnotic transfection or unassisted transfection or gymnotic delivery), and the inhibition of the TGF-beta1 (black columns) and TGF-beta2 (white columns) mRNA expression was measured after 72 h. FIG. 17 refers to the results for the modified oligonucleotides ASPH05, ASPH09, ASPH1000, ASPH1001, ASPH1002, ASPH1004, ASPH1006, ASPH1007, ASPH1008, ASPH1009, ASPH1010, ASPH1011, ASPH1012, ASPH1013, ASPH1014, ASPH1015, ASPH1017, ASPH1018, ASPH1019, ASPH1020, ASPH1021, ASPH1022, ASPH1024, ASPH1026, ASPH1027, ASPH1028, ASPH1029, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, and ASPH1062. Experiments are described in Example 15.

Figure 18:
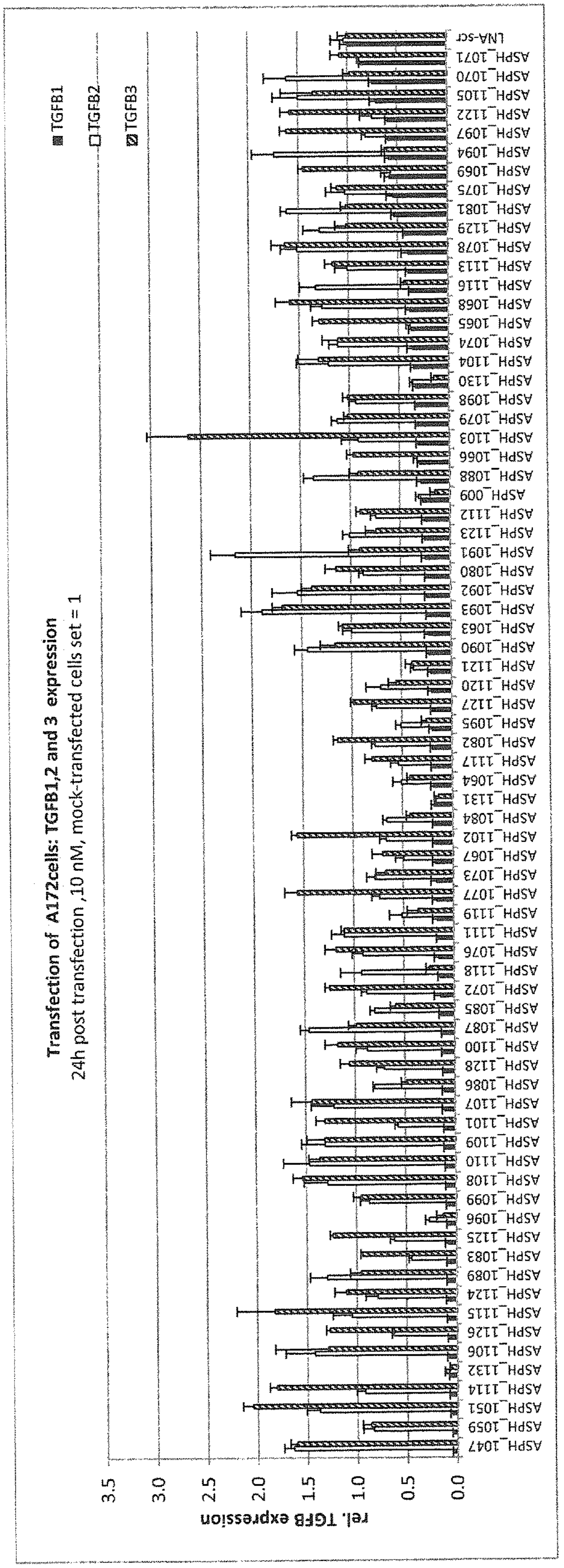

FIG. 18 depicts the inhibition of the expression of TGF-beta1, TGF-beta2 and TGF-beta3 mRNA in human A172 cells. The cells were transfected with different modified oligonucleotides in a dose of 10 nM (in the presence of a transfecting agent), and the inhibition of the TGF-beta1 (black column), TGF-beta2 (white column) and TGF-beta3 (striped column) mRNA expression was measured 24 h after transfection. FIG. 18 refers to the results for the modified oligonucleotides ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132. Experiments are described in Example 16.

Figure 19A:
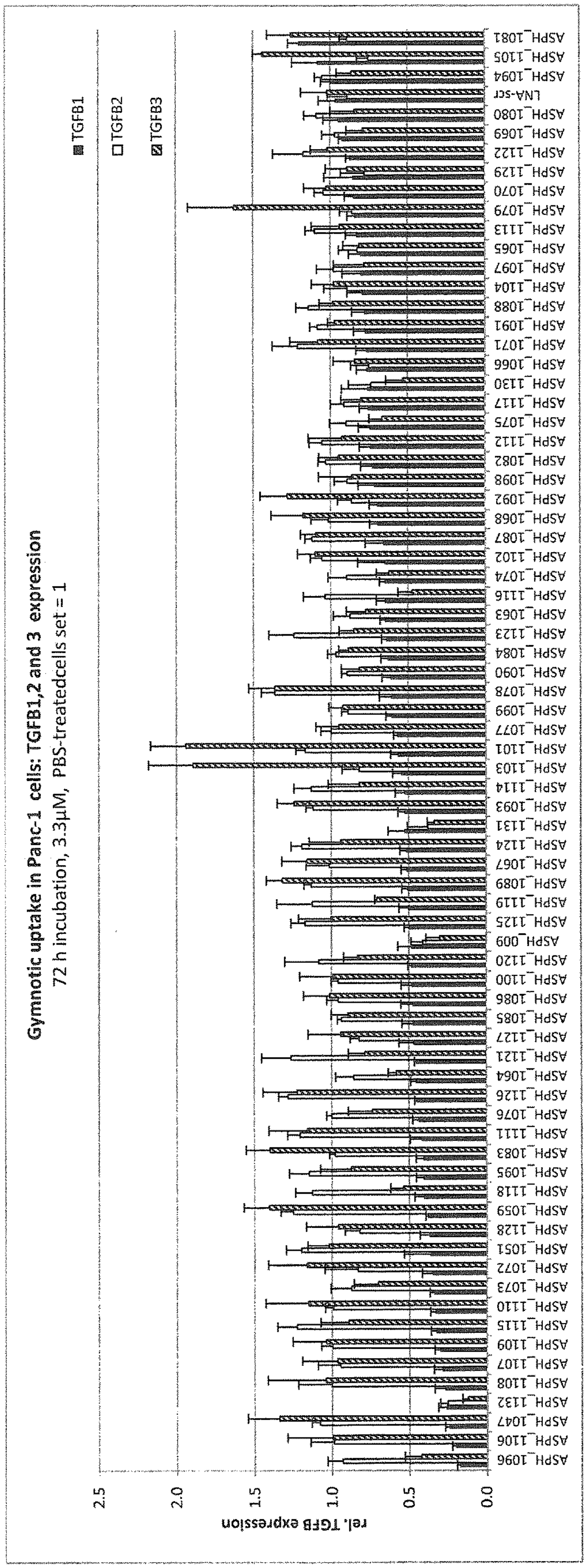
Figure 19B:
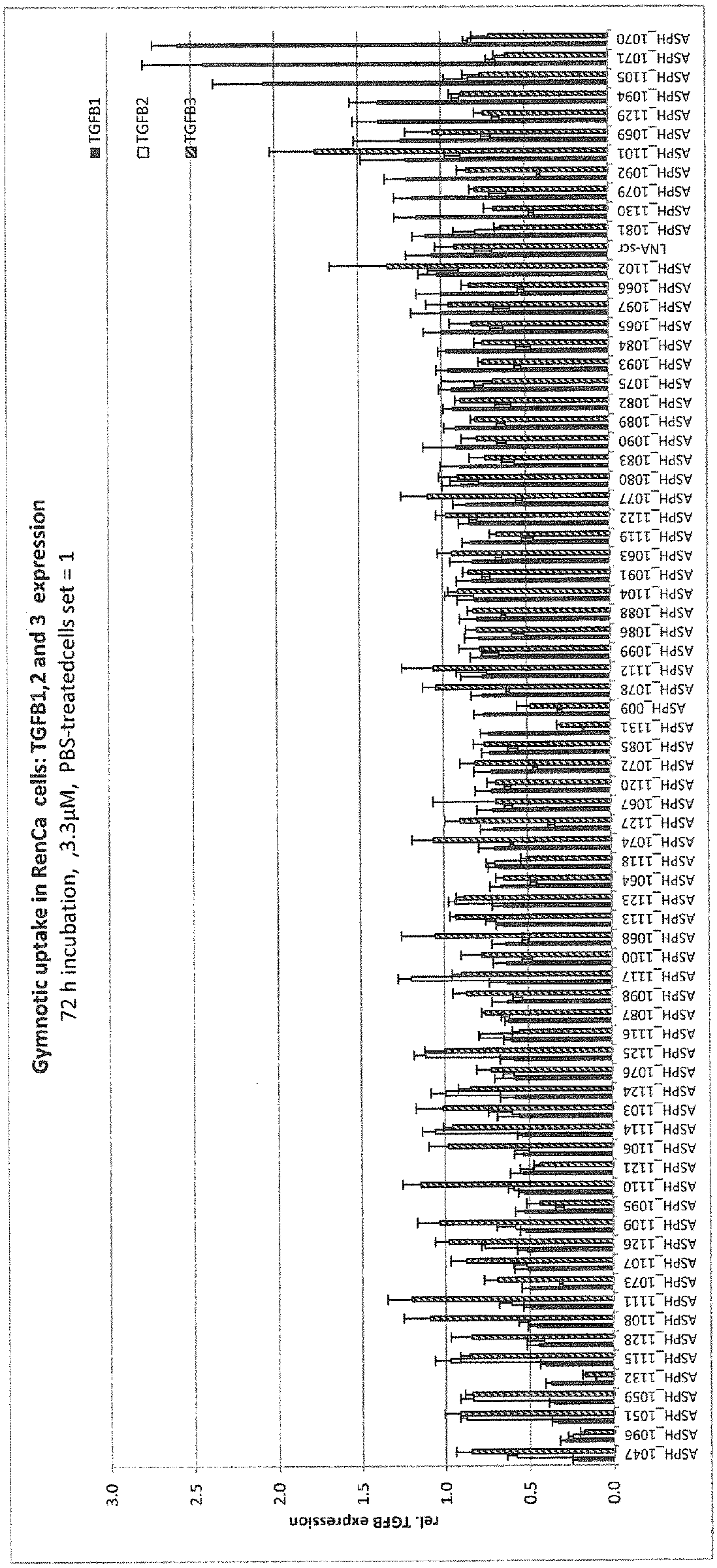

FIG. 19*a* shows the inhibition of the expression of TGF-beta1, TGF-beta2 and TGF-beta3 mRNA in human Panc-1 and RenCa cells. The cells were transfected with different modified oligonucleotides in a dose dose of 3.3 μM in the absence of any transfection reagent (gymnotic transfection or unassisted transfection or gymnotic delivery), and the inhibition of the TGF-beta1 (black column), TGF-beta2 (white column) and TGF-beta3 (striped column) mRNA expression was measured 72 h after transfection. FIG. 19*a* refers to the results for the modified oligonucleotides ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132. FIG. 19*b* presents the inhibiting effect of these oligonucleotides in RenCa cells.

FIG. 20 presents a sequence alignment of ASPH1024 and ASPH1096, which are 100% homologous to a human sequence of TGF-beta1, with a human sequence of TGF-beta2 and TGF-beta3, respectively. ASPH1024 has three mismatches with the human sequence of TGF-beta2 (FIG. 20*a*) and two mismatches with human sequence of TGF-beta3 (FIG. 20*b*). ASPH1096 has one mismatch with the human sequence of TGF-beta2 (FIG. 20*a*), and one mismatch with the human sequence of TGF-beta3 (FIG. 20*b*). Both oligonucleotides show inhibition of different human TGF-beta isoforms (TGF-beta1, TGF-beta2, and TGF-beta3). For example ASPH1024 inhibits the expression and activity of TGF-beta1 and TGF-beta2 (see FIG. 17) and ASPH1096 inhibits the expression and activity of TGF-beta1, TGF-beta2 and TGF-beta3 as depicted in FIG. 18 for example. ASPH009, which is 100% homologous to the human sequence of TGF-beta1, TGF-beta2, and TGF-beta3 was used as a control.

FIG. 21 shows a sequence alignment of ASPH1131 and ASPH1132, which are 100% homologous to a human sequence of TGF-beta1 and TGFβbeta3, with a human sequence of TGF-beta2. Each of ASPH1131 and ASPH1132 has one mismatch with the human sequence of TGF-beta2. Both oligonucleotides strongly inhibit the expression of all three human isoforms as depicted in FIG. 18 for example.

FIG. 22 depicts a sequence alignment of ASPH1131 and ASPH1132, which are 100% homologous to a murine sequence of TGF-beta1 and TGFbeta3, with a murine sequence of TGF-beta2. Each of ASPH1131 and ASPH1132 has two mismatches with the murine sequence of TGF-beta2. While ASPH1131 potently inhibits murine TGF-beta2 and TGF-beta3, ASPH1132 very potently suppresses all murine TGF-beta isoforms as depicted in FIG. 19*b* for example.

FIG. 23 shows TGF-beta2 mRNA expression in the kidney of mice bearing subcutaneous human pancreatic carcinoma Panc-1 tumors. Mice were treated with 1, 3, 10, and 30 mg/kg of ASPH47 after indicated treatment schedules for 5 days: Q1Dx1-d6 (single SC injection, termination 5 days later), Q1Dx5-d6 (daily SC injection for 5 days, termination 24 hours later), and Q1Dx5-d10 (daily SC injection for 5 days, termination 5 days later). TGF-beta2 and house-keeping gene GAPDH mRNA expression was detected by bDNA assay. Data—representing TGF-beta2 to GAPDH mRNA ratio—are shown as a box plot in which median values and min. and max. values are presented (data expressed as n=10, except n=9 for vehicle and 3 mg/kg Q1Dx1 d6 groups).

FIG. 24 depicts TGF-beta2 mRNA expression in the kidneys of mice bearing human pancreatic carcinoma Panc-1 tumors. Mice were treated with subcutaneous injections of various oligonucleotides for 5 consecutive days using indicated treatment doses: daily injection of 1, 5, 15 or 50 mg/kg oligonucleotides for five consecutive days. TGF-beta2 and house-keeping gene GAPDH mRNA expression was detected by bDNA. Data—representing TGF-beta2 to GAPDH mRNA ratio—are shown as a box plot in which median values and min. and max. values are presented (data expressed as n=5).

FIG. 25 presents TGF-beta2 mRNA expression in subcutaneous human renal cell carcinomas 786-O tumors. Mice were treated with a daily injection of 50 mg/kg oligonucleotides for five consecutive days. The tumors were collected 24 hours after the last treatment and snap frozen. TGF-beta2 and house-keeping gene GAPDH mRNA expression was detected by bDNA assay. Data—representing TGF-beta2 to GAPDH mRNA ratio—are shown as a box plot in which median values and min. and max. values are presented (data expressed as n=10, except for ASPH71 group n=9).

FIG. 26 depicts the inhibiting effect of oligonucleotides of the present invention on the expression of TGF-beta1 and TGF-beta2 protein. Panc-1 cells were transfected with 20, 6.67, 2.22, 0.74, 0.25, 0.08 or 0.009 μM of the modified oligonucleotides ASPH47 (FIG. 26*a*), ASPH1047 (FIG. 26*b*), ASPH1106 (FIG. 26*c*), ASPH1132 (FIG. 26*d*), or ASPH47 in combination with ASPH1047 (FIG. 26*e*). Negative control is the scrambled oligonucleotide (scrLNA) of SEQ ID No. 145 (FIG. 26*f*) in concentrations of 40, 13.33, 4.44, 1.48, 0.49, 0.16, 0.05, or 0.02 μM. TGF-beta1 and TGF-beta2 protein levels in cell supernatants were determined by ELISA, wherein results for TGF-beta1 are indicated in diamonds, and results for TGF-beta2 in squares.

FIG. 27 shows the inhibition of the expression of TGF-beta1, TGF-beta2 and TGF-beta3 mRNA in human Panc-1 cells and mouse RenCa cells. Panc-1 and RenCa cells were treated with different modified oligonucleotides in a dose of 1.1 μM in the absence of any transfection reagent (gymnotic transfection or unassisted transfection or gymnotic delivery), and the inhibition of the TGF-beta1 (black columns), TGF-beta2 (white columns), and TGF-beta3 (striped columns) mRNA expression was measured after 72 h. FIG. 17 refers to the results for the modified oligonucleotides ASPH190, ASPH191, ASPH192, ASPH193, ASPH194, ASPH195, ASPH196, ASPH197, ASPH198, ASPH199, ASPH200, ASPH201, ASPH202, ASPH203, ASPH204, ASPH205, ASPH206, ASPH207, ASPH208, ASPH209, ASPH210, ASPH211, ASPH212, ASPH213, ASPH214, ASPH215, ASPH216, ASPH217, ASPH218, ASPH219, ASPH220, ASPH221, ASPH222, and ASPH223, respectively. FIG. 27*a* presents the inhibitory effect of these TGF-beta oligonucleotides in Panc-1 cells and FIG. 27*b* in RenCa cells.

Figure 28A:
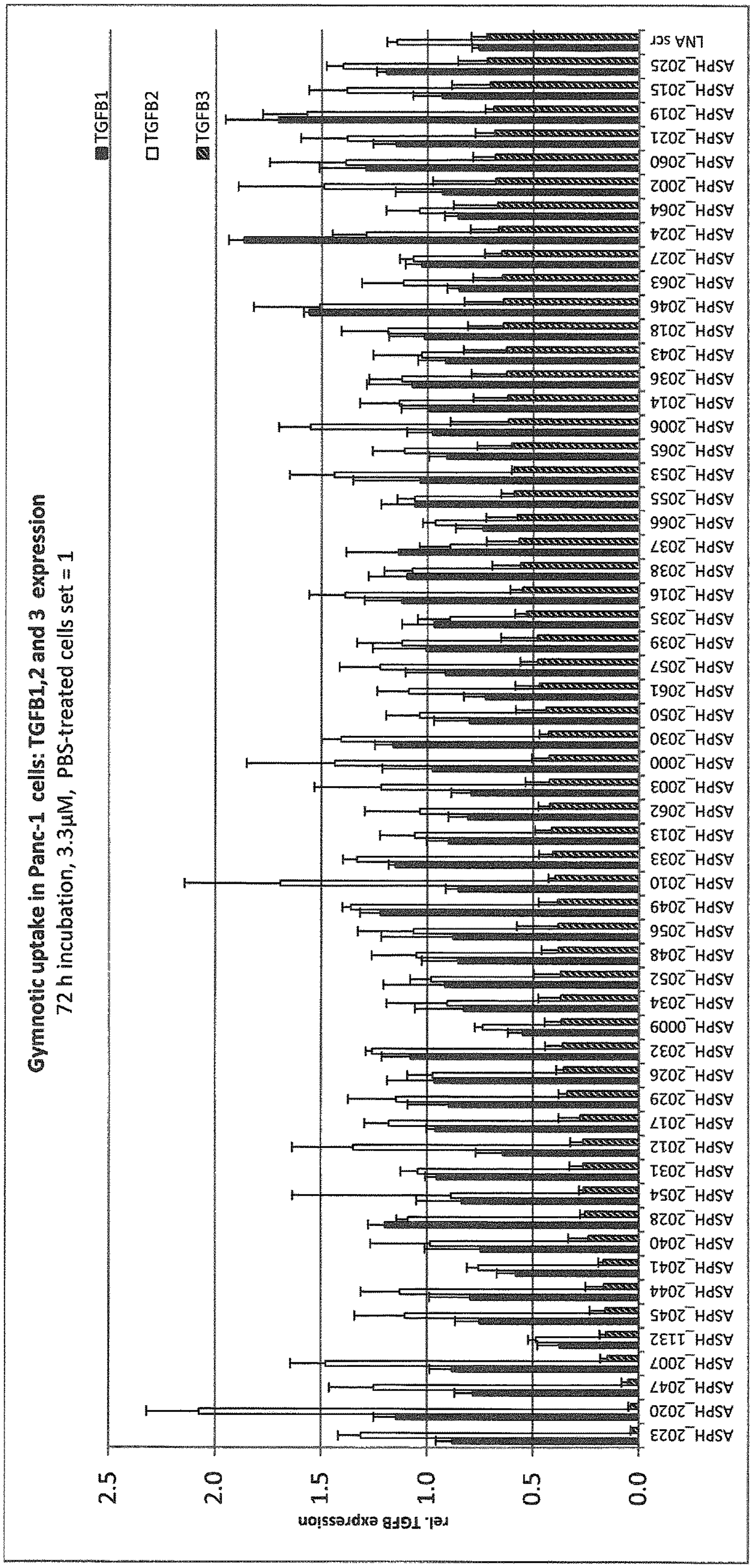
Figure 28B:
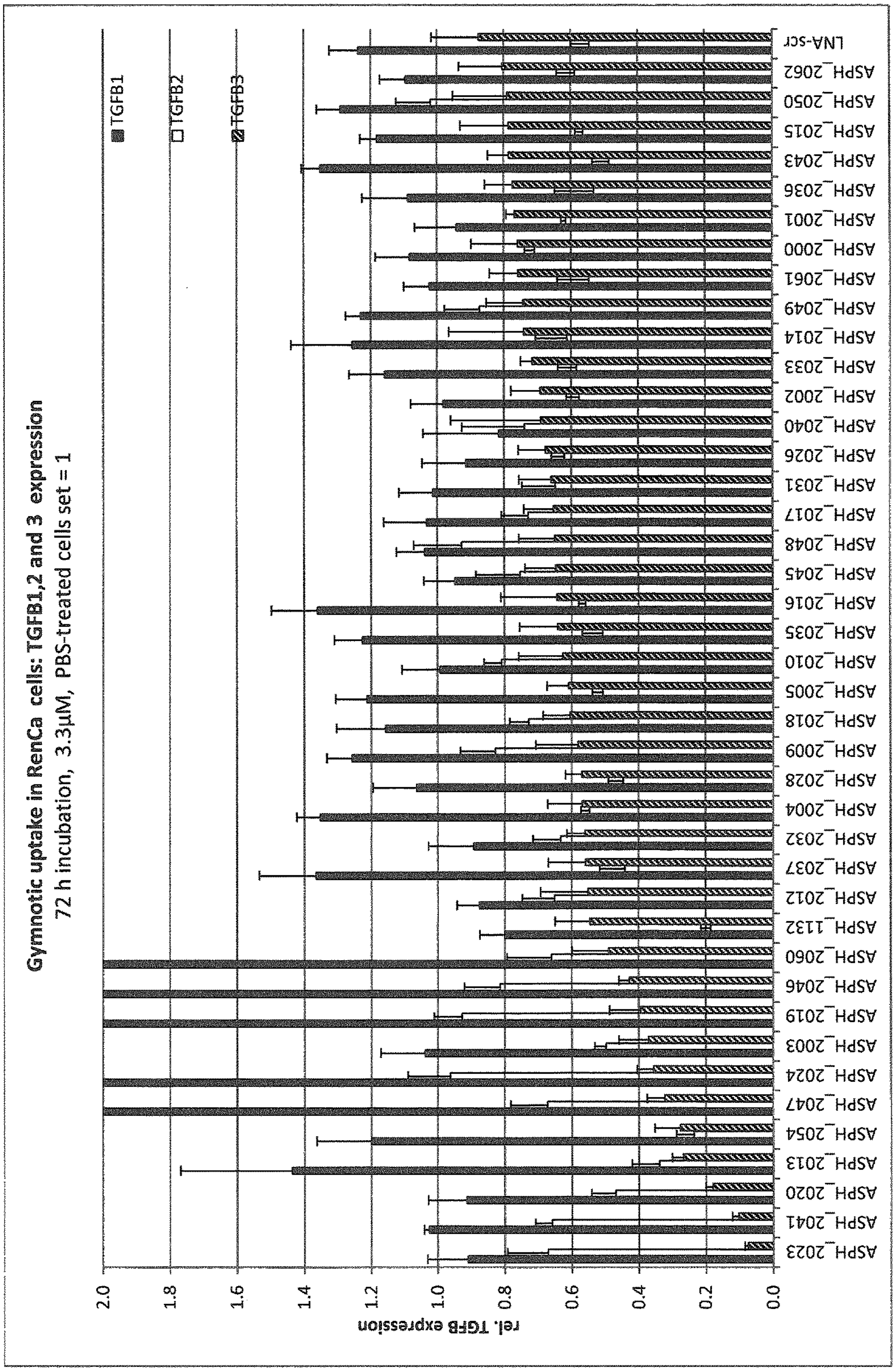

FIG. 28 presents the inhibiting effect of oligonucleotides of the present invention on the expression of TGF-beta1, TGF-beta2, and TGF-beta3. Panc-1 cells (FIG. 28*a*) or RenCa cells (FIG. 28*b*) were transfected with 3.3 μM of different TGF-beta specific oligonucleotides in the absence of a transfecting agent. The expression of TGF-beta1 (black column), TGF-beta2 (white column) and TGF-beta3 (striped column) mRNA was determined 72 h after transfection.

FIG. 29 depicts the the inhibiting effect of oligonucleotides of the present invention on the expression of TGF-beta1, TGF-beta2, and TGF-beta3. A172 glioma cells were transfected with 10 nM of different TGF-beta specific oligonucleotides in the presence of transfecting agent. The expression of TGF-beta1 (black column), TGF-beta2 (white column) and TGF-beta3 (striped column) mRNA was determined 24 h after transfection.

FIGS. 30*a* and 30*b* present a compared analysis of time-dependent plasma (30*a*) and kidney (30*b*) concentration (PK profiles; with values expressed in μg/mL or μg/gr) and downregulation of TGF-β2 mRNA (PD profile) in kidney following single subcutaneous bolus administration of 50 mg/kg of ASPH_0047 to Balb/c mice.

FIG. 31 depicts TGF-β2 mRNA downregulation in established subcutaneous tumors (FIG. 30A-D) or kidney (FIG. 30E-F) in immunodeficient mouse following subcutaneous repeated administration of ASPH_0047 or control oligonucleotide. TGF-beta2 and GAPDH mRNA expression was detected by bDNA. Results are expressed as TGF-beta2/GAPDH mRNA ratio, and each individual tested sample is represented with line indicating median values.

FIG. 32 shows the effect of systemic treatment of Balb/c mice with ASPH_0047 (selective TGF-b2 antisense oligonucleotide) on lung metastasis in orthotopic and in i.v. mouse Renca renal carcinoma model. Level of lung metastasis was determined by either number of metastasis or based on lung weight. Results are shown as a box plot in which median values, upper and lower quartiles, and $90^{th}$ and $10^{th}$ percentiles are presented.

FIG. 33 presents human Panc-1 pancreatic cancer cells were treated with 3.3 μM of the indicated oligonucleotides in the absence of transfecting agent (gymnotic transfection or gymnotic delivery). The expression of TGF-beta1 (black column), TGF-beta2 (white column) and TGF-beta3 (striped column) mRNA was determined 72 h after transfection.

FIG. 34 depicts the effect of systemic treatment of Balb/c mice with ASPH_0047 on lung metastasis in orthotopic mouse 4T1 mammary carcinoma model. Data for each individual animal is represented with median values indicated as bold black line.

Detailed Description

The present invention is directed to oligonucleotides, in particular antisense oligonucleotides, which comprise at least one modified nucleotide and are suitable to interact with TGF-beta mRNA for use in a method for preventing and/or treating an ophthalmic disease such as dry eye, glaucoma, posterior capsule opacification, retinoblastoma or choroidcarcinoma. The oligonucleotides comprise or consist of 10 to 20, more preferred 12 to 18 nucleotides of the TGF-beta2 nucleic acid according to SEQ ID NO. 2 or of the TGF-beta1 nucleic acid according to SEQ ID NO. 1, or of the nucleic acid sequence of TGF-beta3 nucleic acid according to SEQ ID NO. 3. Most preferred the oligonucleotide comprises or consists of 12, 13, 14, 15, 16, 17, or 18 nucleotides. The oligonucleotides are preferably selected from the region of nucleic acid no. 1380 to 1510 (preferably no. 1380 to 1450 and/or no. 1480 to 1510), 1660 to 1680, or 2390 to 2410 of SEQ ID NO. 2. The oligonucleotide is a single or double stranded RNA or DNA, including siRNA, microRNA, apatmer or spiegelmer. Preferably, the oligonucleotide is an antisense oligonucleotide.

A nucleotide forms the building block of an oligonucleotide, and is for example composed of a nucleobase (nitrogenous base, e.g., purine or pyrimidine), a five-carbon sugar (e.g., ribose, 2-deoxyribose, arabinose, xylose, lyxose, allose, altorse, glucose, mannose, gulose, idose, galactose, talose or stabilized modifications of those sugars), and one or more phosphate groups. Examples of modified phosphate groups are phosphorothioate or methylphosphonate. Each compound of the nucleotide is modifiable, and is naturally occurring or none naturally occurring. The latter are for example locked nucleic acid (LNA), a 2'-O,4'-C-ethylene-bridged nucleic acid (ENA), polyalkylene oxide- (such as triethylene glycol (TEG)), 2'-fluoro, 2'-O-methoxy and 2'-O-methyl modified nucleotides as described for example by Freier & Altmann (Nucl. Acid Res., 1997, 25, 4429-4443) and Uhlmann (Curr. Opinion in Drug & Development (2000, 3 (2): 293-213)), which are shown in FIG. 4.

A LNA is a modified RNA nucleotide, wherein the ribose moiety is modified with an extra bridge connecting the 2' oxygen and 4' carbon (2'-4'ribonucleoside). The bridge “locks” the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and are mixable and combineable, respectively, with (unmodified) DNA or RNA residues in the oligonucleotide.

The oligonucleotides of the present invention, i.e., modified oligonucleotides, comprise at least one modified nucleotide, preferably LNA and/or ENA, at the 5'- and/or 3'-end of the oligonucleotide. In a preferred embodiment, the oligonucleotide comprises 1, 2, 3, or 4 LNAs or ENAs at the 5'-end, and 1, 2, 3, or 4 LNAs or ENAs at the 3'-end. In another preferred embodiment, the oligonucleotide comprises 1, 2, 3, or 4 LNAs or ENAs at the 5'-end or 3'-end, and a polyalkylene oxide such as TEG at the 3'- or 5'-end. The modified oligonucleotides show a significantly increased inhibition on TGF-beta expression and activity, respectively, which results in an improved prevention and/or treatment of a malignant or benign tumor, an immunologic disease, fibrosis, eye disease such as glaucoma or posterior capsular opacification (PCO), CNS disease hair loss etc. The oligonucleotides of the present invention target TGF-beta linked diseases either by hybridization with TGF-beta mRNA, preferably TGF-beta1, TGF-beta2, or TGF-beta3, alternatively, TGF-beta1, TGF-beta2, and/or TGF-beta3 mRNAs, i.e., TGF-beta1 and TGF-beta2, or TGF-beta1 and TGF-beta3, or TGF-beta2 and TGF-beta3, or TGF-beta1, TGF-beta2 and TGF-beta3 mRNAs, or any other direct or indirect effect on the TGF-beta system. An oligonucleotide inhibiting the expression of TGF-beta1, TGF-beta2, and TGF-beta3 is defined as pan-specific oligonucleotide.

In a preferred embodiment, the oligonucleotides of the present invention are for use in a method for preventing and/or treating an ophthalmic disease such as dry eye, glaucoma or posterior capsule opacification.

Preferably two or more oligonucleotides are combined, wherein at least one oligonucleotide specifically inhibits TGF-beta1 and at least one oligonucleotide specifically inhibits TGF-beta2, or wherein at least one oligonucleotide specifically inhibits TGF-beta1 and at least one oligonucleotide specifically inhibits TGF-beta3, or wherein at least one oligonucleotide specifically inhibits TGF-beta2 and at least one oligonucleotide specifically inhibits TGF-beta3, or wherein at least one oligonucleotide specifically inhibits TGF-beta1, at least one oligonucleotide specifically inhibits TGF-beta2, and at least one oligonucleotide specifically inhibits TGF-beta3.

In another embodiment, one oligonucleotide inhibits two TGF-beta isoforms such as TGF-beta1 and TGF-beta2, TGF-beta2 and TGF-beta3, or TGF-beta1 and TGF-beta3. An oligonucleotide inhibiting the expression of all three isoforms—TGF-beta1, TGF-beta2, and TGF-beta3—is defined as pan-specific oligonucleotide.

In a further embodiment three or more oligonucleotides are combined, wherein at least one oligonucleotide specifically inhibits TGF-beta1, another oligonucleotide specifically inhibits TGF-beta2, and a further oligonucleotide specifically inhibits TGF-beta3, and optionally one or more additional oligonucleotides inhibiting TGF-beta1, TGF-beta2 or TGF-beta3, and/or optionally any other factor.

The oligonucleotides of the present invention have for example an $IC_{50}$ in the range of 0.1 to 20 μM, preferably in the range of 0.2 to 15 μM, more preferably in the range of 0.4 to 10 μM, and even more preferred in the range of 0.5 to 5 μM.

The present invention further refers to a pharmaceutical composition comprising an oligonucleotide according to the invention as active ingredient. The pharmaceutical composition comprises at least one oligonucleotide of the present invention and optionally further an antisense compound, an antibody, a chemotherapeutic compound, an anti-inflammatory compound, an antiviral compound and/or an immunomodulating compound. Pharmaceutically acceptable binding agents and adjuvants optionally comprise part of the pharmaceutical composition.

In one embodiment, the oligonucleotide and the pharmaceutical composition, respectively, is formulated as dosage unit in form of capsules, tablets and pills etc., respectively, which contain for example the following compounds: microcrystalline cellulose, gum or gelatin as binders; starch or lactose as excipients; stearates as lubricants, various sweetening or flavouring agents. For capsules the dosage unit may contain a liquid carrier like fatty oils. Likewise coatings of sugar or enteric agents may be part of the dosage unit.

In a preferred embodiment the oligonucleotide or the pharmaceutical composition comprising such oligonucleotide of the present invention is formulated as eye drops or eye ointment, which optionally comprise a dye such as BBG, BBR, or trypanblue, polyvinylpyrrolidone, polyethyleneglycol (PEG), preferably PEG200, PEG400, or PEG1000, hydrogenphosphate of calium or sodium.

The oligonucleotide and/or the pharmaceutical composition is administrable via different routes. These routes of administration include, but are not limited to, electroporation, epidermal, impression into skin, intra-arterial, intra-articular, intracranial, intradermal, intra-lesional, intra-muscular, intranasal, intra-ocular, intracameral, intrathecal, intraperitoneal, intraprostatic, intrapulmonary, intraspinal, intratracheal, intratumoral, intravenous, intravesical, placement within cavities of the body, nasal inhalation, oral, pulmonary inhalation (e.g., by inhalation or insufflation of powders or aerosols, including by nebulizer), subcutaneous, subdermal, topical (including ophthalmic and to mucous membranes including vaginal and rectal delivery), or transdermal.

For parenteral, subcutaneous, intradermal or topical administration the oligonucleotide and/or the pharmaceutical composition include for example a sterile diluent, buffers, regulators of toxicity and antibacterials. In a preferred embodiment, the oligonucleotide or pharmaceutical composition is prepared with carriers that protect against degradation or immediate elimination from the body, including implants or microcapsules with controlled release properties. For intravenous administration the preferred carriers are for example physiological saline or phosphate buffered saline. An oligonucleotide and/or a pharmaceutical composition comprising such oligonucleotide for oral administration includes for example powder or granule, microparticulate, nanoparticulate, suspension or solution in water or non-aqueous media, capsule, gel capsule, sachet, tablet or minitablet. An oligonucleotide and/or a pharmaceutical composition comprising for parenteral, intrathecal, intracameral or intraventricular administration includes for example sterile aqueous solutions which optionally contain buffer, diluent and other suitable additive such as penetration enhancer, carrier compound and other pharmaceutically acceptable carrier or excipient.

A pharmaceutically acceptable carrier is for example liquid or solid, and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, a binding agent (e.g. pregelatinized maize starch, polyvinylpyrrolidone or hydroxypropyl methylcellulose, etc.); filler (e.g. lactose and other sugars, microcrystalline cellulose, pectin, gelatin, calcium sulfate, ethyl cellulose, polyacrylates or calcium hydrogen phosphate, etc.); lubricant (e.g., magnesium stearate, talcum, silica, colloidal silicon dioxide, stearic acid, metallic stearates, hydrogenated vegetable oils, corn starch, polyethylene glycols, sodium benzoate, sodium acetate, etc.); disintegrate (e.g., starch, sodium starch glycolate, etc.); or wetting agent (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404. An adjuvant is included under these phrases.

In one embodiment, the oligonucleotide or pharmaceutical composition is administered via a medical device, preferably a small pump such as a mini-pump, which is for example directly implanted into or onto the eye. Such device is for example connected to the eye motion muscle to deliver a therapeutic load, i.e., an oligonucleotide or pharmaceutical composition into the eye.

Besides being used in a method of human disease prevention and/or treatment, the oligonucleotide and/or the pharmaceutical composition according to the present invention is also used in a method for prevention and/or treatment of other subjects including veterinary animals, reptiles, birds, exotic animals and farm animals, including mammals, rodents, and the like. Mammals include for example horses, dogs, pigs, cats, or primates (for example, a monkey, a chimpanzee, or a lemur). Rodents include for example rats, rabbits, mice, squirrels, or guinea pigs.

The oligonucleotide or the pharmaceutical composition according to the invention is used in a method for the prevention and/or treatment of many different diseases, preferably benign or malignant tumors, immunologic diseases, bronchial asthma, heart disease, fibrosis (e.g., liver fibrosis, idiopathic pulmonary fibrosis, liver cirrhosis, kidney cirrhosis, scleroderma), diabetes, wound healing, disorders of the connective tissue (e.g., in heart, blood vessel, bone, joint, eye such as the Marfan or Loeys-Dietz syndrome), psoriasis, eye diseases (e.g., glaucoma, posterior capsular opacification (PCO) also known as secondary cataract, retinoblastoma, choroidcarcinoma, Marfan or Loeys-Dietz syndrome, macular degeneration, such as age-related macular degeneration, diabetic macular endma, or cataract), CNS disease (e.g., Alzheimer's disease, Parkinson's disease), coronary atherosclerosis (coronary intervention or coronary artery bypass graft (CABG) surgery or hair loss. A tumor is for example selected from the group of solid tumors, blood born tumors, leukemias, tumor metastasis, hemangiomas, acoustic neuromas, neurofibromas, trachomas, pyogenic granulomas, astrocytoma such as anaplastic astrocytoma, acoustic neuroma, blastoma, Ewing's tumor, craniopharyngioma, ependymoma, medulloblastoma, glioma, glioblastoma, hemangloblastoma, Hodgkins-lymphoma, medullablastoma, leukaemia, melanoma such as primary and/or metastatic melanoma, mesothelioma, myeloma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma (RCC, e.g., clear cell RCC, papillary RCC, chromophobe RCC), oncocytoma kidney cancer, transitional cell kidney cancer, skin cancer, small-cell bronchogenic/lung carcinoma, squamous cell carcinoma, sebaceous gland carcinoma, testicular carcinoma, and uterine cancer. The oligonucleotide or the pharmaceutical composition of the present invention is not only used in a method for the prevention and/or treatment of a tumor, but likewise on a metastasis.

The present invention is preferably directed to the prevention and/or treatment of ophthalmic diseases such as, but not limited to, glaucoma, posterior capsular opacification, dry eye, macular degeneration, e.g., age-related macular degeneration, diabetic macular endma, cataract, proliferative vitreoretinopathy, Marfan or Loeys-Dietz syndrome, and any other ocular disease linkable to TGF-beta, in particular TGF-beta1, TGF-beta2, and/or TGF-beta3, and/or being associated with fibrosis, inflammation, degeneration, aging or similar.

The antisense oligonucleotides of the present invention are characterized in that they show an unexpected low toxicity (see for example Table 7) and thus, are well tolerated by different organisms. They oligonucleotides show a reasonable distribution in the organism, wherein highest concentrations are measured in the kidney, liver, skin and spleen.

The present invention provides numerous oligonucleotides, which are highly efficient in the reduction and inhibition, respectively, of TGF-beta, in particular TGF-beta1, TGF-beta2 and/or TGF-beta3 expression due to the specific selection of the sequence of the oligonucleotide and the modification of the nucleotide. The following Table 1 shows numerous preferred modified oligonucleotides according to the present invention (modified nucleosides are indicated in bold letters). Each oligonucleotide is defined as ASPH and a number, which is defined by a specific sequence and modification of the nucleosides:

| SEQ ID NO. | Sequence (5' → 3') | Modification | ASPH |
|---|---|---|---|
| 5 | **GAC**CAGATGCA**GGA** | LNA 3 + 3 | 36 |
| 6 | **GCG**ACCGTGACCA**GAT** | LNA 3 + 3 | 80 |
| 7 | **GCG**CGACCGTGACC | LNA 3 + 3 | 98 |
| 8 | **AG**CGCGACCGTGA | LNA 2 + 3 | 111 |
| 9 | **GA**CCGTGACCAGAT | LNA 2 + 2 | 121 |
| 9 | **GAC**CGTGACCAGAT | LNA 3 + TEG | 153 |
| 10 | **CT**GCCCGCGGAT | LNA 2 + 2 | 15 |
| 11 | **TCT**GCCCGCGGAT | LNA 3 + 2 | 17 |
| 12 | **GGAT**CTGCCCGCGGA | LNA 4 + 3 | 26 |

-continued

| SEQ ID NO. | Sequence (5' → 3') | Modification | ASPH |
|---|---|---|---|
| 12 | **GGA**TCTGCCCGCGGA | LNA 3 + 4 | 27 |
| 13 | **CTTG**CTCAGGATCTGCC | LNA 4 + 4 | 37 |
| 14 | **GCTC**AGGATCTGCCCGCGG **A** | 2' O-meth 4 + 4 | 52 |
| 14 | **GCTC**AGGATCTGCCCGCGG **A** | 2' fluoro 4 + 4 | 53 |
| 15 | **GGA**TCGCCTCG**AT** | LNA 3 + 2 | 112 |
| 16 | **CC**GCGGATCG**CC** | LNA 2 + 2 | 119 |
| 17 | **ACC**TCCTTGGCGTA**GTA** | LNA 3 + 3 | 01 |
| 17 | **ACCT**CCTTGGCGT**AGTA** | LNA 4 + 4 | 02 |
| 18 | **CCT**CCTTGGCGTA**GTA** | LNA 3 + 3 | 03 |
| 18 | **CCTC**CTTGGCGT**AGTA** | LNA 4 + 4 | 04 |
| 19 | **CTC**CTTGGCGTA**GTA** | LNA 3 + 3 | 05 |
| 19 | **CTCC**TTGGCGTA**GTA** | LNA 4 + 3 | 06 |
| 19 | **CTC**CTTGGCGT**AGTA** | LNA 3 + 4 | 07 |
| 20 | **TCC**TTGGCGTA**GTA** | LNA 3 + 3 | 08 |
| 21 | **CAG**AAGTTGG**CAT** | LNA 3 + 2 | 09 |
| 21 | **CA**GAAGTTGG**CAT** | LNA 2 + 3 | 10 |
| 22 | AAGTGGGCGGGAT | – | 11 |
| 22 | **AAGT**GGGCG**GGAT** | LNA 4 + 4 | 12 |
| 22 | **AAGT**GGGCG**GGAT** | 2' O-meth 4 + 4 | 13 |
| 22 | **AAGT**GGGCG**GGAT** | 2' fluoro 4 + 4 | 14 |
| 23 | **GC**GGGATGGC**AT** | LNA 2 + 2 | 16 |
| 24 | **GA**AATCACCT**CCG** | LNA 2 + 3 | 18 |
| 25 | **AA**GTGGGCGG**GAT** | LNA 2 + 3 | 19 |
| 26 | **TG**TAGCGCTG**GGT** | LNA 2 + 3 | 20 |
| 27 | **CGA**AGGAGAGC**CA** | LNA 3 + 2 | 21 |
| 28 | **TCG**CGCTCGCA**GGC** | LNA 3 + 3 | 22 |
| 29 | **AAG**TGGGCGGG**ATG** | LNA 3 + 3 | 23 |
| 30 | **ATG**TAGCGCTG**GGT** | LNA 3 + 3 | 24 |
| 31 | **CGA**AGGAGAGC**CAT** | LNA 3 + 3 | 25 |
| 32 | **GAAA**GTGGGCGG**GAT** | LNA 4 + 3 | 28 |
| 33 | **CGAA**GGAGAGCC**ATT** | LNA 4 + 3 | 29 |
| 34 | **CGAT**CCTCTTGC**GCAT** | LNA 4 + 4 | 30 |
| 35 | **AAGT**GGGCGGGA**TGGC** | LNA 4 + 4 | 31 |
| 36 | **GATG**GAAATCACC**TCCG** | LNA 4 + 4 | 32 |
| 37 | **AAAC**CTCCTTGGC**GTAG** | LNA 4 + 4 | 33 |
| 38 | **TAGA**AAGTGGGCG**GGAT** | LNA 4 + 4 | 34 |

-continued

| SEQ ID NO. | Sequence (5' → 3') | Modification | ASPH |
|---|---|---|---|
| 39 | **GG**CGGGATGG**CAT** | LNA 2 + 3 | 35 |
| 40 | **GGGT**CTGTAGAA**AGTG** | LNA 4 + 4 | 38 |
| 41 | **GAA**GGAGAGCC**ATTC** | LNA 3 + 4 | 39 |
| 42 | **CCA**GGTTCCTG**TCTT** | LNA 3 + 4 | 40 |
| 43 | **TCT**GATCACCA**CTGG** | LNA 3 + 4 | 41 |
| 44 | **TTTC**TGATCACCA**CTGG** | LNA 4 + 4 | 42 |
| 45 | **GTCT**GTAGGAGG**GCA** | LNA 4 + 3 | 43 |
| 46 | **AGTC**TGTAGGAG**GGCA** | LNA 4 + 4 | 44 |
| 47 | **TC**TGTAGGAG**GGC** | LNA 2 + 3 | 45 |
| 48 | **CAGA**TGCCAGTTT**TAAC** | LNA 4 + 4 | 46 |
| 49 | **CAAA**GTATTTGGT**CTCC** | LNA 4 + 4 | 47 |
| 50 | **CCTT**AAGCCATCC**ATGA** | LNA 4 + 4 | 48 |
| 51 | **GTAC**TGGCCAGC**TAA** | LNA 4 + 3 | 49 |
| 52 | **GCCT**CGATCCTCTTGC**GCAT** | 2' O-meth 4 + 4 | 50 |
| 52 | **GCCT**CGATCCTCTTGC**GCAT** | 2' fluoro 4 + 4 | 51 |
| 53 | **AAAC**CTCCTTGGCGTA**GTAC** | 2' O-meth 4 + 4 | 54 |
| 53 | **AAAC**CTCCTTGGCGTA**GTAC** | 2' fluoro 4 + 4 | 55 |
| 54 | **GAAA**GTGGGCGGGATG**GCAT** | 2' O-meth 4 + 4 | 56 |
| 54 | **GAAA**GTGGGCGGGATG**GCAT** | 2' fluoro 4 + 4 | 57 |
| 55 | **GAA**TTGCTCGCTTA**GGG** | LNA 3 + 3 | 60 |
| 56 | **CGT**CGCGGTTGCGT**TCA** | LNA 3 + 3 | 61 |
| 57 | **CGT**GGCCTACACCC**TGG** | LNA 3 + 3 | 62 |
| 58 | **TTC**TAAAGCAATAG**GCC** | LNA 3 + 3 | 63 |
| 59 | **AGA**ATGGTTAGAGG**TTC** | LNA 3 + 3 | 64 |
| 60 | **TCT**GAACTAGTACC**GCC** | LNA 3 + 3 | 65 |
| 61 | **CCC**ATTAATATGAC**CTC** | LNA 3 + 3 | 66 |
| 62 | **TTT**AGTTAGAACCC**TAA** | LNA 3 + 3 | 67 |
| 63 | **CCT**CAGATATAGAT**AAC** | LNA 3 + 3 | 68 |
| 64 | **TAC**TATTATGGCAT**CCC** | LNA 3 + 3 | 69 |
| 65 | **TGC**CCACTTGCATA**CTA** | LNA 3 + 3 | 70 |
| 66 | **AGC**GTAATTGGTCA**TCA** | LNA 3 + 3 | 71 |
| 67 | **CGT**TGGCAGAACAT**AGA** | LNA 3 + 3 | 72 |
| 68 | **GGG**ATACTGTCTAG**ACC** | LNA 3 + 3 | 73 |
| 69 | **ATT**GGCAACTCGTT**TGA** | LNA 3 + 3 | 74 |
| 70 | **CGT**CAGGCTAATA**TTC** | LNA 3 + 3 | 75 |
| 71 | **GGA**TGACTCCCTA**GAC** | LNA 3 + 3 | 76 |
| 72 | **GTC**GCGGTTGCGT**TCA** | LNA 3 + 3 | 77 |

-continued

| SEQ ID NO. | Sequence (5' → 3') | Modification | ASPH |
|---|---|---|---|
| 73 | **CTC**GGTACTCGGT**CGG** | LNA 3 + 3 | 78 |
| 74 | **GGT**TCGGTCCTGC**CTT** | LNA 3 + 3 | 79 |
| 75 | **AAT**AGGCCGCATC**CAA** | LNA 3 + 3 | 81 |
| 76 | **AAC**TAGTACCGCC**TTT** | LNA 3 + 3 | 82 |
| 77 | **TCG**GTCATATAAT**AAC** | LNA 3 + 3 | 83 |
| 78 | **AGA**CCGTCAGGC**TAA** | LNA 3 + 3 | 84 |
| 79 | **GTC**GCGGTTGCG**TTC** | LNA 3 + 3 | 85 |
| 80 | **TTC**CACTGCGGC**GCT** | LNA 3 + 3 | 86 |
| 81 | **AAG**GAGCGGTTC**GGT** | LNA 3 + 3 | 87 |
| 82 | **CTC**GGGTGCGGA**GTG** | LNA 3 + 3 | 88 |
| 83 | **CTG**ACTTTGGCG**AGT** | LNA 3 + 3 | 89 |
| 84 | **GAT**AGGAACGGT**ACG** | LNA 3 + 3 | 90 |
| 85 | **CAC**TTTGGATTC**CCG** | LNA 3 + 3 | 91 |
| 86 | **GTC**GCGGTTGC**GTT** | LNA 3 + 3 | 92 |
| 87 | **TAC**ACCCTGGC**GGG** | LNA 3 + 3 | 93 |
| 88 | **CTC**GGTACTCG**GTC** | LNA 3 + 3 | 94 |
| 89 | **AGG**AGCGGTTC**GGT** | LNA 3 + 3 | 95 |
| 90 | **GTC**TCGGGTGC**GGA** | LNA 3 + 3 | 96 |
| 91 | **TAC**GGGACGGG**CAG** | LNA 3 + 3 | 97 |
| 92 | **CGT**CGCTCCTC**TCG** | LNA 3 + 3 | 99 |
| 93 | **TAG**CGCTGGGT**TGG** | LNA 3 + 3 | 100 |
| 94 | **AAG**CAATAGGC**CGC** | LNA 3 + 3 | 101 |
| 95 | **TAC**GGGCATGC**TCC** | LNA 3 + 3 | 102 |
| 96 | **AGG**CGCGGGAT**AGG** | LNA 3 + 3 | 103 |
| 97 | **TTT**GGATTCCC**GCC** | LNA 3 + 3 | 104 |
| 98 | **ACC**ACTAGAGC**ACC** | LNA 3 + 3 | 105 |
| 99 | **GCG**TTGGCAGA**ACA** | LNA 3 + 3 | 106 |
| 100 | **TT**GCTCGCTT**AGG** | LNA 2 + 3 | 107 |
| 101 | **GTC**GCGGTTG**CGT** | LNA 3 + 2 | 108 |
| 102 | **GG**CGCTCGGT**ACT** | LNA 2 + 3 | 109 |
| 103 | **ATC**TGAACTC**GGC** | LNA 3 + 2 | 110 |
| 104 | **CG**GTTGGTCT**GTT** | LNA 2 + 3 | 113 |
| 105 | **TC**CACCCTAG**ATC** | LNA 2 + 3 | 114 |
| 106 | **CT**AGTACCGC**CTT** | LNA 2 + 3 | 115 |
| 107 | **GGT**CGGCAGTC**AA** | LNA 3 + 2 | 116 |
| 108 | **CT**TGCGACAC**CC** | LNA 2 + 2 | 117 |
| 109 | **GA**GCGGTTCG**GT** | LNA 2 + 2 | 118 |

-continued

| SEQ ID NO. | Sequence (5' → 3') | Modification | ASPH |
|---|---|---|---|
| 110 | **AC**ACAGTAGTGC**AT** | LNA 2 + 2 | 120 |
| 111 | **GG**GTCTGTAGAA**AG** | LNA 2 + 2 | 122 |
| 111 | **GGG**TCTGTAGAAAG | LNA 3 + TEG | 154 |
| 112 | **GG**TTGGAGATGT**TA** | LNA 2 + 2 | 123 |
| 112 | **GGT**TGGAGATGTTA | LNA 3 + TEG | 155 |
| 113 | **TG**GGTTGGAGAT**GT** | LNA 2 + 2 | 124 |
| 113 | **TGG**GTTGGAGATGT | LNA 3 + TEG | 156 |
| 114 | **GC**TGGGTTGGAG**AT** | LNA 2 + 2 | 125 |
| 114 | **GCT**GGGTTGGAGAT | LNA 3 + TEG | 157 |
| 115 | **GC**GCTGGGTTGG**AG** | LNA 2 + 2 | 126 |
| 115 | **GCG**CTGGGTTGGAG | LNA 3 + TEG | 158 |
| 116 | **AG**CGCTGGGTTG**GA** | LNA 2 + 2 | 127 |
| 116 | **AGC**GCTGGGTTGGA | LNA 3 + TEG | 159 |
| 117 | **TA**GCGCTGGGTT**GG** | LNA 2 + 2 | 128 |
| 117 | **TAG**CGCTGGGTTGG | LNA 3 + TEG | 160 |
| 118 | **GT**AGCGCTGGGT**TG** | LNA 2 + 2 | 129 |
| 118 | **GTA**GCGCTGGGTTG | LNA 3 + TEG | 161 |
| 119 | **GA**TGTAGCGCTG**GG** | LNA 2 + 2 | 130 |
| 119 | **GAT**GTAGCGCTGGG | LNA 3 + TEG | 162 |
| 120 | **CC**ATTCGCCTTC**TG** | LNA 2 + 2 | 131 |
| 120 | **CCA**TTCGCCTTCTG | LNA 3 + TEG | 163 |
| 121 | **GA**GAGCCATTCG**CC** | LNA 2 + 2 | 132 |
| 121 | **GAG**AGCCATTCGCC | LNA 3 + TEG | 164 |
| 122 | **AG**CAGGGACAGT**GT** | LNA 2 + 2 | 133 |
| 122 | **AGC**AGGGACAGTGT | LNA 3 + TEG | 165 |
| 123 | **GC**AGGAGATGTG**GG** | LNA 2 + 2 | 134 |
| 123 | **GCA**GGAGATGTGGG | LNA 3 + TEG | 166 |
| 124 | **CG**GTTGGTCTGT**TG** | LNA 2 + 2 | 135 |
| 124 | **CGG**TTGGTCTGTTG | LNA 3 + TEG | 167 |
| 125 | **CC**GGTTGGTCTG**TT** | LNA 2 + 2 | 136 |
| 125 | **CCG**GTTGGTCTGTT | LNA 3 + TEG | 168 |
| 126 | **GC**CGGTTGGTCT**GT** | LNA 2 + 2 | 137 |
| 126 | **GCC**GGTTGGTCTGT | LNA 3 + TEG | 169 |
| 127 | **AG**TTGGCATTGT**AC** | LNA 2 + 2 | 138 |
| 127 | **AGT**TGGCATTGTAC | LNA 3 + TEG | 170 |
| 128 | **GG**TTAGAGGTTC**TA** | LNA 2 + 2 | 139 |
| 128 | **GGT**TAGAGGTTCTA | LNA 3 + TEG | 171 |
| 129 | **AT**GGTTAGAGGT**TC** | LNA 2 + 2 | 140 |

-continued

| SEQ ID NO. | Sequence (5' → 3') | Modification | ASPH |
|---|---|---|---|
| 129 | **ATG**GTTAGAGGTTC | LNA 3 + TEG | 172 |
| 130 | **AG**AATGGTTAGA**GG** | LNA 2 + 2 | 141 |
| 130 | **AGA**ATGGTTAGAGG | LNA 3 + TEG | 173 |
| 131 | **AG**AGAATGGTTA**GA** | LNA 2 + 2 | 142 |
| 131 | **AGA**GAATGGTTAGA | LNA 3 + TEG | 174 |
| 132 | **CG**TTGTCGTCGT**CA** | LNA 2 + 2 | 143 |
| 132 | **CGT**TGTCGTCGTCA | LNA 3 + TEG | 175 |
| 133 | **AC**CAAGGCTCTC**TT** | LNA 2 + 2 | 144 |
| 133 | **ACC**AAGGCTCTCTT | LNA 3 + TEG | 176 |
| 134 | **GC**TTCTTGTCTC**TC** | LNA 2 + 2 | 145 |
| 134 | **GCT**TCTTGTCTCTC | LNA 3 + TEG | 177 |
| 135 | **GG**AACGGTACGT**AC** | LNA 2 + 2 | 146 |
| 135 | **GGA**ACGGTACGTAC | LNA 3 + TEG | 178 |
| 136 | **TA**GGAACGGTAC**GT** | LNA 2 + 2 | 147 |
| 136 | **TAG**GAACGGTACGT | LNA 3 + TEG | 179 |
| 137 | **GG**GATAGGAACG**GT** | LNA 2 + 2 | 148 |
| 137 | **GGG**ATAGGAACGGT | LNA 3 + TEG | 180 |
| 138 | **CG**CGGGATAGGA**AC** | LNA 2 + 2 | 149 |
| 138 | **CGC**GGGATAGGAAC | LNA 3 + TEG | 181 |
| 139 | **AG**GCGCGGGATA**GG** | LNA 2 + 2 | 150 |
| 139 | **AGG**CGCGGGATAGG | LNA 3 + TEG | 182 |
| 140 | **GT**CAAGCTGGAT**GG** | LNA 2 + 2 | 151 |
| 140 | **GTC**AAGCTGGATGG | LNA 3 + TEG | 183 |
| 141 | **TC**TGTAGGAG**GGC** | ENA 2 + 3 | 184 |
| 142 | **GAC**CAGATGCA**GGA** | ENA 3 + 3 | 185 |
| 143 | **CTC**CTTGGCGTA**GTA** | ENA 3 + 3 | 186 |
| 144 | **CCT**CCTTGGCGTA**GTA** | ENA 3 + 3 | 187 |
| 145 | **CAGA**TGCCAGTTT**TAAC** | ENA 4 + 4 | 188 |
| 146 | **AGC**GTAATTGGTCA**TCA** | ENA 3 + 3 | 189 |
| 147 | **AGT**ATTTGGTCTCC | LNA 3 + 3 | 190 or M12-ASPH47 |
| 148 | **AAG**TATTTGGTCTC | LNA 3 + 3 | 191 or M9-ASPH47 |
| 149 | **AAG**TATTTGGTCTCC | LNA 3 + 3 | 192 or M8-ASPH47 |
| 150 | **CAA**AGTATTTGGTC**TCC** | LNA 3 + 3 | 193 |
| 151 | **AGC**TCGTCCCTCCT**CCC** | LNA 3 + 3 | 1000 |

-continued

| SEQ ID NO. | Sequence (5' → 3') | Modification | ASPH |
|---|---|---|---|
| 152 | **GAG**GGCTGGTCCGG**AAT** | LNA 3 + 3 | 1001 |
| 153 | **CGA**GGGCTGGTCCG**GAA** | LNA 3 + 3 | 1002 |
| 154 | **GAG**GGCGGCATGGG**GGA** | LNA 3 + 3 | 1003 |
| 155 | **GCG**GGTGCTGTTGT**ACA** | LNA 3 + 3 | 1004 |
| 156 | **CGC**GGGTGCTGTTG**TAC** | LNA 3 + 3 | 1005 |
| 157 | **GTC**GCGGGTGCTGT**TGT** | LNA 3 + 3 | 1006 |
| 158 | **GGT**CGCGGGTGCTG**TTG** | LNA 3 + 3 | 1007 |
| 159 | **CCG**GTCGCGGGTGC**TGT** | LNA 3 + 3 | 1008 |
| 160 | **CCC**GGTCGCGGGTG**CTG** | LNA 3 + 3 | 1009 |
| 161 | **AGC**ACGCGGGTGAC**CTC** | LNA 3 + 3 | 1010 |
| 162 | **TTA**GCACGCGGGTG**ACC** | LNA 3 + 3 | 1011 |
| 163 | **GGG**CTCGTGGATCC**ACT** | LNA 3 + 3 | 1012 |
| 164 | **CCT**TGGGCTCGTGG**ATC** | LNA 3 + 3 | 1013 |
| 165 | **TGG**CATGGTAGCCC**TTG** | LNA 3 + 3 | 1014 |
| 166 | **CGA**GGGCTGGTCC**GGA** | LNA 3 + 3 | 1015 |
| 167 | **GCG**GGTGCTGTTG**TAC** | LNA 3 + 3 | 1016 |
| 168 | **GCA**CGCGGGTGAC**CTC** | LNA 3 + 3 | 1017 |
| 169 | **CCT**TGGGCTCGTG**GAT** | LNA 3 + 3 | 1018 |
| 170 | **GGC**ATGGTAGCCC**TTG** | LNA 3 + 3 | 1019 |
| 171 | **GGG**TGCTGTTG**TAC** | LNA 3 + 3 | 1020 |
| 172 | **TCG**CGGGTGCT**GTT** | LNA 3 + 3 | 1021 |
| 173 | **GTC**GCGGGTGC**TGT** | LNA 3 + 3 | 1022 |
| 174 | **CTC**GTGGATCC**ACT** | LNA 3 + 3 | 1023 |
| 175 | **ATG**GTAGCCCT**TGG** | LNA 3 + 3 | 1024 |
| 176 | **TGG**CATGGTAG**CCC** | LNA 3 + 3 | 1025 |
| 177 | **GAA**GTTGGCAT**GGT** | LNA 3 + 3 | 1026 |
| 178 | **TC**GCGGGTGC**TGT** | LNA 2 + 3 | 1027 |
| 179 | **CA**CCCGGTCG**CGG** | LNA 2 + 3 | 1028 |
| 180 | **CC**ACCCGGTC**GCG** | LNA 2 + 3 | 1029 |
| 181 | **CGC**CAGGAATT**GT** | LNA 3 + 2 | 1030 |
| 182 | **GG**CTCGTGGA**TCC** | LNA 2 + 3 | 1031 |
| 183 | **TG**GGCTCGTG**GAT** | LNA 2 + 3 | 1032 |
| 184 | **GC**ATGGTAGC**CCT** | LNA 2 + 3 | 1033 |
| 185 | **AG**TTGGCATG**GTA** | LNA 2 + 3 | 1034 |
| 186 | **TT**GCAGGAGC**GCA** | LNA 2 + 3 | 1035 |
| 187 | **ATT**AGCACGCGGGT**GAC** | LNA 3 + 3 | 1036 |
| 188 | **ACC**ATTAGCACGCG**GGT** | LNA 3 + 3 | 1037 |
| 189 | **CAC**CATTAGCACGC**GGG** | LNA 3 + 3 | 1038 |

-continued

| SEQ ID NO. | Sequence (5' → 3') | Modification | ASPH |
|---|---|---|---|
| 190 | **CCA**CCATTAGCACG**CGG** | LNA 3 + 3 | 1039 |
| 191 | **TCC**ACCATTAGCAC**GCG** | LNA 3 + 3 | 1040 |
| 192 | **TCC**ACCTTGGGCTT**GCG** | LNA 3 + 3 | 1041 |
| 193 | **TTA**GCACGCGGGT**GAC** | LNA 3 + 3 | 1042 |
| 194 | **ACC**ATTAGCACGC**GGG** | LNA 3 + 3 | 1043 |
| 195 | **CAC**CATTAGCACG**CGG** | LNA 3 + 3 | 1044 |
| 196 | **CAC**CATTAGCAC**GCG** | LNA 3 + 3 | 1045 |
| 197 | **GCG**GCACGCAGC**ACG** | LNA 3 + 3 | 1046 |
| 198 | **TCG**ATGCGCTT**CCG** | LNA 3 + 3 | 1047 |
| 199 | **TAG**CACGCGGG**TGA** | LNA 3 + 3 | 1048 |
| 200 | **ATT**AGCACGCG**GGT** | LNA 3 + 3 | 1049 |
| 201 | **CAT**TAGCACGC**GGG** | LNA 3 + 3 | 1050 |
| 202 | **ACC**ATTAGCAC**GCG** | LNA 3 + 3 | 1051 |
| 203 | **CAC**CATTAGCA**CGC** | LNA 3 + 3 | 1052 |
| 204 | **CCA**CCATTAGC**ACG** | LNA 3 + 3 | 1053 |
| 205 | **TCC**ACCATTAG**CAC** | LNA 3 + 3 | 1054 |
| 206 | **GAC**CTTGCTGT**ACT** | LNA 3 + 3 | 1055 |
| 207 | **GGA**CCTTGCTG**TAC** | LNA 3 + 3 | 1056 |
| 208 | **AGG**ACCTTGCT**GTA** | LNA 3 + 3 | 1057 |
| 209 | **CGG**CACGCAGC**ACG** | LNA 3 + 3 | 1058 |
| 210 | **ACC**TTGGGCTT**GCG** | LNA 3 + 3 | 1059 |
| 211 | **TTA**GCACGCGG**GT** | LNA 3 + 2 | 1060 |
| 212 | **ACC**ATTAGCAC**GC** | LNA 3 + 2 | 1061 |
| 213 | **CGG**CACGCAGC**AC** | LNA 3 + 2 | 1062 |
| 214 | **CAC**CAGCTCCATGT**CGA** | LNA 3 + 3 | 1063 |
| 215 | **TCG**CGGGTGCTGTT**GTA** | LNA 3 + 3 | 1064 |
| 216 | **GTG**TCCAGGCTCCA**AAT** | LNA 3 + 3 | 1065 |
| 216 | **GTGT**CCAGGCTCCAA**AT** | LNA 4 + 2 | 1066 |
| 217 | **GCT**CGTCCCTCCT**CCC** | LNA 3 + 3 | 1067 |
| 218 | **ACC**AGCTCGTCCC**TCC** | LNA 3 + 3 | 1068 |
| 219 | **GGA**GGCCCCGCCC**CTG** | LNA 3 + 3 | 1069 |
| 220 | **CAT**GGGGGAGGCG**GCG** | LNA 3 + 3 | 1070 |
| 220 | **CAT**GGGGGAGGC**G**G**CG** | 3LNA + 9N + 1LNA + 1N + 2LNA | 1071 |
| 221 | **ACC**AGCTCCATGT**CGA** | LNA 3 + 3 | 1072 |
| 222 | **GGT**CGCGGGTGCT**GTT** | LNA 3 + 3 | 1073 |
| 223 | **GGA**CCTTGCTGTA**CTG** | LNA 3 + 3 | 1074 |
| 223 | **GGAC**CTTGCTGTAC**TG** | LNA 4 + 2 | 1075 |

-continued

| SEQ ID NO. | Sequence (5' → 3') | Modification | ASPH |
|---|---|---|---|
| 224 | **TCC**ACCTTGGGCT**TGC** | LNA 3 + 3 | 1076 |
| 225 | **AGC**TCGTCCCTC**CTC** | LNA 3 + 3 | 1077 |
| 226 | **CCA**GCTCGTCCC**TCC** | LNA 3 + 3 | 1078 |
| 227 | **GAG**GGCTGGTCC**GGA** | LNA 3 + 3 | 1079 |
| 228 | **TCC**CGAGGGCTG**GTC** | LNA 3 + 3 | 1080 |
| 229 | **CG**GCATGGGGG**AGGC** | LNA 2 + 4 | 1081 |
| 230 | **CAG**CTCCATGTC**GAT** | LNA 3 + 3 | 1082 |
| 231 | **ACC**AGCTCCATG**TCG** | LNA 3 + 3 | 1083 |
| 232 | **TCG**CGGGTGCTG**TTG** | LNA 3 + 3 | 1084 |
| 233 | **GTC**GCGGGTGCT**GTT** | LNA 3 + 3 | 1085 |
| 234 | **GGT**CGCGGGTGC**TGT** | LNA 3 + 3 | 1086 |
| 235 | **AGC**ACGCGGGTG**ACC** | LNA 3 + 3 | 1087 |
| 236 | **TAG**CACGCGGGT**GAC** | LNA 3 + 3 | 1088 |
| 237 | **CAT**TAGCACGCG**GGT** | LNA 3 + 3 | 1089 |
| 238 | **TCC**ACCATTAGC**ACG** | LNA 3 + 3 | 1090 |
| 239 | **CCAG**GAATTGTTG**CT** | LNA 4 + 2 | 1091 |
| 240 | **TTG**GGCTCGTGG**ATC** | LNA 3 + 3 | 1092 |
| 241 | **CTT**GGGCTCGTG**GAT** | LNA 3 + 3 | 1093 |
| 242 | **TTG**GCATGGTAG**CCC** | LNA 3 + 3 | 1094 |
| 243 | **GAA**GTTGGCATG**GTA** | LNA 3 + 3 | 1095 |
| 244 | **AGA**AGTTGGCAT**GGT** | LNA 3 + 3 | 1096 |
| 245 | **TGTC**CAGGCTCCA**AA** | LNA 4 + 2 | 1097 |
| 246 | **AGG**ACCTTGCTG**TAC** | LNA 3 + 3 | 1098 |
| 247 | **CACC**TTGGGCTTG**CG** | LNA 4 + 2 | 1099 |
| 247 | **C**A**CC**TTGGGCTT**G**C**G** | 1LNA + 1N + 2LNA + 8N + 1LNA + 1N + 1LNA | 1100 |
| 248 | **AGC**TCGTCCCT**CCT** | LNA 3 + 3 | 1101 |
| 249 | **CAG**CTCGTCCC**TCC** | LNA 3 + 3 | 1102 |
| 250 | **ACC**AGCTCGTC**CCT** | LNA 3 + 3 | 1103 |
| 251 | **CCC**GAGGGCTG**GTC** | LNA 3 + 3 | 1104 |
| 252 | **GC**GGCATGGG**GGAG** | LNA 2 + 4 | 1105 |
| 253 | **GTC**TTGCAGGT**GGA** | LNA 3 + 3 | 1106 |
| 254 | **TC**GATGCGCT**TCCG** | LNA 2 + 4 | 1107 |
| 254 | **TC**GATGCGCTT**CCG** | LNA 2 + 3 | 1108 |
| 254 | **TC**GATGCGCT**TC**C**G** | 2LNA + 8N + 2LNA + 1N + 1LNA | 1109 |
| 254 | **TC**GATGCGCTT**C**C**G** | 2LNA + 9N + 1LNA + 1N + 1LNA | 1110 |

-continued

| SEQ ID NO. | Sequence (5' → 3') | Modification | ASPH |
|---|---|---|---|
| 254 | **TC**GATGCGCT**T**CC**G** | 2LNA + 8N + 1LNA + 2N + 1LNA | 1111 |
| 255 | **GGAC**AGGATCTG**GC** | LNA 4 + 2 | 1112 |
| 256 | **ACC**TCCCCCTG**GCT** | LNA 3 + 3 | 1113 |
| 257 | **ACCA**TTAGCACG**CG** | LNA 4 + 2 | 1114 |
| 257 | **ACC**ATTAGCAC**G**C**G** | 3LNA + 8N + 1LNA + 1N + 1LNA | 1115 |
| 258 | **CA**GCAGTTCT**TCTC** | LNA 2 + 4 | 1116 |
| 259 | **TAC**AGCTGCCG**CAC** | LNA 3 + 3 | 1117 |
| 260 | **AGT**TGGCATGG**TAG** | LNA 3 + 3 | 1118 |
| 260 | **AGTT**GGCATGGT**AG** | LNA 4 + 2 | 1119 |
| 261 | **AAG**TTGGCATG**GTA** | LNA 3 + 3 | 1120 |
| 262 | **GAAG**TTGGCATG**GT** | LNA 4 + 2 | 1121 |
| 263 | **TCC**AGGCTCCA**AAT** | LNA 3 + 3 | 1122 |
| 264 | **ACC**TTGCTGTA**CTG** | LNA 3 + 3 | 1123 |
| 264 | **ACCT**TGGGCTTG**CG** | LNA 4 + 2 | 1124 |
| 264 | **ACC**TTGGGCTTG**CG** | LNA 3 + 2 | 1125 |
| 264 | **ACC**TTGGGCTT**G**C**G** | 3LNA + 8N + 1LNA + 1N + 1LNA | 1126 |
| 264 | **AC**CTTGGGCTT**G**C**G** | 2LNA + 9N + 1LNA + 1N + 1LNA | 1127 |
| 264 | **AC**CTTGGGCT**TG**C**G** | 2LNA + 8N + 2LNA + 1N + 1LNA | 1128 |
| 265 | **TTG**CAGGAGCG**CAC** | LNA 3 + 3 | 1129 |
| 266 | **GCAG**AAGTTGGC**AT** | LNA 4 + 2 | 1130 |
| 267 | **CGG**GTGCTGTT**GTA** | LNA 3 + 3 | 1131 |
| 267 | **CG**GGTGCTGT**TGTA** | LNA 2 + 4 | 1132 |
| 268 | **CCC**AGCGGCAACGG**AAA** | LNA 3 + 3 | 1133 |
| 269 | **CAA**GAGGTCCCCGC**GCC** | LNA 3 + 3 | 1134 |
| 270 | **GCG**TCCCCGGCGGC**AAA** | LNA 3 + 3 | 1135 |
| 271 | **GGT**CGGCGACTCCC**GAG** | LNA 3 + 3 | 1136 |
| 272 | **TCG**GAGAGAGATCC**GTC** | LNA 3 + 3 | 1137 |
| 273 | **ATC**CCACGGAAATA**ACC** | LNA 3 + 3 | 1138 |
| 274 | **CTC**AGTATCCCACG**GAA** | LNA 3 + 3 | 1139 |
| 275 | **ACT**GCCGAGAGCGC**GAA** | LNA 3 + 3 | 1140 |
| 276 | **CTG**ATGTGTTGAAG**AAC** | LNA 3 + 3 | 1141 |
| 277 | **TGA**GGTATCGCCAG**GAA** | LNA 3 + 3 | 1142 |
| 278 | **ACT**GCCGCACAACT**CCG** | LNA 3 + 3 | 1143 |
| 279 | **CGG**CCCACGTAGTA**CAC** | LNA 3 + 3 | 1144 |
| 280 | **CCC**AGCGGCAACG**GAA** | LNA 3 + 3 | 1145 |

-continued

| SEQ ID NO. | Sequence (5' → 3') | Modification | ASPH |
|---|---|---|---|
| 281 | **TCG**CGCCAAGAGG**TCC** | LNA 3 + 3 | 1146 |
| 282 | **GGT**CGGCGACTCC**CGA** | LNA 3 + 3 | 1147 |
| 283 | **GTC**GGAGAGAGAT**CCG** | LNA 3 + 3 | 1148 |
| 284 | **TCA**GTATCCCACG**GAA** | LNA 3 + 3 | 1149 |
| 285 | **CGA**GAGCGCGAAC**AGG** | LNA 3 + 3 | 1150 |
| 286 | **ACT**GCCGAGAGCG**CGA** | LNA 3 + 3 | 1151 |
| 287 | **GGC**GTCAGCACCA**GTA** | LNA 3 + 3 | 1152 |
| 288 | **GGT**TTCCACCATT**AGC** | LNA 3 + 3 | 1153 |
| 289 | **GAG**GTATCGCCAG**GAA** | LNA 3 + 3 | 1154 |
| 290 | **AAC**CACTGCCGCA**CAA** | LNA 3 + 3 | 1155 |
| 291 | **CGG**CCCACGTAGT**ACA** | LNA 3 + 3 | 1156 |
| 292 | **CGG**CGGCTCGTC**TCA** | LNA 3 + 3 | 1157 |
| 293 | **CCC**AGCGGCAAC**GGA** | LNA 3 + 3 | 1158 |
| 294 | **TCG**CGCCAAGAG**GTC** | LNA 3 + 3 | 1159 |
| 295 | **CGT**CGCGCCAAG**AGG** | LNA 3 + 3 | 1160 |
| 296 | **GGA**GCAAGCGTC**CCC** | LNA 3 + 3 | 1161 |
| 297 | **GTG**CGCCCGAGG**TCT** | LNA 3 + 3 | 1162 |
| 298 | **GTC**TAGGATGCG**CGG** | LNA 3 + 3 | 1163 |
| 299 | **CAG**TATCCCACG**GAA** | LNA 3 + 3 | 1164 |
| 300 | **CCG**AGAGCGCGA**ACA** | LNA 3 + 3 | 1165 |
| 301 | **GGC**GTCAGCACC**AGT** | LNA 3 + 3 | 1166 |
| 302 | **GTT**GCTGAGGTA**TCG** | LNA 3 + 3 | 1167 |
| 303 | **ACC**ACTGCCGCA**CAA** | LNA 3 + 3 | 1168 |
| 304 | **CGG**CCCACGTAG**TAC** | LNA 3 + 3 | 1169 |
| 305 | **CTC**GGCGACTC**CTT** | LNA 3 + 3 | 1170 |
| 306 | **AGC**GGCAACGG**AAA** | LNA 3 + 3 | 1171 |
| 307 | **TCG**CGCCAAGA**GGT** | LNA 3 + 3 | 1172 |
| 308 | **TCC**CCGGCGGC**AAA** | LNA 3 + 3 | 1173 |
| 309 | **TGC**GCCCGAGG**TCT** | LNA 3 + 3 | 1174 |
| 310 | **GTC**TAGGATGC**GCG** | LNA 3 + 3 | 1175 |
| 311 | **GGT**CGGAGAGA**GAT** | LNA 3 + 3 | 1176 |
| 312 | **CAC**GGAAATAA**CCT** | LNA 3 + 3 | 1177 |
| 313 | **AGA**GCGCGAAC**AGG** | LNA 3 + 3 | 1178 |
| 314 | **ATA**GTCCCGCG**GCC** | LNA 3 + 3 | 1179 |
| 315 | **TAG**TAGTCGGC**CTC** | LNA 3 + 3 | 1180 |
| 316 | **ATA**GATTTCGT**TGT** | LNA 3 + 3 | 1181 |
| 317 | **GAG**GTATCGCC**AGG** | LNA 3 + 3 | 1182 |
| 318 | **GCC**GCACAACT**CCG** | LNA 3 + 3 | 1183 |
| 319 | **TC**GCGCCAAG**AGG** | LNA 2 + 3 | 1184 |
| 320 | **AAG**CGTCCCCG**GC** | LNA 3 + 2 | 1185 |
| 321 | **GAC**GCCGTGTA**GG** | LNA 3 + 2 | 1186 |
| 322 | **GT**CGGCGACT**CCC** | LNA 2 + 3 | 1187 |
| 323 | **TGC**GCCCGAGG**TC** | LNA 3 + 2 | 1188 |
| 324 | **GTC**GGAGAGAG**AT** | LNA 3 + 2 | 1189 |
| 325 | **TCC**CACGGAAA**TA** | LNA 3 + 2 | 1190 |
| 326 | **TG**CCGAGAGC**GCG** | LNA 2 + 3 | 1191 |
| 327 | **TAG**TCCCGCGG**CC** | LNA 3 + 2 | 1192 |
| 328 | **TAG**TAGTCGGC**CT** | LNA 3 + 2 | 1193 |
| 329 | **CA**TAGATTTC**GTT** | LNA 2 + 3 | 1194 |
| 330 | **TTT**AACTTGAG**CC** | LNA 3 + 2 | 1195 |
| 331 | **GAG**GTATCGCC**AG** | LNA 3 + 2 | 1196 |
| 332 | **AC**TCCGGTGA**CAT** | LNA 2 + 3 | 1197 |
| 333 | **GC**CCACGTAG**TAC** | LNA 2 + 3 | 1198 |
| 334 | **TC**GGCGACTC**CC** | LNA 2 + 2 | 1199 |
| 335 | **GT**CGGCGACT**CC** | LNA 2 + 2 | 1200 |
| 336 | **CAG**GAAGCGCTGGC**AAC** | LNA 3 + 3 | 2000 |
| 337 | **GGT**GCATGAACTCA**CTG** | LNA 3 + 3 | 2001 |
| 338 | **GTC**CCCTAATGGCT**TCC** | LNA 3 + 3 | 2002 |
| 339 | **ATC**TGTCCCCTAAT**GGC** | LNA 3 + 3 | 2003 |
| 340 | **CCG**GGTGCTGTTGT**AAA** | LNA 3 + 3 | 2004 |
| 341 | **CCT**GGATCATGTCG**AAT** | LNA 3 + 3 | 2005 |
| 342 | **CCC**TGGATCATGTC**GAA** | LNA 3 + 3 | 2006 |
| 343 | **GTA**GCACCTGCTTC**CAG** | LNA 3 + 3 | 2007 |
| 344 | **GGG**CTTTCTAAAT**GAC** | LNA 3 + 3 | 2008 |
| 345 | **TGA**CTCCCAGCAG**GCC** | LNA 3 + 3 | 2009 |
| 346 | **GTG**CATGAACTCA**CTG** | LNA 3 + 3 | 2010 |
| 347 | **GGT**GCATGAACTC**ACT** | LNA 3 + 3 | 2011 |
| 348 | **ATC**TGTCCCCTAA**TGG** | LNA 3 + 3 | 2012 |
| 349 | **CGG**GTGCTGTTGT**AAA** | LNA 3 + 3 | 2013 |
| 350 | **CCG**GGTGCTGTTG**TAA** | LNA 3 + 3 | 2014 |
| 351 | **CCT**GGATCATGTC**GAA** | LNA 3 + 3 | 2015 |
| 352 | **CCC**TGGATCATGT**CGA** | LNA 3 + 3 | 2016 |
| 353 | **TTT**GAATTTGATT**TCC** | LNA 3 + 3 | 2017 |
| 354 | **GGG**CCTGAGCAGA**AGT** | LNA 3 + 3 | 2018 |
| 355 | **GGG**GGCTTTCTA**AAT** | LNA 3 + 3 | 2019 |

-continued

| SEQ ID NO. | Sequence (5' → 3') | Modification | ASPH |
|---|---|---|---|
| 356 | **TTT**GTTTACACT**TCC** | LNA 3 + 3 | 2020 |
| 357 | **CCA**GCTAAAGGT**GGG** | LNA 3 + 3 | 2021 |
| 358 | **ATG**GCTGGGTCC**CAA** | LNA 3 + 3 | 2022 |
| 359 | **GAG**TTTTTCCTT**AGG** | LNA 3 + 3 | 2023 |
| 360 | **AGG**GGTGGCAAG**GCA** | LNA 3 + 3 | 2024 |
| 361 | **TGA**CTCCCAGCA**GGC** | LNA 3 + 3 | 2025 |
| 362 | **GAA**GCGCTGGCA**ACC** | LNA 3 + 3 | 2026 |
| 363 | **GTG**CATGAACTC**ACT** | LNA 3 + 3 | 2027 |
| 364 | **GTG**GTGCAAGTG**GAC** | LNA 3 + 3 | 2028 |
| 365 | **CTA**ATGGCTTCC**ACC** | LNA 3 + 3 | 2029 |
| 366 | **CCC**CTAATGGCT**TCC** | LNA 3 + 3 | 2030 |
| 367 | **ATC**TGTCCCCTA**ATG** | LNA 3 + 3 | 2031 |
| 368 | **GAT**CTGTCCCCT**AAT** | LNA 3 + 3 | 2032 |
| 369 | **AGA**TCTGTCCCC**TAA** | LNA 3 + 3 | 2033 |
| 370 | **GGT**GCTGTTGTA**AAG** | LNA 3 + 3 | 2034 |
| 371 | **CCG**GGTGCTGTT**GTA** | LNA 3 + 3 | 2035 |
| 372 | **GAT**CATGTCGAA**TTT** | LNA 3 + 3 | 2036 |
| 373 | **CCT**GGATCATGT**CGA** | LNA 3 + 3 | 2037 |
| 374 | **CCC**TGGATCATG**TCG** | LNA 3 + 3 | 2038 |
| 375 | **GAT**TTCCATCAC**CTC** | LNA 3 + 3 | 2039 |
| 376 | **TTG**AATTTGATT**TCC** | LNA 3 + 3 | 2040 |
| 377 | **AGC**AGTTCTCCT**CCA** | LNA 3 + 3 | 2041 |
| 378 | **GCC**TGAGCAGAA**GTT** | LNA 3 + 3 | 2042 |
| 379 | **GGG**CAAGGGCCT**GAG** | LNA 3 + 3 | 2043 |
| 380 | **CCC**ACACTTTCT**TTA** | LNA 3 + 3 | 2044 |
| 381 | **TAG**CACCTGCTT**CCA** | LNA 3 + 3 | 2045 |
| 382 | **CGG**GGGCTTTC**TAA** | LNA 3 + 3 | 2046 |
| 383 | **CCA**TTCATGCT**TTC** | LNA 3 + 3 | 2047 |
| 384 | **AAG**CGCTGGCA**ACC** | LNA 3 + 3 | 2048 |
| 385 | **ACC**AGAGCCCT**TTG** | LNA 3 + 3 | 2049 |
| 386 | **CCC**CTAATGGC**TTC** | LNA 3 + 3 | 2050 |
| 387 | **GTC**CCCTAATG**GCT** | LNA 3 + 3 | 2051 |
| 388 | **ATC**TGCCCCT**AAT** | LNA 3 + 3 | 2052 |
| 389 | **AGA**TCTGTCCC**CTA** | LNA 3 + 3 | 2053 |
| 390 | **CGG**GTGCTGTT**GTA** | LNA 3 + 3 | 2054 |
| 391 | **ATC**ATGTCGAA**TTT** | LNA 3 + 3 | 2055 |
| 392 | **CCC**TGGATCAT**GTC** | LNA 3 + 3 | 2056 |
| 393 | **CCT**TTGAATTT**GAT** | LNA 3 + 3 | 2057 |

-continued

| SEQ ID NO. | Sequence (5' → 3') | Modification | ASPH |
|---|---|---|---|
| 394 | **TTG**CGGAAGCA**GTA** | LNA 3 + 3 | 2058 |
| 395 | **GCC**TGAGCAGA**AGT** | LNA 3 + 3 | 2059 |
| 396 | **GG**GGGCTTTC**TAA** | LNA 2 + 3 | 2060 |
| 397 | **AG**CGCTGGCA**ACC** | LNA 2 + 3 | 2061 |
| 398 | **CC**CCTAATGG**CTT** | LNA 2 + 3 | 2062 |
| 398 | **CCC**CTAATGGC**TT** | LNA 3 + 2 | 2063 |
| 399 | **TCC**CCTAATGG**CT** | LNA 3 + 2 | 2064 |
| 400 | **TC**ATGTCGAA**TTT** | LNA 2 + 3 | 2065 |
| 401 | **ATC**ATGTCGAA**TT** | LNA 3 + 2 | 2066 |

Table 1 shows the nucleic acid sequences of selected oligonucleotides of the present invention as well as the modifications of the nucleotides, wherein LNA 4+4 means 4×LNAs at the 5'- and 3'-end of the oligonucleotide are modified, wherein LNA 4+3 means 4×LNAs at the 5'-end and 3×LNAs at the 3'-end of the oligonucleotide are modified, wherein LNA 3+4 means 3×LNAs at the 5'-end and 4×LNAs at the 3'-end of the oligonucleotide are modified, wherein LNA 3+3 means 3×LNAs at the 5'- and 3'-end of the oligonucleotide are modified, wherein LNA 3+2 means 3×LNAs at the 5'-end and 2×LNAs at the 3'-end of the oligonucleotide are modified, wherein LNA 2+3 means 2×LNAs at the 5'-end and 3×LNAs at the 3'-end of the oligonucleotide are modified, wherein LNA 2+2 means 2×LNAs at the 5'- and 3'-end of the oligonucleotide are modified. Alternatively, some oligonucleotides comprise ENA 4+4, i.e., 4×ENA at the 5'- and 3'-end of the oligonucleotide are modified, or ENA 3+3, i.e, 3×ENA at the 5'- and 3'-end of the oligonucleotide are modified. Further oligonucleotides comprise 2'O-meth 4+4, wherein the oligonucleotide comprises 4×2'O-methyl modified nucleotides at the 5'- and 3'-end of the oligonucleotide, or comprises 2' fluoro 4+4, wherein the oligonucleotide comprises 4×2' fluoro modified nucleotides at the 5'- and 3'-end. Oligonucleotides comprising LNA 3+TEG comprise 3×LNAs at the 5'-end and one triethylene glycol (TEG) at the 3'-end of the oligonucleotide. Some oligonucleotides comprise LNAs which are not arranged in a row but are separated by an unlocked nucleoside having for example the sequences 3LNA+9N+1LNA+1N+2LNA, 1LNA+1N+2LNA+8N+1LNA+1N+1LNA, 2LNA+8N+2LNA+1N+1LNA, 2LNA+9N+1LNA+1N+1LNA, 2LNA+8N+1LNA+2N+1LNA, 3LNA+8N+1LNA+1N+1LNA, 3LNA+8N+1LNA+1N+1LNA, 2LNA+9N+1LNA+1N+1LNA, or 2LNA+8N+2LNA+1N+1LNA, wherein "N" is a nucleoside without locked modification. "ASPH" in combination with a number refers to the different oligonucleotides and their different modifications as described in Table 1. These modified oligonucleotides were tested e.g. in experiments shown in the examples. The antisense oligonucleotides of the present invention can be described differently, e.g., ASPH47, ASPH0047, ASPH_47 or ASPH_0047 referring to the same oligonucleotide.

In Table 2 further preferred oligonucleotides of the present invention are shown, which are variations of the sequence and/or the LNA pattern of ASPH47 (SEQ ID NO. 49).

| SEQ ID NO. | Sequence | Modification | ASPH |
|---|---|---|---|
| 402 | **AG**TATTTGGTC**TCC** | LNA 2 + 3 | 194 |
| 402 | **A**G**T**ATTTGGTC**TCC** | 1LNA + 1N + 1LNA + 8N + 3LNA | 195 |
| 402 | **AGT**ATTTGGTC**T**C**C** | 3LNA + 8N + 1LNA + 1N + 1LNA | 196 |
| 402 | **AGT**ATTTGGTCT**CC** | LNA 3 + 2 | 197 |
| 403 | **AAGT**ATTTGGTC**TC** | LNA 4 + 2 | 198 |
| 403 | **AGT**ATTTGGTC**T**C**CA** | 3LNA + 8N + 1LNA + 1N + 2LNA | 199 |
| 403 | **AGT**ATTTGGTC**TC**C**A** | 3LNA + 8N + 2LNA + 1N + 1LNA | 200 |
| 403 | **AG**T**A**TTTGGTCT**CCA** | 2LNA + 1N + 1LNA + 8N + 3LNA | 201 |
| 403 | **A**G**TA**TTTGGTCT**CCA** | 1LNA + 1N + 2LNA + 8N + 3LNA | 202 |
| 403 | **AGT**ATTTGGTCTC**CA** | LNA 3 + 2 | 203 |
| 403 | **AG**TATTTGGTCT**CCA** | LNA 2 + 3 | 204 |
| 403 | **AG**TATTTGGTC**TCCA** | LNA 2 + 4 | 205 |
| 404 | **AAG**TATTTGGT**C**T**CC** | 3LNA + 8N + 1LNA + 1N + 2LNA | 206 |
| 404 | **AAG**TATTTGGT**CT**C**C** | 3LNA + 8N + 2LNA + 1N + 1LNA | 207 |
| 404 | **AA**G**T**ATTTGGTC**TCC** | 2LNA + 1N + 1LNA + 8N + 3LNA | 208 |
| 404 | **A**A**GT**ATTTGGTC**TCC** | 1LNA + 1N + 2LNA + 8N + 3LNA | 209 |
| 404 | **AAG**TATTTGGTCT**CC** | LNA 3 + 2 | 210 |
| 404 | **AA**GTATTTGGTCT**CC** | LNA 2 + 3 | 211 |
| 49 | **CAA**AGTATTTGGTC**TCC** | LNA 3 + 3 | 212 |
| 49 | **CA**AAGTATTTGGTCT**CC** | LNA 2 + 2 | 213 |
| 49 | **C**AA**AG**TATTTGGTC**TCC** | 1LNA + 2N + 2LNA + 8N + 3LNA | 214 |
| 49 | **C**AAA**G**TATTTGGTC**TCC** | 1LNA + 3N + 1LNA + 8N + 3LNA | 215 |
| 49 | **C**AA**AG**TATTTGGT**CTCC** | 1LNA + 2N + 2LNA + 8N + 4LNA | 216 |
| 49 | **C**AA**AG**TATTTGGT**C**T**CC** | 1LNA + 2N + 2LNA + 8N + 1LNA + 1N + 2LNA | 217 |
| 49 | **C**A**AAG**TATTTGGTC**TCC** | 1LNA + 1N + 3LNA + 8N + 3LNA | 218 |
| 49 | **C**A**AA**GTATTTGGTC**TCC** | 1LNA + 1N + 2LNA + 8N + 3LNA | 219 |
| 49 | **C**AA**AGT**ATTTGGTCT**CC** | 1LNA + 2N + 3LNA + 8N + 2LNA | 220 |
| 49 | **C**AA**AGT**ATTTGGTC**T**C**C** | 1LNA + 2N + 3LNA + 8N + 1LNA + 1N + 1LNA | 221 |

-continued

| SEQ ID NO. | Sequence | Modification | ASPH |
|---|---|---|---|
| 49 | **CAA**AGTATTTGGTCTCC-TEG | LNA 3 + TEG | 222 |
| 49 | **CAAA**GTATTTGGTCTCC-TEG | LNA 4 + TEG | 223 |
| 405 | **CAAA**GTATTTGGT**CTC** | LNA 4 + 3 | M1-ASPH47 |
| 406 | **CAAA**GTATTTGGT**CT** | LNA 4 + 2 | M2-ASPH47 |
| 407 | **CAAA**GTATTTGGT**C** | LNA 4 + 1 | M3-ASPH47 |
| 408 | **AAA**GTATTTGGT**CTCC** | LNA 3 + 4 | M4-ASPH47 |
| 409 | **AAA**GTATTTGGT**CTC** | LNA 3 + 3 | M5-ASPH47 |
| 410 | **AAA**GTATTTGGT**CT** | LNA 3 + 2 | M6-ASPH47 |
| 411 | **AAA**GTATTTGGT**C** | LNA 3 + 1 | M7-ASPH47 |
| 412 | **AA**GTATTTGGT**CT** | LNA 2 + 2 | M10-ASPH47 |
| 413 | **AA**GTATTTGGT**C** | LNA 2 + 1 | M11-ASPH47 |
| 414 | **A**GTATTTGGT**CTC** | LNA 1 + 3 | M13-ASPH47 |
| 415 | **A**GTATTTGGT**CT** | LNA 1 + 2 | M14-ASPH47 |
| 416 | **A**GTATTTGGT**C** | LNA 1 + 1 | M15-ASPH47 |

The description of the modifications in Table 2 corresponds to the description provided in Table 1; in addition, LNA nucleosides are indicated in the sequence in bold letters, and triethylene glycol is abbreviated as TEG in Table 2.

For the purpose of clarity and a concise description, features are described herein as part of the same or separate embodiments, however, it will be appreciated that the scope of the invention may include embodiments having combinations of all or some of the features described.

The following examples will serve to further illustrate the present invention without, at the same time, however, constituting any limitation thereof. On the contrary, it is to be clearly understood that the scope of the present invention refers to various other embodiments, modifications, and equivalents thereof which, after reading the description herein, may suggest themselves to those skilled in the art without departing from the spirit of the invention.

EXAMPLES

In the following examples, the effect of the oligonucleotides listed in Tables 1 and 2 have been tested in view of the reduction and inhibition, respectively, of TGF-beta1 and/or TGF-beta2 expression. SEQ ID NO. 144 (T-LNA: CGGCATGTCTATTTTGTA, wherein 3× nucleotides at the 5'- and 3'-end are LNAs) and SEQ ID NO. 145 (scr-LNA:

CGTTTAGGCTATGTACTT, wherein 3× nucleotides at the 5'- and 3'-end are LNAs) are used as control oligonucleotides, wherein SEQ ID NO. 145 (negative control) is the scrambled form of SEQ ID NO. 144 (positive control). The cells were either transfected in the presence of a transfecting agent (e.g., Lipofectamine), or in the absence of any transfecting agent (gymnotic transfection or unassisted transfection or gymnotic delivery). As in case of a gymnotic transfection the entry of the oligonucleotide into the cell solely depends on the interaction of the oligonucleotide and the cell, and no compound supports the entry, gymnotic transfection reflects better conditions of the in vivo experimental settings.

Example 1

Human A172 glioma cells were transfected with 10 nM of ASPH01, ASPH02, ASPH03, ASPH04, ASPH05, ASPH06, ASPH07, ASPH08, ASPH09, ASPH10, ASPH11, ASPH12, ASPH13, ASPH14, ASPH15, ASPH16, ASPH17, ASPH18, ASPH19, ASPH20, ASPH21, ASPH22, ASPH24, ASPH25, ASPH26, ASPH27, ASPH29, ASPH30, ASPH31, ASPH32, ASPH33, ASPH34, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, ASPH52, ASPH53, and ASPH54 (see FIG. 5*a*); ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH95, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119 (see FIG. 5*b*), or ASPH36, ASPH71, ASPH73, ASPH120, ASPH121, ASPH122, ASPH123, ASPH124, ASPH125, ASPH126, ASPH127, ASPH128, ASPH129, ASPH130, ASPH131, ASPH132, ASPH133, ASPH134, ASPH135, ASPH136, ASPH137, ASPH138, ASPH139, ASPH140, ASPH141, ASPH142, ASPH143, ASPH145, ASPH146, ASPH147, ASPH148, ASPH149, ASPH150, ASPH151, ASPH152, ASPH153, ASPH154, ASPH155, ASPH157, ASPH158, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183 (see FIG. 5*c*), and the controls of SEQ ID NO. 144 and 145, respectively, in the presence of a transfecting agent. The expression of TGF-beta1 and TGF-beta2 mRNA was determined 24 h after transfection. Significant reduction of the expression of TGF-beta1 and TGF-beta2 mRNA is demonstrated in FIG. 5*a*) to 5*c*). The dual TGF-beta1 and TGF-beta2 reactive oligonucleotides ASPH01, ASPH02, ASPH03, ASPH04, ASPH05, ASPH06, ASPH07, ASPH08 and ASPH09 show a significant reduction of the expression of both TGF-beta1 and TGF-beta2 mRNA, while the selective TGF-beta2 oligonucleotides significantly inhibit TGF-beta2 mRNA expression.

Example 2

Human Panc-1 pancreatic cancer cells were transfected with 10 nM of ASPH01, ASPH02, ASPH03, ASPH04, ASPH05, ASPH06, ASPH07, ASPH08, ASPH12, ASPH14, ASPH17, ASPH18, ASPH20, ASPH21, ASPH22, ASPH24, ASPH25, ASPH26, ASPH27, ASPH29, ASPH30, ASPH31, ASPH32, ASPH33, ASPH35, ASPH36, ASPH37, ASPH38, ASPH39, ASPH40, ASPH41, ASPH42, ASPH43, ASPH44, ASPH45, ASPH46, ASPH47, ASPH48, ASPH49, ASPH50, ASPH51, and ASPH52 (see FIG. 6*a*); ASPH36, ASPH60, ASPH61, ASPH62, ASPH63, ASPH64, ASPH65, ASPH66, ASPH67, ASPH68, ASPH69, ASPH70, ASPH71, ASPH72, ASPH73, ASPH74, ASPH75, ASPH76, ASPH77, ASPH78, ASPH79, ASPH80, ASPH81, ASPH82, ASPH83, ASPH84, ASPH85, ASPH86, ASPH87, ASPH88, ASPH89, ASPH90, ASPH91, ASPH92, ASPH93, ASPH94, ASPH96, ASPH97, ASPH98, ASPH99, ASPH100, ASPH101, ASPH102, ASPH103, ASPH104, ASPH105, ASPH106, ASPH107, ASPH108, ASPH109, ASPH110, ASPH111, ASPH112, ASPH113, ASPH114, ASPH115, ASPH116, ASPH117, ASPH118, and ASPH119 (see FIG. 6*b*), or ASPH36, ASPH71, ASPH73, ASPH120, ASPH121, ASPH122, ASPH127, ASPH128, ASPH129, ASPH130, ASPH131, ASPH132, ASPH133, ASPH135, ASPH136, ASPH137, ASPH139, ASPH141, ASPH142, ASPH143, ASPH145, ASPH146, ASPH147, ASPH149, ASPH150, ASPH151, ASPH152, ASPH153, ASPH154, ASPH155, ASPH157, ASPH160, ASPH161, ASPH162, ASPH163, ASPH164, ASPH165, ASPH166, ASPH167, ASPH168, ASPH169, ASPH170, ASPH171, ASPH172, ASPH173, ASPH174, ASPH175, ASPH176, ASPH177, ASPH178, ASPH179, ASPH180, ASPH181, ASPH182, and ASPH183 (see FIG. 6*c*) and the controls of SEQ ID NO. 144 and 145, respectively, in the presence of a transfecting agent. The expression of TGF-beta1 and TGF-beta2 mRNA was determined 24 h after transfection. Significant reduction of the expression of TGF-beta1 and TGF-beta2 mRNA is demonstrated in FIG. 6*a*) to 6*c*). The dual TGF-beta1 and TGF-beta2 reactive oligonucleotides ASPH01, ASPH02, ASPH03, ASPH04, ASPH05, ASPH06, ASPH07, and ASPH08 show again a significant reduction of the expression of both TGF-beta1 and TGF-beta2 mRNA, while the selective TGF-beta2 oligonucleotides significantly inhibit TGF-beta2 mRNA expression.

Example 3

In further experiments the inhibitory effect of ASPH01, ASPH03, ASPH05, ASPH17, ASPH18, ASPH22, ASPH26, ASPH27, ASPH33, ASPH36, ASPH37, ASPH41, ASPH42, ASPH45, ASPH46, ASPH47, ASPH48, ASPH49, ASPH64, ASPH65, ASPH66, ASPH69, ASPH71, ASPH80, ASPH82, ASPH88, ASPH89, ASPH90, ASPH98, ASPH99, ASPH102, ASPH105, ASPH115, ASPH121, ASPH140, ASPH153, ASPH165, ASPH171, ASPH178, ASPH181, ASPH184, ASPH185, ASPH186, ASPH187, ASPH188, ASPH189, and of the controls of SEQ ID NO.144 and SEQ ID NO. 145, respectively, was tested in A172 cells. A172 cells were transfected with these modified oligonucleotides in doses of 20 nM, 4 nM, 0.8 nM, 0.16 nM, and 0.04 nM, respectively, in the presence of a transfecting agent. The remaining TGF-beta2 mRNA was measured 24 h after transfection. TGF-beta2 values were normalized to GAPDH and oligonucleotide concentrations resulting in 50% reduction of TGF-beta2 mRNA (=$IC_{50}$ values) were calculated. All $IC_{50}$ values were referenced to the $IC_{50}$ value of ASPH_036 (ASPH36) that was 0.33 nM and the results are shown as fold-difference of the $IC_{50}$ value of ASPH_036 Table 3:

| Oligonucleotide | Fold $IC_{50}$ referenced to ASPH_036 |
|---|---|
| ASPH_080 | 0.591 |
| ASPH_069 | 0.673 |
| ASPH_065 | 0.773 |
| ASPH_105 | 0.882 |
| ASPH_036 | 1.000 |
| ASPH_046 | 1.142 |
| ASPH_098 | 1.182 |
| ASPH_071 | 1.237 |
| ASPH_026 | 1.242 |
| ASPH_047 | 1.303 |
| ASPH_088 | 1.455 |
| ASPH_185 | 1.456 |
| ASPH_115 | 1.545 |
| ASPH_153 | 1.665 |
| ASPH_181 | 1.918 |
| ASPH_027 | 2.000 |
| ASPH_089 | 2.091 |
| ASPH_102 | 2.091 |
| ASPH_041 | 2.182 |
| ASPH_018 | 2.212 |
| ASPH_049 | 2.455 |
| ASPH_022 | 2.485 |
| ASPH_188 | 2.639 |
| ASPH_189 | 2.660 |
| ASPH_042 | 2.848 |
| ASPH_178 | 3.147 |
| ASPH_048 | 3.182 |
| ASPH_066 | 3.182 |
| ASPH_033 | 3.182 |
| ASPH_045 | 3.636 |
| ASPH_121 | 3.644 |
| ASPH_171 | 3.871 |
| ASPH_005 | 3.954 |
| ASPH_003 | 4.111 |
| ASPH_082 | 4.818 |
| ASPH_037 | 5.303 |
| ASPH_099 | 5.545 |
| ASPH_090 | 6.727 |
| ASPH_165 | 7.175 |
| ASPH_186 | 7.655 |
| ASPH_017 | 8.455 |
| ASPH_001 | 9.242 |
| ASPH_187 | 9.990 |
| ASPH_064 | 10.091 |
| ASPH_140 | 11.482 |
| ASPH_184 | 12.224 |
| SEQ ID NO 144 | 17.212 |
| SEQ ID NO 145 | n.a |

All the modified oligonucleotides show an $IC_{50}$ in a low nanomolar to picomolar range, which is markedly lower than $IC_{50}$ to the control oligonucleotide of SEQ ID NO. 144; the $IC_{50}$ of the control of SEQ ID NO. 145 was not calculable.

Example 4

Panc-1 cells were treated with 3.3 μM of each of ASPH17, ASPH18, ASPH22, ASPH25, ASPH33, ASPH35, ASPH36, ASPH41, ASPH42, ASPH45, ASPH46, ASPH47, ASPH48, ASPH49, ASPH65, ASPH66, ASPH67, ASPH69, ASPH71, ASPH79, ASPH80, ASPH82, ASPH88, ASPH89, ASPH90, ASPH91, ASPH98, ASPH99, ASPH102, ASPH105, ASPH111, ASPH115, ASPH119, ASPH121, ASPH139, ASPH140, ASPH146, ASPH151, ASPH153, ASPH165, ASPH171, ASPH172, ASPH176, ASPH178, ASPH180, and ASPH183, or the controls of SEQ ID NO. 144 and 145, respectively, in the absence of a transfecting agent (gymnotic transfection). The inhibitory effect of the modified oligonucleotides on expression of TGF-beta1 and TGF-beta2 mRNA, respectively, was determined 72 h after treatment start. Under gymnotic transfection experimental conditions, the oligonucleotides enter the cells and strongly inhibit the expression of TGF-beta2 mRNA. The results of the experiments are shown in FIG. 7.

Example 5

In further experiments Panc-1 cells were transfected with 10 μM of modified oligonucleotides ASPH01, ASPH03, ASPH05, ASPH09, ASPH17, ASPH18, ASPH22, ASPH35, ASPH36, ASPH37, ASPH41, ASPH45, ASPH46, ASPH47, and ASPH48, or the controls of SEQ ID NO. 144 and 145, respectively, in the absence of a transfecting agent (gymnotic transfection or gymnotic delivery). The oligonucleotides were added to the cells for 2 days, after which oligonucleotide containing incubation medium was changed, and further incubation for 2 days was carried out. Expression of TGF-beta1 mRNA (see FIG. 8*a*) and TGF-beta2 mRNA (see FIG. 8*b*) was then measured and normalized to HPRT1 (Hypoxanthin-Phosphoribosyl-Transferase1). Cell supernatants were analysed for TGF-beta1 (see FIG. 9*a*) and TGF-beta2 (see FIG. 9*b*) protein by ELISA. Under gymnotic delivery experimental conditions, the double reactive oligonucleotides ASPH01, ASPH03, ASPH05, and ASPH09 significantly inhibit the expression of TGF-beta1 and TGF-beta2 on mRNA, and likewise on the protein level. All the other oligonucleotides significantly inhibit the expression of TGF-beta2 on mRNA and protein level.

Example 6

In another experiment dose dependency of the inhibitory effect of modified oligonucleotides of the present invention was tested. Panc-1 cells were treated with 15 μM, 10 μM, 7.5 μM, 5 μM, 2.5 μM, 1.25 μM, or 0.625 μM ASPH05 or ASPH36, or the controls of SEQ ID NO. 144 and 145, respectively, without using a transfection reagent. The oligonucleotides were added to the cells for 2 days. Thereafter the incubation media containing the oligonucleotides were changed and cells were incubated for 2 further days. Thereafter (total treatment time: 4 days) the expression of TGF-beta1 (see FIG. 10*a*) and TGF-beta2 (see FIG. 10*b*) mRNA depending on the oligonucleotide concentration was measured. The dual TGF-beta1 and TGF-beta2 reactive oligonucleotide ASPH05 shows a marked dose dependent inhibition of both TGF-beta1 and TGF-beta2 mRNA expressions, and ASPH36 inhibits specifically the expression of TGF-beta2 mRNA in a dose-dependent manner.

Example 7

Mouse SMA-560 glioma cells were transfected with 10 nM ASPH01, ASPH03, ASPH05, ASPH09, ASPH17, ASPH18, ASPH22, ASPH26, ASPH36, ASPH37, ASPH41, ASPH42, ASPH45, ASPH46, ASPH47, or ASPH48, or the controls of SEQ ID NO. 144 and 145, respectively, in the presence of a transfecting agent. 24 h after transfection, the inhibition of the expression of TGF-beta1 (white columns) and TGF-beta2 (black columns) mRNA was determined. The dual TGF-beta1 and TGF-beta2 reactive oligonucleotide ASPH09 inhibits the expression of the mouse TGF-beta1 mRNA, and the other oligonucleotides tested strongly inhibit the expression of the mouse TGF-beta2 mRNA. The results are presented in FIG. 11.

Example 8

Female athymic nude mice (Hsd:Athymic Nude-Foxn1$^{nu}$) were treated for 5 consecutive days with 14 mg/kg or 50 mg/kg of oligonucleotide ASPH01, ASPH03, ASPH05, ASPH17, ASPH22, ASPH37, ASPH41, ASPH45, ASPH46, ASPH47, or ASPH48, and control of SEQ ID NO. 145 or saline by subcutaneous injection. The day after the last treatment, the mice were sacrificed. Mouse TGF-beta2 mRNA was quantified in kidney tissue lysates. In FIG. 12, data—representing TGF-beta2 to GAPDH mRNA ratio—are shown as a box plot in which median values and min. and max. values are presented (data expressed as n=4, except ASPH46 group n=3). All the tested oligonucleotides inhibited the expression of TGF-beta2 mRNA in the kidney of these mice.

Example 9

In another experiments Panc-1 cells were transfected with 10 μM of modified oligonucleotide ASPH09 or the control of SEQ ID NO. 145 in the absence of a transfecting agent (gymnotic transfection). The oligonucleotides were added to the cells for 2 days, after which oligonucleotide containing incubation medium was changed, and further incubation for 2 days was carried out. Expression of TGF-beta3 mRNA (see FIG. 13) was then measured and normalized to HPRT1 (Hypoxanthin-Phosphoribosyl-Transferase1). Under gymnotic transfection experimental conditions, the triple reactive oligonucleotide ASPH09 significantly inhibits the expression of TGF-beta3 mRNA.

Example 10

Panc-1 cells were treated with 10 μM, 3.3 μM, 1.1 μM, 0.37 μM, and 0.12 μM of ASPH03, ASPH36, ASPH45, ASPH47, ASPH65, ASPH69, ASPH71, ASPH80, ASPH115, ASPH 121, ASPH153, ASPH185, and ASPH189, respectively, in the absence of a transfecting agent (gymnotic transfection). The inhibitory effect of the modified oligonucleotides on expression of TGF-beta2 mRNA, was determined 72 h after treatment start. TGF-beta2 values were normalized to GAPDH and oligonucleotide concentrations resulting in 50% reduction of TGF-beta2 mRNA (=$IC_{50}$ values) were calculated. Under gymnotic transfection experimental conditions, the oligonucleotides enter the cells and strongly inhibit the expression of TGF-beta2 mRNA. The results of the experiments are shown in Table 4:

| Name | IC50 (μM) |
|---|---|
| ASPH_065 | 0.37 |
| ASPH_071 | 0.371 |
| ASPH_115 | 0.6 |
| ASPH_069 | 0.655 |
| ASPH_047 | 0.78 |
| ASPH_080 | 0.81 |
| ASPH_153 | 0.9 |
| ASPH_045 | 1.21 |
| ASPH_121 | 1.27 |
| ASPH_036 | 1.5 |
| ASPH_185 | 3.05 |
| ASPH_003 | 3.62 |
| ASPH_189 | 4.26 |

All the modified oligonucleotides show an $IC_{50}$ in the low micromolar or even submicromolar range, showing that they have very high potency even without the requirement of a transfection reagent.

Example 11

Panc-1 cells were treated with 10 μM, 3.3 μM, 1.1 μM, 0.37 μM, and 0.12 μM of ASPH47, ASPH190, ASPH191, ASPH192, and ASPH193 in the absence of a transfecting agent (gymnotic transfection). The inhibitory effect of the modified oligonucleotides on expression of TGF-beta2 mRNA, was determined 72 h after treatment start. TGF-beta2 values were normalized to GAPDH and oligonucleotide concentrations resulting in 50% reduction of TGF-beta2 mRNA (=$IC_{50}$ values) were calculated. Under gymnotic transfection experimental conditions, the oligonucleotides enter the cells and strongly inhibit the expression of TGF-beta2 mRNA. The results of the experiments are shown in Table 5:

| Name | IC50 (μM) |
|---|---|
| ASPH_047 | 0.76 |
| ASPH_190 | 0.18 |
| ASPH_191 | 0.97 |
| ASPH_192 | 0.145 |
| ASPH_193 | 0.144 |

All the modified oligonucleotides show an $IC_{50}$ in the submicromolar to lower submicromolar range, showing that they have extremely high potency even without the requirement of a transfection reagent.

Example 12

Human Panc-1 pancreatic cancer cells were transfected with 10 nM of ASPH05, ASPH09, ASPH1000, ASPH1001, ASPH1002, ASPH1003, ASPH1004, ASPH1005, ASPH1006, ASPH 1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH 1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1054, ASPH1055, ASPH1056, ASPH1057, ASPH1058, ASPH1059, ASPH1060, or ASPH1061 (see FIG. 14) and the control of SEQ ID NO. 145, in the presence of a transfecting agent. The expression of TGF-beta1 mRNA was determined 24 h after transfection. Significant reduction of the expression of TGF-beta1 in Panc-1 cells is demonstrated in FIG. 14.

Example 13

Mouse SMA-560 glioma cells were transfected with 10 nM of ASPH09, ASPH1000, ASPH1001, ASPH1002, ASPH1003, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH 1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, or ASPH1062 (see FIG. 15) and the control of SEQ ID NO. 145, in the presence of a transfecting agent. The expression of TGF-beta1 mRNA was determined 24 h after transfection. Significant reduction of the expression of TGF-beta1 in SMA-560 cells is demonstrated in FIG. 15.

Example 14

In these experiments human A172 glioma cells were transfected with 10 nM of ASPH05, ASPH09, ASPH1000, ASPH1001, ASPH1002, ASPH1004, ASPH1005, ASPH1006, ASPH1007, ASPH1008, ASPH1009, ASPH1010, ASPH1011, ASPH1012, ASPH1013, ASPH1014, ASPH1015, ASPH1016, ASPH1017, ASPH1018, ASPH1019, ASPH1020, ASPH1021, ASPH1022, ASPH1023, ASPH1024, ASPH1026, ASPH1027, ASPH1028, ASPH1029, ASPH1030, ASPH1031, ASPH1032, ASPH1033, ASPH1034, ASPH1035, ASPH1036, ASPH1038, ASPH1039, ASPH1040, ASPH1041, ASPH1042, ASPH1043, ASPH1044, ASPH1045, ASPH1046, ASPH1047, ASPH1048, ASPH1049, ASPH1050, ASPH1051, ASPH1052, ASPH1053, ASPH1054, ASPH1056, ASPH1057, ASPH1058, ASPH1059, ASPH1060, ASPH1061, or ASPH1062 (see FIG. 16), and the control of SEQ ID NO. 145, in the presence of a transfecting agent. The expression of TGF-beta1 and TGF-beta2 mRNA was determined 24 h after transfection. Significant reduction of the expression of TGF-beta1 mRNA is demonstrated in FIG. 16. The dual TGF-beta1 and TGF-beta2 reactive oligonucleotides ASPH05 shows a significant reduction of the expression of both TGF-beta1 and TGF-beta2 mRNA, while the selective TGF-beta1 oligonucleotides significantly inhibit TGF-beta1 mRNA expression.

Example 15

Panc-1 cells were treated with 3.3 μM of ASPH05, ASPH09, ASPH1000, ASPH1001, ASPH1002, ASPH1004, ASPH1006, ASPH1007, ASPH1008, ASPH1009, ASPH1010, ASPH1011, ASPH1012, ASPH1013, ASPH1014, ASPH1015, ASPH1017, ASPH1018, ASPH1019, ASPH1020, ASPH1021, ASPH1022, ASPH1024, ASPH1026, ASPH1027, ASPH1028, ASPH1029, ASPH1032, ASPH1033, ASPH1034, ASPH1035, ASPH1036, ASPH1037, ASPH1038, ASPH1039, ASPH1040, ASPH1041, ASPH1042, ASPH1043, ASPH1044, ASPH1045, ASPH1046, ASPH1047, ASPH1049, ASPH1050, ASPH1051, ASPH1052, ASPH1053, ASPH1054, ASPH1055, ASPH1056, ASPH1057, ASPH1058, ASPH1059, ASPH1060, ASPH1061, or ASPH1062, or the control of SEQ ID NO. 145 in the absence of a transfecting agent (gymnotic transfection or gymnotic delivery). The inhibitory effect of the modified oligonucleotides on expression of TGF-beta1 and TGF-beta2 mRNA, respectively, was determined 72 h after treatment start. Significant reduction of the expression of TGF-beta1 mRNA is demonstrated in FIG. 17. The dual TGF-beta1 and TGF-beta2 reactive oligonucleotides ASPH05 shows a significant reduction of the expression of both TGF-beta1 and TGF-beta2 mRNA, while the selective TGF-beta1 oligonucleotides significantly inhibit TGF-beta1 mRNA expression.

Example 16

Human A172 cells were treated with 10 nM (in the presence of a transfecting agent), of ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132, or the positive control ASPH1047. The expression of TGF-beta1 (black column), TGFβbeta2 (white column) and TGF-beta3 (striped column) mRNA was determined 24 h after transfection. Significant reduction of the expression of TGF-beta1 mRNA is demonstrated in FIG. 18. The pan-specific TGF-beta1, TGF-beta2 and TGF-beta3 reactive oligonucleotides ASPH0009, ASPH1096, ASPH1131, and ASPH1132 show a significant reduction of the expression of all three isoformes, while the selective TGF-beta1 oligonucleotides significantly inhibit TGF-beta1 mRNA expression.

Example 17

Either Panc-1 cells (FIG. 19*a*) or RenCa cells (FIG. 19*b*) were treated with 3.3 μM of ASPH09, ASPH1047, ASPH1051, ASPH1059, ASPH1063, ASPH1064, ASPH1065, ASPH1066, ASPH1067, ASPH1068, ASPH1069, ASPH1070, ASPH1071, ASPH1072, ASPH1073, ASPH1074, ASPH1075, ASPH1076, ASPH1077, ASPH1078, ASPH1079, ASPH1080, ASPH1081, ASPH1082, ASPH1083, ASPH1084, ASPH1085, ASPH1086, ASPH1087, ASPH1088, ASPH1089, ASPH1090, ASPH1091, ASPH1092, ASPH1093, ASPH1094, ASPH1095, ASPH1097, ASPH1098, ASPH1099, ASPH1100, ASPH1101, ASPH1102, ASPH1103, ASPH1104, ASPH1105, ASPH1106, ASPH1107, ASPH1108, ASPH1109, ASPH1110, ASPH1111, ASPH1112, ASPH1113, ASPH114, ASPH1115, ASPH1116, ASPH1117, ASPH1118, ASPH1119, ASPH1120, ASPH1121, ASPH1122, ASPH1123, ASPH1124, ASPH1125, ASPH1126, ASPH1127, ASPH1128, ASPH1129, ASPH1130, ASPH1131, and ASPH1132, respectively, or the positive control ASPH1047 in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta1 mRNA is demonstrated in FIG. 18. The pan-specific TGF-beta1, TGF-beta2 and TGF-beta3 reactive oligonucleotides ASPH09, ASPH1096, ASPH1131, and ASPH1132 show a significant reduction of the expression of all three isoforms, while the selective TGF-beta1 oligonucleotides significantly inhibit TGF-beta1 mRNA expression.

Example 18

Mice bearing subcutaneous human pancreatic carcinoma Panc-1 tumors were treated with 1, 3, 10, and 30 mg/kg of ASPH47 under various treatment schedules: Q1Dx1-d6 (single SC injection, termination 5 days later), Q1Dx5-d6 (daily SC injection for 5 days, termination 24 hours later), and Q1Dx5-d10 (daily SC injection for 5 days, termination 5 days later). There was a dose dependent down-regulation of TGF-beta 2 mRNA in the kidney of these animals. TGF-beta 2 down-regulation was persistent up to 5 days after the last treatment with ASPH47, even after only single administration. TGF-beta 2 expression was detected by bDNA assay (branched DNA assay, which is a sandwich nucleic acid hybridization method that uses bDNA molecules to amplify signal from captured target RNA) and normalized to GAPDH. As shown in FIG. 23, data—representing TGF-beta2 to GAPDH mRNA ratio—are shown as a box plot in which median values and min. and max. values are presented (data expressed as n=10, except n=9 for vehicle and 3 mg/kg Q1Dx1 d6 groups).

Example 19

Mice bearing subsutaneous human pancreatic carcinoma Panc-1 tumors on both left and right flanks were treated with a daily injection of 1, 5, 15 or 50 mg/kg oligonucleotides for five consecutive days. The tumors were collected 24 hours after the last treatment and snap frozen. TGF-beta mRNA expression in tumors was detected by bDNA assay. Data—representing TGF-beta2 to GAPDH mRNA ratio—are shown as a box plot in which median values and min. and max. values are presented (data expressed as n=5). TGF-beta2 mRNA was down-regulated in tumors treated with various oligonucleotides (FIG. 24). There was no significant TGF-beta1 mRNA down-regulation in those groups (data not shown).

Example 20

Mice bearing subcutaneous human renal cell carcinoma 786-O tumors on both left and right flanks were treated with a daily injection of 50 mg/kg oligonucleotides for five consecutive days. The tumors were collected 24 hours after the last treatment and snap frozen. TGF-beta mRNA expression in tumors was detected by bDNA assay. There was significant down-regulation of TGF-beta2 mRNA in tumors treated with ASPH05, ASPH17, ASPH26, ASPH36, ASPH45, ASPH47, ASPH71, ASPH82, ASPH98, and ASPH105, respectively, (FIG. 25). Data—representing TGF-beta2 to GAPDH mRNA ratio—are shown as a box plot in which median values and min. and max. values are presented (data expressed as n=10, except for ASPH71 group n=9).

Example 21

Human Panc-1 cells were transfected with 20, 6.67, 2.22, 0.74, 0.25, 0.08 or 0.009 μM of the modified oligonucleotides ASPH47, ASPH1047, ASPH1106, ASPH1132, or ASPH47 in combination with ASPH1047; results are shown in FIG. 26*a* to 26*e*). Negative control is the scrambled oligonucleotide (scr LNA) of SEQ ID No. 145 (FIG. 26*f*). All cells were transfected in the absence of a transfecting agent (gymnotic transfection or gymnotic delivery). The modified oligonucleotides were added to the cells for 3 days, which were incubated at 37° C. Thereafter the oligonucleotide containing medium was exchanged with fresh oligonucleotide containing medium and cells were incubated for further 4 days at 37° C. TGF-beta1 and TGF-beta2 protein levels in cell supernatants were determined by ELISA. ASPH47 specifically inhibits the expression of TGF-beta2 in a dose-dependent manner and does not have any target inhibiting effect on TGF-beta1 (FIG. 26*a*). ASPH1047 specifically inhibits the expression of TGF-beta1 and does not have any target inhibiting effect on TGF-beta2 (FIG. 26*b*), or only a slight TGF-beta2 inhibiting effect at higher concentrations. Also ASPH1106 inhibits TGF-beta1 expression in a dose dependent manner (FIG. 26*c*). The multispecific ASPH 1132 shows a dose-dependent inhibition of the expression of TGF-beta1 and TGF-beta2 protein (FIG. 26*d*). If ASPH47 and ASPH1047 are combined, the expression of both, TGF-beta1 and TGF-beta2 protein is inhibited in a dose-dependent manner (FIG. 26*e*). The scrLNA of SQE ID No. 145 does not show any inhibiting effect on the expression of neither TGF-beta1 nor TGF-beta2, even if the concentrations were doubled (40, 13.33, 4.44, 1.48, 0.49, 0.16, 0.05, or 0.02 μM) in comparison to the individual concentrations of ASPH47, ASPH1047, ASPH1106, or ASPH1132. Results for TGF-beta1 are indicated in diamonds, and results for TGF-beta2 in squares in FIGS. 26*a* to 26*f*.

Example 22

Either Panc-1 cells (FIG. 27*a*) or RenCa cells (FIG. 27*b*) were treated with 1.1 μM of ASPH190, ASPH191, ASPH192, ASPH193, ASPH194, ASPH195, ASPH196, ASPH197, ASPH198, ASPH199, ASPH200, ASPH201, ASPH202, ASPH203, ASPH204, ASPH205, ASPH206, ASPH207, ASPH208, ASPH209, ASPH210, ASPH211, ASPH212, ASPH213, ASPH214, ASPH215, ASPH216, ASPH217, ASPH218, ASPH219, ASPH220, ASPH221, ASPH222, and ASPH223, respectively, in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta2 mRNA is demonstrated in FIGS. 27*a* and 27*b*. The negative control is scrambled LNA (scr LNA) of SEQ ID No. 145.

Example 23

Panc-1 cells were treated with 10 μM, 3.3 μM, 1.1 μM, 0.37 μM, and 0.12 μM of ASPH47, M1-ASPH47, M2-ASPH47, M3-ASPH47, M4-ASPH47, M5-ASPH47, M6-ASPH47, M7-ASPH47, M8-ASPH47, M9-ASPH47, M10-ASPH47, M11-ASPH47, M12-ASPH47, M13-ASPH47, M14-ASPH47, or M15-ASPH47 in the absence of a transfecting agent (gymnotic transfection or gymnotic delivery). The inhibitory effect of the modified oligonucleotides on expression of TGF-beta2 mRNA, was determined 72 h after treatment start. TGF-beta2 values were normalized to GAPDH and oligonucleotide concentrations resulting in 50% reduction of TGF-beta2 mRNA (=$IC_{50}$ values) were calculated. Under gymnotic transfection experimental conditions, the oligonucleotides enter the cells and strongly inhibit the expression of TGF-beta2 mRNA. The results of the experiments are shown in Table 6:

| oligos | $IC_{50}$ (μM) |
|---|---|
| M1_ASPH_0047 | 0.3 |
| M2_ASPH_0047 | 0.49 |
| M3_ASPH_0047 | 1.75 |
| M4_ASPH_0047 | 0.95 |
| M5_ASPH_0047 | 0.85 |

-continued

| oligos | $IC_{50}$ (μM) |
|---|---|
| M6_ASPH_0047 | 1.49 |
| M7_ASPH_0047 | n.a. |
| M8_ASPH_0047 | 0.89 |
| M9_ASPH_0047 | 1.05 |
| M10_ASPH_0047 | 7.75 |
| M11_ASPH_0047 | n.a. |
| M12_ASPH_0047 | 1.58 |
| M13_ASPH_0047 | 1.91 |
| M14_ASPH_0047 | n.a. |
| M15_ASPH_0047 | n.a. |
| ASPH_0047 | 0.348 |

Most of the modified oligonucleotides show an $IC_{50}$ in the submicromolar to lower submicromolar range, showing that they have extremely high potency even without the requirement of a transfection reagent.

Example 24

Human Panc-1 pancreatic cancer cells (FIG. 28*a*) or mouse RenCa renal cell carcinoma cells (FIG. 28*b*) were treated with 3.3 μM of ASPH0009, ASPH1132, ASPH2000, ASPH2001, ASPH2002, ASPH2003, ASPH2004, ASPH2005, ASPH2006, ASPH2007, ASPH2009, ASPH2010, ASPH2012, ASPH2013, ASPH2014 ASPH2015, ASPH2016, ASPH2017, ASPH2018, ASPH2019, ASPH2020, ASPH2021, ASPH2023, ASPH2024, ASPH2025, ASPH23026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2043, ASPH2044, ASPH2045, ASPH2046, ASPH2047, ASPH2048, ASPH2049, ASPH2050, ASPH2052, ASPH2053, ASPH2054, ASPH2055, ASPH2056, ASPH2057, ASPH2060, ASPH2061, ASPH2062, ASPH2063, ASPH2064, ASPH2065, or ASPH2066 in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta3 mRNA is shown in FIGS. 28*a* and 28*b*. As anticipated from the sequences, the TGF-beta1, -beta2 and -beta3 reactive oligonucleotide ASPH_0009 (pan-selective) and ASPH_1132 that has 100% homology to mRNAs of human TGF-beta1 and -beta3 but has a mismatch to TGF-beta2 show significant reduction of the expression of all three isoforms. The selective TGF-beta3 oligonucleotides only significantly inhibit TGF-beta3 mRNA expression.

Example 25

Human A172 glioma cells were treated for 24 h with 10 nM (in the presence of a transfecting agent), of ASPH0009, ASPH1132, ASPH2000, ASPH2001, ASPH2002, ASPH2003, ASPH2004, ASPH2006, ASPH2007, ASPH2008, ASPH2009, ASPH2010, ASPH2011, ASPH2012, ASPH2013, ASPH2014, ASPH2016, ASPH2017, ASPH2018, ASPH2020, ASPH2021, ASPH2022, ASPH2023, ASPH2024, ASPH2025, ASPH2026, ASPH2027, ASPH2028, ASPH2029, ASPH2030, ASPH2031, ASPH2032, ASPH2033, ASPH2034, ASPH2035, ASPH2036, ASPH2037, ASPH2038, ASPH2039, ASPH2040, ASPH2041, ASPH2042, ASPH2043, ASPH2044, ASPH2045, ASPH2047, ASPH2049, ASPH2050, ASPH2051, ASPH2052, ASPH2053, ASPH2054, ASPH2056, ASPH2057, ASPH2058, ASPH2059, ASPH2060, ASPH2061, ASPH2062, ASPH2063, or ASPH2066. The expression of TGF-beta1 (black column), TGF-beta2 (white column) and TGF-beta3 (striped column) mRNA was then determined from cell extracts by bDNA assay. Significant reduction of the expression of TGF-beta3 mRNA is shown in FIG. 29. As anticipated from the sequences, the TGF-beta1, -beta2 and -beta3 reactive oligonucleotide) ASPH_0009 (pan-selective) and ASPH_1132 that has 100% homology to mRNAs of human TGF-beta1 and -beta3 but has a mismatch to TGF-beta2 show significant reduction of the expression of all three isoforms. The selective TGF-beta3 oligonucleotides only significantly inhibit TGF-beta3 mRNA expression.

Example 26

Target mRNA Downregulation in Rabbit Cells

Sequences of selected oligonucleotides were aligned with rabbit mRNA sequences of TGF-beta1 and 2. ASPH_0036 (TGF-beta2 selective antisense oligonucleotide, based on human mRNA sequence) showed 100% homology with rabbit TGF-beta2 mRNA, while ASPH_1059 (TGF-beta1 selective antisense oligonucleotide, based on human mRNA sequence) showed 100% homology with rabbit TGF-beta1 mRNA.

Rabbit Rab-9 skin fibroblasts were treated with 5 nM or 20 nM of either ASPH_0036 and ASPH_1059 in the presence of a transfecting agent for 24 hr. The expression of TGF-beta1 and TGF-beta2 mRNA was then determined in cell extracts by bDNA assay. Significant reduction of the expression of TGF-beta1 mRNA (51 and 77% at 5 and 20 nM, respectively) was achieved with ASPH_1059. Significant reduction of TGF-beta2 mRNA (79 and 80% at 5 and 20 nM, respectively) was achieved with ASPH_0036.

Example 27

Tissue Biodistribution and Target mRNA Downregulation Following Systemic Administration of ASPH_0047 in Balb/c Mice Balb/C mice were treated with a single subcutaneous injection of ASPH_0047 (formulated in sterile physiological saline) at 5, 20 and 50 mg/kg animal body weight. Plasma and tissues were collected at the indicated times (from 3 individual animals), immediately snap-frozen and stored at −80° C. until analysis with an AEX-HPLC method (plasma/tissue PK) or for measurement of TGF-β2 and GAPDH mRNA levels by bDNA assay. TGF-β2 mRNA levels were expressed relative to GAPDH mRNA expression level in corresponding samples.

The data depict that a single subcutaneous bolus administration of 50 mg/kg ASPH_0047 resulted in rapid transfer of the drug from subcutaneous to circulating blood compartments ($T_{MAX}$ of ~5-30 min), biphasic pharmacokinetic profile in plasma, with rapid initial elimination phase (within the first 24 hrs), followed by long terminal half-life (FIG. 30*a*). It is further demonstrated that a marked long-lasting accumulation of the drug in various selected tissues. The major target organ (highest exposure/$C_{MAX}$) is the kidney, then the liver, skin and spleen, and lowest in the brain (data not shown). As also depicted in FIG. 30*b*, ASPH_0047 remained in the kidney tissue with pharmacological relevant doses (~50 μg/gr, equivalent to 10 μM) from 24 h and for up to 14 days, with consequent long-lasting and marked suppression of TGF-62 mRNA expression in the kidney tissue, with effective ~80% target mRNA downregulation observed for at least 14 days.

Example 28

Immunodeficient mice were injected subcutaneously with human 786-O renal cell carcinoma cells (FIG. 30A), pancreatic Panc1 cancer cells (FIG. 30B, C), or mouse SMA-560 glioma cells (FIG. 30D). When subcutaneous tumors reached the size of 100-300 $mm^3$ (established tumors), animals were treated subcutaneously, Q1Dx5, with saline (Mock), control oligonucleotide (Control; 50 mg/kg), inactive oligonucleotides in this context (e.g., ASPH_0065 and ASPH_0071; 50 mg/kg) or ASPH_0047 at 50 mg/kg, or the indicated doses. Tumors (FIG. 30A-D) and kidneys (FIG. 30E-F) were collected 24 hr after the last administration. Tumors/kidneys were then further processed for determination of TGF-□2 and GAPDH mRNA levels by bDNA assay. In these experiments, control oligonucleotide was a 18-mer, 3+3 LNA gapmer scrambled sequence. Results are expressed as TGF-beta2/GAPDH mRNA ratio, and each individual tested sample is represented with median values indicated as red line. Under described experimental conditions (schedule and route of administration), systemic repeated administrations of ASPH_0047 in Balb/c mice led to a sequence-specific downregulation of TGF-beta 2 mRNA in established subcutaneous tumors and kidneys.

Example 29

Balb/c mice were injected with mouse Renca cells into renal subcapsule (FIG. 32A, B) or i.v. (FIG. 32C, D) on Day 0. Systemic treatment with vehicle or indicated oligonucleotides started on Day 7 (FIG. 32A; 50 mg/kg, s.c., twice weekly), on Day 1 (FIG. 32B; 12.5 mg/kg, s.c., twice weekly) for two consecutive weeks, or on Day 7 (FIGS. 32C and 32D; indicated doses, s.c., twice weekly) for 26-27 days. Number of lung metastasis was macroscopically evaluated, and level of lung metastasis was determined by either number of metastasis (FIG. 32A, C) or based on lung weight (FIG. 32B, D). Results are represented as box plot; with median values, upper and lower quartiles, and 90th and 10th percentiles. Under described experimental designs, Balb/c mice treated with ASPH_0047 showed a reduced number of lung metastasis or reduced lung weight (lung weight correlates to extent of lung metastasis) in mouse Renca RCC models.

Example 30

Human Panc-1 pancreatic cancer cells were treated with 3.3 μM of the indicated oligonucleotides in the absence of transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta1 mRNA is shown in FIG. 32. The selective TGF-beta1 oligonucleotides only significantly inhibit TGF-beta1 mRNA expression while the control oligonucleotide LNA-scr does not affect expression of any TGF-beta isoform.

Example 31

Balb/c mice were injected with mouse 4T1 cells into mammary fat pad on Day 0. Systemic treatment with saline (Mock), pan-TGF-beta antibody (1D11), control oligonucleotide (LNA-scr), or ASPH_0047 started on Day 3 (30 mg/kg, s.c., twice weekly) and continued until D28, when animals were sacrificed. Number of lung metastasis was macroscopically evaluated, and level of lung metastasis was determined by either number of metastasis (left panel) or based on lung weight (right panel). Under described experimental design, treatment with ASPH_0047 reduced metastasis to the lungs, whereas the positive control, monoclonal TGF-beta antibody 1D11 had no effect on pulmonary metastasis in this model.

Example 32

CB17 SCID or Balb/c nude mice (n=3-5, except ASPH_0018 n=1 and ASPH_0037 n=2) were treated with 14-15 mg/kg of indicated LNA-modified oligonucleotides for four or five consecutive days (Q1Dx4-5). Plasma was collected 24 h after the last treatment and ALT levels were determined in plasma. Results are expressed as median values. Under this experimental condition, only 6/48 (12.5%) of tested oligonucleotides induced marked increase in plasma ALT (>300 units/l) indicating liver toxicity. The following Table 7 shows liver toxicity of systemically administered LNA-modified oligonucleotides:

| Name | ALT (units/l) |
|---|---|
| ASPH_0001 | 20.5 |
| ASPH_0003 | 20.0 |
| ASPH_0005 | 33.0 |
| ASPH_0009 | 834.0 |
| ASPH_0017 | 55.0 |
| ASPH_0018 | 7723.0 |
| ASPH_0022 | 28.5 |
| ASPH_0026 | 77.0 |
| ASPH_0027 | 75.0 |
| ASPH_0035 | 25.0 |
| ASPH_0036 | 131.5 |
| ASPH_0037 | 161.0 |
| ASPH_0041 | 655.0 |
| ASPH_0045 | 27.5 |
| ASPH_0046 | 3199.0 |
| ASPH_0047 | 42.5 |
| ASPH_0048 | 29.5 |
| ASPH_0065 | 27.0 |
| ASPH_0069 | 32.5 |
| ASPH_0071 | 23.5 |
| ASPH_0080 | 34.0 |
| ASPH_0082 | 31.0 |
| ASPH_0098 | 33.0 |
| ASPH_0105 | 40.0 |
| ASPH_0115 | 985.5 |
| ASPH_0190 | 902.0 |
| ASPH_0191 | 36.5 |
| ASPH_0192 | 49.5 |
| ASPH_0193 | 35.0 |
| ASPH_0005_C1 | 25.5 |
| ASPH_0005_C2 | 35.5 |
| ASPH_0005_C3 | 25.0 |
| ASPH_0036_C1 | 34.0 |
| ASPH_0036_C2 | 26.0 |
| ASPH_0036_C3 | 39.0 |
| ASPH_0045_C1 | 38.5 |
| ASPH_0045_C2 | 23.5 |
| ASPH_0045_C3 | 65.0 |
| ASPH_0047_C1 | 35.5 |
| ASPH_0047_C2 | 30.0 |
| ASPH_0047_C3 | 29.5 |
| ASPH_0047_C4 | 52.5 |
| ASPH_0047_C5 | 28.0 |
| ASPH_0047_C6 | 33.5 |
| ASPH_0047_C7 | 37.0 |
| ASPH_0047_C8 | 32.0 |
| ASPH_0047_C9 | 49.0 |
| ASPH_0047_C10 | 32.5 |

The invention claimed is:

1. A method of inhibiting and/or treating an ophthalmic disease associated with TGF-beta2 expression, comprising:

administering to a subject in need thereof an antisense oligonucleotide consisting of 12 to 18 nucleotides of the TGF-beta2 nucleic acid sequence of SEQ ID NO. 2, wherein one or more nucleotide(s) of the oligonucleotide is/are modified, and wherein the modified nucleotide is a LNA, and/or an ENA, polyalkylene oxide-, 2'-fluoro-, 2'-O-methoxy-, and/or 2'0-methyl-modified nucleotide; and said oligonucleotide consisting of GACCAGATGCAGGA (ASPH36, SEQ ID NO. 5).

2. The method of claim 1, wherein the modified nucleotide is located at the 5'- and/or 3'-end of the antisense oligonucleotide.

3. The method of claim 1, wherein the ophthalmic disease is selected from the group consisting of glaucoma, posterior capsular opacification, dry eye, Marfan or Loeys-Dietz syndrome, macular degeneration, retinoblastoma and choroidcarcinoma.

4. The method of claim 1, wherein the ophthalmic disease is macular degeneration and wherein the macular degeneration is an age-related macular degeneration, diabetic macular endma, or cataract.

5. A method of inhibiting and/or treating an ophthalmic disease associated with TGF-beta2 expression, comprising:

administering to a subject in need thereof a composition comprising an antisense oligonucleotide, said oligonucleotide consisting of GACCAGATGCAGGA (ASPH36, SEQ ID NO. 5).

6. A method of inhibiting and/or treating an ophthalmic disease associated with TGF-beta2 expression, comprising:

administering to a subject in need thereof an antisense oligonucleotide consisting of 12 to 18 nucleotides of the TGF-beta2 nucleic acid sequence of SEQ ID NO. 2, wherein one or more nucleotide(s) of the oligonucleotide is/are modified, wherein the modified nucleotide is a LNA, and/or an ENA, polyalkylene oxide-, 2'-fluoro-, 2'-O-methoxy-, and/or 2'0-methyl-modified nucleotide and wherein said oligonucleotide is selected from the group consisting of GACCAGATGCAGGA (ASPH36, SEQ ID NO. 5), CAAAGTATTTGGTCTCC (ASPH47, SEQ ID NO. 49), ACCTTGGGCTTGCG (ASPH1059, SEQ ID NO. 210) and CGGGTGCTGTTGTA (ASPH1132, SEQ ID NO. 267).

7. The method of claim 1, wherein said method is directed to treating an ophthalmic disease.

8. The method of claim 5, wherein said method is directed to treating an ophthalmic disease.

9. A method of treating an ophthalmic disease associated with TGF-beta2 expression, comprising:

administering to a subject in need thereof an antisense oligonucleotide consisting of 12 to 18 nucleotides of the TGF-beta2 nucleic acid sequence of SEQ ID NO. 2, wherein one or more nucleotide(s) of the oligonucleotide is/are modified, wherein the modified nucleotide is a LNA, and/or an ENA, polyalkylene oxide-, 2'-fluoro-, 2'-O-methoxy-, and/or 2'0-methyl-modified nucleotide and wherein said oligonucleotide is selected from the group consisting of GACCAGATGCAGGA (ASPH36, SEQ ID NO. 5), CAAAGTATTTGGTCTCC (ASPH47, SEQ ID NO. 49), ACCTTGGGCTTGCG (ASPH1059, SEQ ID NO. 210) and CGGGTGCTGTTGTA (ASPH1132, SEQ ID NO. 267).

10. The method of claim 9, wherein the ophthalmic disease is selected from the group consisting of glaucoma, posterior capsular opacification, dry eye, Marfan or Loeys-Dietz syndrome, macular degeneration, and choroidcarcinoma.

11. The method of claim 9, wherein the ophthalmic disease is macular degeneration and wherein the macular degeneration is an age-related macular degeneration, diabetic macular endma, or cataract.

* * * * *